(12) United States Patent
Giulianotti et al.

(10) Patent No.: US 10,066,002 B2
(45) Date of Patent: *Sep. 4, 2018

(54) METHODS OF PRODUCING TWO CHAIN PROTEINS IN BACTERIA

(71) Applicant: Genentech, Inc., South San Francisco, CA (US)

(72) Inventors: James Giulianotti, Belmont, CA (US); Dorothea Reilly, San Francisco, CA (US); Kieran Aurori, South San Francisco, CA (US); Laura C. Simmons, Burlingame, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/934,094

(22) Filed: Nov. 5, 2015

(65) Prior Publication Data

US 2016/0159880 A1    Jun. 9, 2016

Related U.S. Application Data

(60) Provisional application No. 62/075,798, filed on Nov. 5, 2014.

(51) Int. Cl.
| | |
|---|---|
| *A61K 39/395* | (2006.01) |
| *C07K 14/725* | (2006.01) |
| *C07K 16/00* | (2006.01) |
| *C07K 16/22* | (2006.01) |
| *C07K 16/24* | (2006.01) |
| *C07K 16/28* | (2006.01) |
| *C12P 21/00* | (2006.01) |
| *C12N 15/70* | (2006.01) |
| *A61K 39/00* | (2006.01) |
| *C12P 21/02* | (2006.01) |
| *C12P 21/08* | (2006.01) |

(52) U.S. Cl.
CPC .......... *C07K 14/7051* (2013.01); *C07K 16/00* (2013.01); *C07K 16/22* (2013.01); *C07K 16/244* (2013.01); *C07K 16/247* (2013.01); *C07K 16/2809* (2013.01); *C12N 15/70* (2013.01); *C12P 21/00* (2013.01); *C07K 2317/14* (2013.01); *C07K 2317/50* (2013.01); *C07K 2317/622* (2013.01); *C07K 2319/00* (2013.01)

(58) Field of Classification Search
None
See application file for complete search history.

(56) References Cited

U.S. PATENT DOCUMENTS

| | | |
|---|---|---|
| 4,676,980 A | 6/1987 | Segal et al. |
| 4,816,567 A | 3/1989 | Cabilly et al. |
| 5,500,362 A | 3/1996 | Robinson et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,894 A | 11/1996 | Wels et al. |
| 5,587,458 A | 12/1996 | King et al. |
| 5,591,828 A | 1/1997 | Bosslet et al. |
| 5,624,821 A | 4/1997 | Winter et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,237 A | 7/1997 | Carter |
| 5,648,260 A | 7/1997 | Winter et al. |
| 5,661,016 A | 8/1997 | Lonberg et al. |
| 5,731,168 A | 3/1998 | Carter et al. |
| 5,750,373 A | 5/1998 | Garrand et al. |
| 5,789,199 A | 8/1998 | Joly et al. |
| 5,807,706 A | 9/1998 | Carter et al. |
| 5,821,333 A | 10/1998 | Carter et al. |
| 5,821,337 A | 10/1998 | Carter et al. |
| 5,840,523 A | 11/1998 | Simmons et al. |
| 5,869,046 A | 2/1999 | Presta et al. |
| 6,075,181 A | 6/2000 | Kucherlapati et al. |
| 6,150,584 A | 11/2000 | Kucherlapati et al. |
| 6,194,551 B1 | 2/2001 | Idusogie et al. |
| 6,248,516 B1 | 6/2001 | Winter et al. |
| 6,737,056 B1 | 5/2004 | Presta |
| 6,982,321 B2 | 1/2006 | Winter |
| 7,087,409 B2 | 8/2006 | Barbas, III et al. |
| 7,189,826 B2 | 3/2007 | Rodman |
| 7,332,581 B2 | 2/2008 | Presta |
| 7,371,826 B2 | 5/2008 | Presta |

(Continued)

FOREIGN PATENT DOCUMENTS

| | | |
|---|---|---|
| DE | 266 710 A3 | 4/1989 |
| EP | 0 308 936 A2 | 3/1989 |
| EP | 0 404 097 A2 | 12/1990 |
| EP | 0 404 097 A3 | 12/1990 |

(Continued)

OTHER PUBLICATIONS

Wulfing et al., "Correctly Folded T-cell Receptor Fragments in the Periplasm of *Escherichia coli*" 242 Journal of Molecular Biology 655-669 (1994).*

(Continued)

*Primary Examiner* — Nancy J Leith

(74) *Attorney, Agent, or Firm* — Morrison and Foerster LLP

(57) ABSTRACT

Provided herein are methods of producing a recombinant polypeptide containing two chains, such as an immune mobilizing monoclonal T-cell receptor against cancer (ImmTAC) protein including an alpha chain and a beta chain. In particular, methods are provided for producing heterologous secretory proteins in bacteria through utilization of optimized expression vectors and culture processes.

27 Claims, 66 Drawing Sheets

Specification includes a Sequence Listing.

(56) References Cited

U.S. PATENT DOCUMENTS

| | | |
|---|---|---|
| 7,527,791 B2 | 5/2009 | Adams et al. |
| 7,569,644 B2 | 8/2009 | Shimo et al. |
| 7,642,228 B2 | 1/2010 | Carter et al. |
| 7,695,936 B2 | 4/2010 | Carter et al. |
| 8,088,618 B2 | 1/2012 | Fung et al. |
| 8,216,805 B2 | 7/2012 | Carter et al. |
| 8,361,744 B2 | 1/2013 | Marrichi et al. |
| 8,715,669 B2 | 5/2014 | Masternak et al. |
| 8,771,697 B2 | 7/2014 | Masternak et al. |
| 2005/0014934 A1 | 1/2005 | Hinton et al. |
| 2005/0079574 A1 | 4/2005 | Bond |
| 2005/0119455 A1 | 6/2005 | Fuh et al. |
| 2005/0266000 A1 | 12/2005 | Bond et al. |
| 2007/0117126 A1 | 5/2007 | Sidhu et al. |
| 2007/0160598 A1 | 7/2007 | Dennis et al. |
| 2007/0237764 A1 | 10/2007 | Birtalan et al. |
| 2007/0292936 A1 | 12/2007 | Barthelemy et al. |
| 2009/0002360 A1 | 1/2009 | Chen et al. |
| 2013/0089553 A1 | 4/2013 | Carter et al. |
| 2016/0015898 A1 | 6/2016 | Giulianotti |

FOREIGN PATENT DOCUMENTS

| | | | |
|---|---|---|---|
| EP | 0 404 097 B1 | 12/1990 | |
| EP | 1 356 052 B1 | 8/2008 | |
| EP | 1 691 833 B1 | 3/2010 | |
| WO | WO-91/00360 A1 | 1/1991 | |
| WO | WO-1991/10741 A1 | 7/1991 | |
| WO | WO-92/20373 A1 | 11/1992 | |
| WO | WO-1993/01161 A1 | 1/1993 | |
| WO | WO-93/08829 A1 | 5/1993 | |
| WO | WO-93/16185 A2 | 8/1993 | |
| WO | WO-93/16185 A3 | 8/1993 | |
| WO | WO-94/04690 A1 | 3/1994 | |
| WO | WO-94/29351 A2 | 12/1994 | |
| WO | WO-94/29351 A3 | 12/1994 | |
| WO | WO-96/27011 A1 | 9/1996 | |
| WO | WO-1996/33735 A1 | 10/1996 | |
| WO | WO-1996/34096 A1 | 10/1996 | |
| WO | WO-1998/24893 A2 | 6/1998 | |
| WO | WO-1998/24893 A3 | 6/1998 | |
| WO | WO-99/51642 A1 | 10/1999 | |
| WO | WO-00/55183 A1 | 9/2000 | |
| WO | WO-00/69914 A2 | 11/2000 | |
| WO | WO-02/40697 A2 | 5/2002 | |
| WO | WO 2002/061090 A2 * | 8/2002 | ............. C12N 15/70 |
| WO | WO-03/018771 A2 | 3/2003 | |
| WO | WO 2003/020763 A2 * | 3/2003 | ......... C07K 14/7051 |
| WO | WO-2004/009776 A2 | 1/2004 | |
| WO | WO-2004/056312 A2 | 7/2004 | |
| WO | WO-2004/056312 A3 | 7/2004 | |
| WO | WO-2004/106381 A1 | 12/2004 | |
| WO | WO-2005/010044 A2 | 2/2005 | |
| WO | WO-2005/061547 A2 | 7/2005 | |
| WO | WO-2005/062967 A2 | 7/2005 | |
| WO | WO-2005/100402 A1 | 10/2005 | |
| WO | WO-2006/028936 A2 | 3/2006 | |
| WO | WO-2006/028936 A3 | 3/2006 | |
| WO | WO-2006/029879 A2 | 3/2006 | |
| WO | WO-2006/029879 A3 | 3/2006 | |
| WO | WO-2007/042261 A2 | 4/2007 | |
| WO | WO-2008/119567 A2 | 10/2008 | |
| WO | WO-2009/136286 A2 | 11/2009 | |
| WO | WO-2011/133886 A2 | 10/2011 | |
| WO | WO-2012/106615 A1 | 8/2012 | |
| WO | WO-2014/165771 A2 | 10/2014 | |
| WO | WO-2015/127405 A2 | 8/2015 | |
| WO | WO-2016/073791 A1 | 5/2016 | |

OTHER PUBLICATIONS

Wu et al., "Effect of Heat-Shock Proteins for Relieing Physiological Stress and Enhancing the Production of Penicillin Acylase in *Escherichia coli*" 96 Biotechnology and Bioengineering 956-966 (Sep. 14, 2006).*

Lee et al., "High cell-density culture of *Escherichia coli*" 14 Trends in Biotechnology 98-105 (1996).*

Almagro et al. "Humanization of antibodies," *Front. Biosci.* 13:1619-1633, (Jan. 1, 2008).

Altschul et al. "Gapped BLAST and PSI-BLAST: A New Generation of Protein Database Search Programs," *Nuc. Acids Res.* 25(17):3389-3402, (1997).

Altschul et al. "Basic Local Alignment Search Tool," *J. Mol. Biol.* 215:403-410, (1990).

Arbabi-Ghahroudi et al. "Prokaryotic Expression of Antibodies," *Cancer and Metastasis Reviews* 24(4):501-519, (Dec. 1, 2005).

Baca et al. "Antibody Humanization Using Monovalent Phage Display," *J. Biol. Chem.* 272(16):10678-10684, (Apr. 18, 1997).

Baneyx et al. "In Vivo Degradation of Secreted Fusion Proteins by the *Escherichia coli* Outer Membrane Protease OmpT," *J. Bacteriol.* 172(1):491-494, (Jan. 1990).

Boerner et al. "Production of Antigen-Specific Human Monoclonal Antibodies From In Vitro-Primed Human Splenocytes," *J. Immunol.* 147(1):86-95, (Jul. 1, 1991).

Bolivar et al. "Construction and Characterization of New Cloning Vehicles. II. A Multipurpose Cloning System," *Gene* 2:95-113, (1977).

Bostrom et al. "Variants of the Antibody Herceptin That Interact with HER2 and VEGF at the Antigen Binding Site," *Science* 323:1610-1614, (Mar. 20, 2009).

Bothmann et al. "The Periplasmic *Escherichia coli* Peptidylprolyl cis,trans-Isomerase FkpA," *J. Biol. Chem.* 275:17100-17105, (Jun. 2, 2000).

Brennan et al. "Preparation of Bispecific Antibodies by Chemical Recombination of Monoclonal Immunoglobulin $G_1$ Fragments," *Science*, 229:81-83, (Jul. 5, 1985).

Brüggemann et al. "Comparison of the Effector Functions of Human Immunoglobulins Using a Matched Set of Chimeric Antibodies," *J. Exp. Med.* 166:1351-1361, (Nov. 1, 1987).

Brüggemann et al. "Designer Mice: The Production of Human Antibody Repertoires in Transgenic Animals," *Year in Immunol* 7:33-40, (1993).

Carter et al. "Humanization of an Anti-p185$^{HER2}$ Antibody for Human Cancer Therapy," *Proc. Natl. Acad. Sci. USA*, 89:4285-4289, (May 1992).

Carter et al. "High Level *Escherichia coli* Expression and Production of a Bivalent Humanized Antibody Fragment," *Bio/Technology* 10:163-167, (Feb. 1992).

Chang et al. "Construction and Characterization of Amplifiable Multicopy DNA Cloning Vehicles Derived from the P15A Cryptic Miniplasmid," *J. Bacteriol.* 134(3):1141-1156, (Jun. 1978).

Chang et al. "High-level Secretion of Human Growth Hormone by *Escherichia coli*," *Gene* 55:189-196, (1987).

Charlton. "Expression and Isolation of Recombinant Antibody Fragments in *E. coli*," Chapter 14 in *Methods in Molecular Biology*, B.K.C. Lo, ed., Humana Press Inc., Totowa, N.J., 248:245-254, (2003).

Chen et al. "Selection and Analysis of an Optimized Anti-VEGF Antibody: Crystal Structure of an Affinity-matured Fab in Complex with Antigen," *J. Mol. Biol.* 293-865-881, (1999).

Chintalacharuvu et al. "Cysteine Residues Required for the Attachment of the Light Chain in Human IgA2," *J. Immunol.* 169(9):5072-5077, (2002).

Chothia. "The Nature of the Accessible and Buried Surfaces in Proteins," *J. Mol. Biol.* 105:1-14, (1975).

Chothia et al. "Canonical Structures for the Hypervariable Regions of Immunoglobulins," *J. Mal. Biol.* 196:901-917, (1987).

Chowdhury. "Engineering Hot Spots for Affinity Enhancement of Antibodies," Chapter 11 in *Methods in Molecular Biology*, M. Welschof, et al. ed., Humana Press Inc., Totowa, NJ, 207:179-196, (2008).

Clackson et al. "Making Antibody Fragments Using Phage Display Libraries," *Nature* 352:624-628, (Aug. 15, 1991).

(56) References Cited

OTHER PUBLICATIONS

Clynes et al. "Fc Receptors are Required in Passive and Active Immunity to Melanoma," *Proc. Natl. Acad. Sci. USA* 95:652-656, (Jan. 1998).
Cole et al. "The EBV-Hybridoma Technique and its Application to Human Lung Cancer," in *Monoclonal Antibodies and Cancer Therapy*, Ralph A. Reisfeld et al., ed., Alan R. Liss, Inc., p. 77-96, (1985).
Cragg et al. "Complement-Mediated Lysis by Anti-CD20 mAb Correlates With Segregation Into Lipid Rafts," *Blood* 101(3):1045-1052, (Feb. 1, 2003).
Cragg et al. "Antibody Specificity Controls in Vivo Effector Mechanisms of Anti-CD20 Reagents," *Blood* 103(7):2738-2743, (Apr. 1, 2004).
Cunningham et al. "High-Resolution Epitope Mapping of hGH-Receptor Interactions by Alanine-Scanning Mutagenesis," *Science* 244:1081-1085, (Jun. 2, 1989).
Dall' Acqua et al. "Antibody Humanization by Framework Shuffling," *Methods* 36:43-60, (2005).
Devereaux et al. "A Comprehensive Set of Sequence Analysis Programs for the VAX," *Nuc. Acids Res.* 12(1):387-395, (1984).
Duncan et al. "The Binding Site for Clq on IgG," *Nature* 322:738-740, (Apr. 21, 1988).
Fellouse et al. "Synthetic Antibodies From a Four-Amino-Acid Code: A Dominant Role for Tyrosine in Antigen Recognition," *Proc. Natl. Acad. Sci. USA* 101(34):12467-12472, (Aug. 24, 2004).
Feng et al. "Progressive Sequence Alignment as a Prerequisite to Correct Phylogenetic Trees," *J. Mol. Evol.* 25:351-360, (1987).
Fishwild et al. "High-Avidity Human IgGK Monoclonal Antibodies From a Novel Strain of Minilocus Transgenic Mice," *Nature Biotechnol.* 14:845-851, (Jul. 1996).
Gaffen. "Structure and Signalling in the IL-17 Receptor Superfamily," *Nature Review* 9(8):556-567, (Aug. 2009).
Garcia-Ochoa et al. "Bioreactor Scale-Up and Oxygen Transfer Rate in Microbial Processes: An Overview," *Biotechnology Advances* 27:153-176, (2009, e-pub. Nov. 12, 2008).
Gazzano-Santoro et al. "A Non-Radioactive Complement-Dependent Cytotoxicity Assay for Anti-CD20 Monoclonal Antibody" *J. Immunol. Methods* 202:163-171, (1996).
Golden et al. "High-Level Production of a Secreted, Heterodimeric α β Murine T-cell Receptor in *Escherichia coli*," *Journal of Imunological Methods* 206(1-2):163-169, (Aug. 7, 1997).
Griffiths et al. "Human Anti-Self Antibodies With High Specificity From Phage Display Libraries," *EMBO J.* 12(2):725-734, (1993).
Groff et al. "Engineering Toward a Bacterial "Endoplasmic Reticulum" for the Rapid Expression of Immunoglobulin Proteins," *mAbs* 6(3):671-678, (May 2014, epub. Feb. 11, 2014).
Gruber et al. "Efficient Tumor Cell Lysis Mediated by a Bispecific Single Chain Antibody Expressed in *Escherichia coli*," *J. Immunol.* 152:5368-5374, (1994).
Guss et al. "Structure of the IgG-Binding Regions of Streptococcal Protein G," *EMBO J.* 5(7):1567-1575, (1986).
Guyer et al. "Immunoglobulin Binding by Mouse Intestinal Epithelial Cell Receptors," *J. Immunol.* 117(2):587-593, (Aug. 1976).
Hamers-Casterman et al. "Naturally Occurring Antibodies Devoid of Light Chains," *Nature* 363:446-448, (Jun. 3, 1993).
Hammerling et al. "Production of Hybridomas in the Rodent System" in *Monoclonal Antibodies and T-Cell Hybridomas*, Elsevier, N.Y., pp. 563-587, (1981).
Harris. "Production of Humanized Monoclonal Antibodies for in vivo Imaging and Therapy," *Biochem. Soc. Transactions* 23(4):1035-1038, (1995).
Hellström et al. "Strong Antitumor Activities of IgG3 Antibodies to a Human Melanoma-Associated Ganglioside," *Proc. Natl Acad. Sci. USA* 82:1499-1502, (Mar. 1985).
Hellström et al. "Antitumor Effects of L6, an IgG2a Antibody That Reacts With Most Human Carcinomas," *Proc. Natl Acad. Sci. USA* 83:7059-7063, (Sep. 1986).

Helm et al. "The Nature and Importance of the Inter-ε Chain Disulfide Bonds in Human IgE," *Eur. J. Immunol.* 21(6):1543-1548, (Jun. 1991).
Henikoff et al. "Amino Acid Substitution Matrices From Protein Blocks" *Proc. Natl. Acad. Sci. USA* 89:10915-10919, (Nov. 1992).
Higgins et al. "Fast and Sensitive Multiple Sequence Alignments on a Microcomputer," *CABIOS Communications* 5(2):151-153, (1989).
Holliger et al. ""Diabodies": Small Bivalent and Bispecific Antibody Fragments," *Proc. Natl. Acad. Sci. USA* 90: 6444-6448, (Jul. 1993).
Hongo et al. "Development and Characterization of Murine Monoclonal Antibodies to the Latency-Associated Peptide of Transforming Growth Factor $\beta_1$," *Hybridoma* 14(3):253-260, (1995).
Hoogenboom et al. "By-passing Immunisation Human Antibodies from Synthetic Repertoires of Germline $V_H$ Gene Segments Rearranged in Vitro," *J. Mol. Biol.* 227:381-388, (1992).
Hoogenboom et al. "Overview of Antibody Phage-Display Technology and Its Applications" Chapter 1 in *Methods in Molecular Biology*, O'Brien, P.M et al. eds., Humana Press, Inc., Totowa, NJ, 178:1-37, (2001).
Hsieh et al. "Global Regulation by the Seven-component $P_i$ Signaling System," *Curr. Opin. Microbiol.* 13(2):198-203, (Apr. 2010).
Hudson et al. "Engineered Antibodies," *Nat. Med.* 9(1):129-134, (Jan. 2003).
Humphreys et al. "High-Level Periplasmic Expression in *Escherichia coli* Using a Eukaryotic Signal Peptide: Importance of Codon Usage at the 5' End of the Coding Sequence," *Protein Expr. Purif.* 20(2):252-264, (2000).
Hurle et al. "Protein Engineering Techniques for Antibody Humanization," *Curr. Op. Biotech.* 5:428-433, (1994).
Hymowitz et al. "IL-17s Adopt a Cystine Knot Fold: Structure and Activity of a Novel Cytokine, IL-17F, and Implications for Receptor Binding," *EMBO J.* 20(19):5332-5341, (2001).
Idusogie et al. "Mapping of the C1q Binding Site on Rituxan, a Chimeric Antibody With a Human IgG1 Fc," *J. Immunol.* 164:4178-4184, (2000).
Jakobovits et al. "Germ-Line Transmission and Expression of a Human-Derived Yeast Artificial Chromosome," *Nature* 362:255-258, (Mar. 18, 1993).
Jakobovits et al. "Analysis of Homozygous Mutant Chimeric Mice: Deletion of the immunoglobulin Heavy-Chain Joining Region Blocks B-cell Development and Antibody Production" *Proc. Natl. Acad. Sci. USA* 90:2551-2555, (1993).
Jang et al. "A Novel Selection Marker for Efficient DNA Cloning and Recombineering in *E. coli*," *PLoS One* 8(2):e57075:1-7, (Feb. 2013).
Johnson et al. "The Kabat Database and a Bioinformatics Example" Chapter 2 in *Methods in Molecular Biology*, Lo, B.K.C., ed., Humana Press Inc., Totowa, N.J., 248:11-25, (2003).
Jones et al. "Replacing the Complementarity-Determining Regions in a Human Antibody With Those From a Mouse," *Nature* 321:522-525, (May 29, 1986).
Karlin et al. "Applications and Statistics for Multiple High-Scoring Segments in Molecular Sequences," *Proc. Natl. Acad. Sci. USA* 90:5873-5877, (Jun. 1993).
Kashmiri et al. "SDR grafting—A New Approach to Antibody Humanization," *Methods* 36:25-34, (2005).
Kikuchi et al. "The Nucleotide Sequence of the Promoter and the Amino-Terminal Region of Alkaline Phosphatase Structural Gene (phoA) of *Escherichia coli*," *Nucleic Acids Res.* 9(21):5671-5678, (1981).
Kim et al. "Localization of the Site of the Murine IgG1 Molecule That is Involved in Binding to the Murine Intestinal Fc Receptor," *J. Immunol.* 24:2429-2434, (1994).
Klimka et al. "Human Anti-CD30 Recombinant Antibodies by Guided Phage Antibody Selection Using Cell Panning," *Br. J. Cancer* 83(2):252-260, (2000).
Köhler et al. "Continuous Cultures of Fused Cells Secreting Antibody of Predefined Specificity," *Nature* 256:495-497, (Aug. 7, 1975).
Kostelny et al. "Formation of a Bispecific Antibody by the Use of Leucine Zippers," *J. Immunol.* 148(5):1547-1553, (Mar. 1, 1992).

(56) References Cited

OTHER PUBLICATIONS

Lee et al. "High-Affinity Human Antibodies From Phage-Displayed Synthetic Fab Libraries With a Single Framework Scaffold," *J. Mol. Biol.* 340(5):1073-1093, (2004).
Lee et al. "Bivalent Antibody Phage Display Mimics Natural Immunoglobulin," *J. Immunol. Methods* 284(1-2):119-132, (2004).
Levy et al. "Production of Correctly Folded Fab Antibody Fragment in the Cytoplasm of *Escherichia coli* trxB gor Mutants via the Coexpression of Molecular Chaperones," *Protein Expression and Purification* 23(2):338-347, (Nov. 1, 2001).
Levy et al. "Enhancement of Antibody Fragment Secretion Into the *Escherichia coli* Periplasm by Co-Expression With the Peptidyl Prolyl Isomerase, FkpA, in the Cytoplasm," *Journal of Immunological Methods* 394(1):10-21, (Apr. 23, 2013).
Li et al. "Human Antibodies for Immunotherapy Development Generated Via a Human B Cell Hybridoma Technology," *Proc. Natl. Acad. Sci. USA* 103(10):3557-3562, (Mar. 7, 2006).
Liddy et al. "Monoclonal TCR-Redirected Tumor Cell Killing," *Nature Medicine* 18(6):980-987, (Jun. 2012).
Lindmark et al. "Binding of Immunoglobulins to Protein A and Immunoglobulin Levels in Mammalian Sera," *J. Immunol. Meth.* 62:1-13, (1983).
Liu et al. "Disulfide Bond Structures of IgG Molecules—Structural Variations, Chemical Modifications and Possible Impacts to Stability and Biological Function," *MAbs* 4(1):17-23, (Feb. 2012).
Lonberg et al. "Antigen-Specific Human Antibodies From Mice Comprising Four Distinct Genetic Modifications," *Nature* 368:856-859, (Apr. 28, 1994).
Lonberg et al. "Human Antibodies from Transgenic. Mice" *Intern. Rev. Immunol.* 13:65-93, (1995).
Lonberg. "Fully Human Antibodies From Transgenic Mouse and Phage Display Platforms," *Curr. Opin. Immunol.* 20:450-459, (2008).
Lübke et al. "Analysis and Optimization of Recombinant Protein Production in *Escherichia coli* Using the Inducible pho A Promoter of the *E. coli* Alkaline Phosphatase," *Enzyme Microb. Technol.* 17(10):923-928, (1995).
Marks et al. "By-Passing Immunization Human Antibodies from V-Gene Libraries Displayed on Phage," *J. Mol. Biol.* 222:581-597, (1991).
Marks et al. "By-Passing Immunization: Building High Affinity Human Antibodies by Chain Shuffling," *Bio/Technology* 10:779-783, (Jul. 1992).
Marks et al. "Selection of Human Antibodies From Phage Display Libraries," Chapter 8 in *Methods in Molecular Biology*, Lo, B.K.C, ed., Humana Press Inc., Totowa, N.J., 248:161-175, (2003).
McCafferty et al. "Phage Antibodies: Filamentous Phage Displaying Antibody Variable Domains," *Nature* 348:552-554, (Dec. 6, 1990).
Merchant et al. "An Efficient Route to Human Bispecific IgG," *Nature Biotechnology* 16(7):677-681, (Jul. 1, 1998).
Millstein et al. "Hybrid Hybridomas and Their Use in Immunohistochemistry," *Nature* 305:537-539, (Oct. 6, 1983).
Morimoto et al. "Single-Step Purification of F(ab')$_2$ Fragments of Mouse Monoclonal Antibodies (Immunoglobulins GI) by Hydrophobic Interaction High Performance Liquid Chromatography Using TSKgel Phenyl-5PW," *Journal of Biochemical and Biophysical Methods* 24:107-117, (1992).
Morrison et al. "Chimeric Human Antibody Molecules: Mouse Antigen-Binding Domains With Human Constant Region Domains," *Proc. Natl. Acad. Sci. USA* 81:6851-6855, (Nov. 1984).
Morrison. "Success in specification" *Nature* 368: 812-813, (Apr. 28, 1994).
Needleman et al. "A General Method Applicable to the Search for Similarities in the Amino Acid Sequence of Two Proteins," *J. Mol. Biol.* 48:443-453, (1970).
Nelson et al. "Development Trends for Human Monoclonal Antibody Therapeutics," *Nature Review Drug Discovery* 9:767-774, (Oct. 2010).
Neuberger. "Generating High-Avidity Human Mabs in Mice," *Nature Biotechnol.* 14:826, (Jul. 1996).

Ni. "Research Progress and Future Perspectives in Antibodomics and Antibodomic Drugs," *Xiandai Mianyixue* 26(4):265-268, (2006). (English Abstract Only.).
Oates et al. "ImmTACs for Targeted Cancer Therapy: Why, What, How, and Which," *Molecular Immunology* 67(2):67-74, (2015, e-pub. Feb. 21, 2015).
Oates et al. "ImmTACs. Novel Bi-Specific Agents for Targeted Cancer Therapy," *OncoImmunology* 2(2):e22891-1-e22891-3, (2013, e-pub. Feb. 1, 2013).
Osbourn et al. "From Rodent Reagents to Human Therapeutics Using Antibody Guided Selection," *Methods* 36:61-68, (2005).
Padlan. "A Possible Procedure for Reducing the Immunogenicity of Antibody Variable Domains While Preserving Their Ligand-Binding Properties," *Mol. Immunol.* 28(4/5):489-498, (1991).
Pearson et al. "Improved Tools for Biological Sequence Comparison" *Proc. Natl. Acad. Sci. USA* 85:2444-2448, (Apr. 1988).
Pearson. "Effective Protein Sequence Comparison," *Methods Enzymol.* 266:227-258, (1996).
Petkova et al. "Enhanced Half-Life of Genetically Engineered Human IgG1 Antibodies in a Humanized FcRn Mouse Model: Potential Application in Humorally Mediated Autoimmune Disease," *International Immunol.* 18(12):1759-1769, (2006, e-pub. Oct. 31, 2006).
Picken et al. "Nucleotide Sequence of the Gene for Heat-Stable Enterotoxin II of *Escherichia coli,*" *Infect. Immun.* 42(1):269-275, (Oct. 1983).
Plückthun. "Antibodies from *Escherichia coli*," Chapter 11 in *The Pharmacology of Monoclonal Antibodies*, Rosenburg, M. et al. eds., Springer-Verlag, New York, 113:269-315, (1994).
Presta. "Antibody Engineering," *Curr. Op. Struct. Biol.* 2:593-596, (1992).
Presta et al. "Humanization of an Antibody Directed Against IgE," *J. Immunol.*, 151:2623-2632, (Sep. 1, 1993).
Queen et al. "A Humanized Antibody That Binds to the Interleukin 2 Receptor," *Proc. Natl Acad. Sci. USA* 86:10029-10033, (Dec. 1989).
Ravetch et al. "Fc Receptors," *Annu. Rev. Immunol.* 9:457-492, (1991).
Ridgway et al. "'Knobs-Into-Holes' Engineering of Antibody $C_H3$ Domains for Heavy Chain Heterodimerization," *Protein Eng.* 9(7):617-621, (1996).
Riechmann et al. "Reshaping Human Antibodies for Therapy," *Nature* 332:323-329, (Mar. 24, 1988).
Rosok et al. "A Combinatorial Library Strategy for the Rapid Humanization of Anticarcinoma BR96 Fab," *J. Biol. Chem.* 271(37):22611-22618, (Sep. 13, 1996).
Schlapschy et al. "A System for Concomitant Overexpression of Four Periplasmic Folding Catalysts to Improve Secretory Protein Production in *Escherichia coli*," *Protein Engineering, Design and Selection* 19(8):385-390, (2006, e-pub. May 23, 2006).
Scholtissek et al. "A Cloning Cartridge of λ $t_0$ Terminator," *Nucleic Acids Res.* 15(7):3185, (1987).
Shalaby et al. "Development of Humanized Bispecific Antibodies Reactive with Cytotoxic Lymphocytes and Tumor Cells Overexpressing the HER2 Protooncogene," *J. Exp. Med.* 175: 217-225, (Jan. 1992).
Shalaby et al. "Bispecific HER2x CD3 Antibodies Enhance T-Cell Cytotoxicity in Vitro and Localize to HER2-Overexpressing Xenografts in Nude Mice," *Clinical Immunology and Immunopathology* 74(2):185-192, (Feb. 1995).
Sheriff et al. "Redefining the Minimal Antigen-Binding Fragment," *Nature Struct. Biol.* 3(9):733-736, (Sep. 1996).
Shields et al. "High Resolution Mapping of the Binding Site on Human IgGI for Fcγ RI, FcγRII, FcγRIII, and FcRn and Design of IgG1 Variants with Improved Binding to the FcγR," *J. Biol. Chem.* 9(2):6591-6604, (Mar. 2, 2001).
Shin et al. "Structural and Functional Properties of Mouse-Human Chimeric IgD," *Hum. Antibodies Hybridomas* 3(2):65-74, (1992).
Sidhu et al. "Phage-Displayed Antibody Libraries of Synthetic Heavy Chain Complementarity Determining Regions," *J. Mol. Biol.* 338(2):299-310, (2004).

(56) References Cited

OTHER PUBLICATIONS

Simmons et al. "Translational Level is a Critical Factor for the Secretion of Heterologous Proteins in *Escherichia coli*," *Nat. Biotechnol.* 14:629-634, (May 1996).
Simmons et al. "Expression of Full-Length Immunoglobulins in *Escherichia coli*: Rapid and Efficient Production of Aglycosylated Antibodies," *Journal of Immunological Methods* 263:133-147, (2002).
Sims et al. "A Humanized CD18 Antibody Can Block Function without Cell Destruction," *J. Immunol.* 151(4):2296-2308, (Aug. 15, 1993).
Smith et al. "Comparison of Biosequences," *Adv. Appl. Math.* 2:482-489, (1981).
Spadiut et al. "Microbials for the Production of Monoclonal Antibodies and Antibody Fragments," *Trends in Biotechnology* 32(1):54-60, (Jan. 2014).
Spiess et al. "A Temperature-Dependent Switch from Chaperone to Protease in a Widely Conserved Heat Shock Protein," *Cell* 97:339-347, (Apr. 30, 1999).
Spiess et al. "Bispecific Antibodies With Natural Architecture Produced by Co-Culture of Bacteria Expressing Two Distinct Half-Antibodies," *Nature Biotechnology* 31(8):753-758, (Aug. 2013).
Suresh et al. "Bispecific Monoclonal Antibodies From Hybrid Hybridomas," *Methods in Enzymology* 121:210-228, (1986).
Sutcliffe. "Complete Nucleotide Sequence of the Escherichia coli Plasmid pBR322," *Cold Spring Harbor Symp. Quant. Biol.* 43:77-90, (1979).
Terpe. "Overview of Bacterial Expression Systems for Heterologous Protein Production: From Molecular and Biochemical Fundamentals to Commercial Systems," *Appl. Microbiol. Biotechnol.* 72:211-222, (2006).
Thompson et al. "Clustal W: Improving the Sensitivity of Progressive Multiple Sequence Alignment Through Sequence Weighting, Position-Specific Gap Penalties and Weight Matrix Choice," *Nucl Acids. Res.* 22(22):4673-4680, (1994).
Traunecker et al. "Bispecific Single Chain Molecules (Janusins) Target Cytotoxic Lymphocytes on HIV Infected Cells," *EMBO J.* 10(12):3655-3659, (1991).
Tutt et al. "Trispecific F(ab')₃ Derivatives That Use Cooperative Signaling Via the TCR/CD3 Complex and CD2 to Activate and Redirect Resting Cytotoxic T Cells," *J. Immunol.* 147:60-69, (Jul. 1, 1991).
Van Dijk et al. "Human Antibodies as Next Generation Therapeutics," *Curr. Opin. Chem. Biol.* 5:368-374, (2001).
Vaswani et al. "Humanized Antibodies as Potential Therapeutic Drugs," *Ann. Allergy, Asthma & Immunol.* 81:105-119, (Aug. 1998).
Vimberg et al. "Translation Initiation Region Sequence Preferences in *Escherichia coli*," *BMC Mol. Biol.* 8(100):1-13, (2007, e-pub. Oct. 31, 2007).
Vollmers et al. "The "Early Birds": Natural IgM Antibodies and Immune Surveillance," *Histology and Histopathology* 20(3):927-937, (2005).
Vollmers et al. "Death by Stress: Natural IgM-Induced Apoptosis," *Methods and Findings in Experimental and Clinical Pharmacology* 27(3):185-191, (2005).
Wiersma et al. "Assembly of IgM. Role of Disulfide Bonding and Noncovalent Interactions," *J. Immunol.* 154(10):5265-5272, (1995).
Winter et al. "Making Antibodies by Phage Display Technology," *Ann. Rev. Immunol.* 12:433-455, (1994).
Wu et al. "Simultaneous Targeting of Multiple Disease Mediators by a Dual-Variable-Domain Immunoglobulin," *Nature Biotechnology* 25(11):1290-1297, (Nov. 2007).
Xu et al. "Diversity in the CDR3 Region of Vh is Sufficient for Most Antibody Specificities," *Immunity* 13:37-45, (Jul. 2000).
Zamyatnin. "Protein Volume in Solution," *Prog. Biophys. Mol. Biol.* 24:107-123, (1972).
Zapata et al."Engineering linear F(ab')₂ Fragments for Efficient Production in *Escherichia coli* and Enhanced Antiproliferative Activity," *Protein Eng*, 8(10):1057-1062, (1995).

Zhang et al. "Fluorescent Site-Specific Labeling of *Escherichia coli* Expressed Proteins with Sfp Phosphopantetheinyl Transferase," Chapter 18 in *Heterologous Gene Expression in E. coli, Methods in Molecular Biology*, Evans, Jr., T.C. et al. eds., Humana Press, 705:295-307, (2011).
International Search Report dated Feb. 25, 2016, for PCT Application No. PCT/US2015/059339, filed on Nov. 5, 2015, 5 pages.
Written Opinion dated Feb. 25, 2016, for PCT Application No. PCT/US2015/059339, filed on Nov. 5, 2015, 8 pages.
International Search Report dated Jan. 27, 2016, for PCT Application No. PCT/US2015/059342, filed on Nov. 5, 2015, 7 pages.
Written Opinion dated Jan. 27, 2016, for PCT Application No. PCT/US2015/059342, filed on Nov. 5, 2015, 6 pages.
Gunnarsen et al. "Chaperone-Assisted Thermostability Engineering of a Soluble T Cell Receptor Using Phage Display," *Scientific Reports* 3(1162):1-10, (2013).
Gunnarsen et al. "Periplasmic Expression of Soluble Single Chain T Cell Receptors is Rescued by the Chaperone FkpA," *BMC Biotechnology* 10(8):1-13, (2010).
Løset et al. "Functional Phage Display of Two Murine α/β T-Cell Receptors is Strongly Dependent on Fusion Format, Mode and Periplasmic Folding Assistance," *Protein Engineering, Design & Selection* 20(9):461-472, (2007, e-pub. Oct. 9, 2007).
Office Action Appendix AAB66417, dated Apr. 4, 2001, "Human Fab Clone LD9 VL CDR2," located at <http://score.uspto.gov/ScoreAccessWeb/getItem.htm?AppId=14934100&seqId=09323b678 . . . >, last visited on Aug. 3, 2017, 2 pages.
Office Action Appendix ADJ67621, dated May 6, 2004, "TNFalpha Antibody D2E7 VH Chain CDR1 Fragment," located at <http://score.uspto.gov/ScoreAccessWeb/getItem.htm?AppId=14934100&seqId=09323b678 . . . >, last visited on Aug. 3, 2017, 2 pages.
Office Action Appendix AEB21450, dated Sep. 22, 2005, "Mouse Anti-IL-13 MAb 228B/C-1 VK CDR 1," located at <http://score.uspto.gov/ScoreAccessWeb/getItem.htm?AppId=14934100&seqId=09323b678 . . . >, last visited on Aug. 3, 2017, 2 pages.
Office Action Appendix AEB21455, dated Sep. 22, 2005, "Mouse Anti-IL-13 MAb 228B/C-1 VK CDR 2," located at <http://score.uspto.gov/ScoreAccessWeb/getItem.htm?AppId=14934100&seqId=09323b678 . . . >, last visited on Aug. 4, 2017, 2 pages.
Office Action Appendix AEB21466, dated Sep. 22, 2005, "Mouse Anti-IL-13 MAb 228B/C-1 VK CDR 3," located at <http://score.uspto.gov/ScoreAccessWeb/getItem.htm?AppId=14934100&seqId=09323b678 . . . >, last visited on Aug. 3, 2017, 2 pages.
Office Action Appendix AEB21468, dated Sep. 22, 2005, "Mouse Anti-IL-13 MAb 228B/C-1 VH CDR 1," located at <http://score.uspto.gov/ScoreAccessWeb/getItem.htm?AppId=14934100&seqId=09323b678 . . . >, last visited on Aug. 3, 2017, 2 pages.
Office Action Appendix AEB21474, dated Sep. 22, 2015, "Mouse Anti-IL-13 MAb 228B/C-1 VH CDR 2," located at <http://score.uspto.gov/ScoreAccessWeb/getItem.htm?AppId=14934100&seqId=09323b678 . . . >, last visited on Aug. 3, 2017, 2 pages.
Office Action Appendix AEB21486, dated Sep. 22, 2005, "Mouse Anti-IL-13 MAb 228B/C-1 VH CDR3," located at <http://score.uspto.gov/ScoreAccessWeb/getItem.htm?AppId=14934100&seqId=09323b678 . . . >, last visited on Aug. 3, 2017, 2 pages.
Office Action Appendix AXW58813, dated Apr. 29, 2010, "Human IL-17F Monoclonal Antibody Light Chain Variable Region, SEQ ID 40," located at <http://score.uspto.gov/ScoreAccessWeb/getItem.htm?AppId=14934100&seqId=09323b678 . . . >, last visited on Aug. 4, 2017, 2 pages.
Office Action Appendix AXW58867, dated Apr. 29, 2010, "Human IL-17A/F mAb Heavy Chain Variable Region CDR Mutant, SEQ ID 94," located at <http://score.uspto.gov/ScoreAccessWeb/getItem.htm?AppId=14934100&seqId=09323b678 . . . >, last visited on Aug. 3, 2017, 2 pages.
Office Action Appendix AXW58868, dated Apr. 29, 2010, "Human IL-17A/F mAb Heavy Chain Variable Region CDR Mutant, SEQ ID 95," located at <http://score.uspto.gov/ScoreAccessWeb/getItem.htm?AppId=14934100&seqId=09323b678 . . . >, last visited on Aug. 3, 2017, 2 pages.
Office Action Appendix AXW58883, dated Apr. 29, 2010, "Human IL-17F mAb Light Chain Variable Region CDR, SEQ ID 110,"

(56) References Cited

OTHER PUBLICATIONS located at <http://score.uspto.gov/ScoreAccessWeb/getItem.htm?AppId=14934100&seqId=09323b678 . . . >, last visited on Aug. 3, 2017, 2 pages.
Office Action Appendix AXW58884, dated Apr. 29, 2010, "Human IL-17F mAb Light Chain Variable Region CDR, SEQ ID 111," located at <http://score.uspto.gov/ScoreAccessWeb/getItem.htm?AppId=14934100&seqId=09323b678 . . . >, last visited on Aug. 3, 2017, 2 pages.
Office Action Appendix BBP32144, dated Dec. 4, 2014, "Human Anti-IL-13 Antibody Lebrikizumab VH Region Variant Q1E, SEQ 19," located at <http://score.uspto.gov/ScoreAccessWeb/getItem.htm?AppId=14934100&seqId=09323b678 . . . >, last visited on Aug. 3, 2017, 2 pages.
Office Action Appendix BBP32145, dated Dec. 4, 2014, "Humanized Anti-IL-13 Antibody Lebrikizumab VL Region Variant M4L, SEQ 20," located at <http://score.uspto.gov/ScoreAccessWeb/getItem.htm?AppId=14934100&seqId=09323b678 . . . >, last visited on Aug. 3, 2017, 2 pages.
Office Action Appendix BBP32165, dated Dec. 4, 2014, "Humanized Anti-IL-13 Antibody Lebrikizumab Heavy Chain, SEQ ID 40," located at <http://score.uspto.gov/ScoreAccessWeb/getItem.htm?AppId=14934100&seqId=09323b678 . . . >, last visited on Aug. 3, 2017, 3 pages.
Office Action Appendix BBP32166, dated Dec. 4, 2014, "Humanized Anti-IL-13 Antibody Lebrikizumab Light Chain, SEQ ID 41," located at <http://score.uspto.gov/ScoreAccessWeb/getItem.htm?AppId=14934100&seqId=09323b678 . . . >, last visited on Aug. 4, 2017, 2 pages.
Office Action Appendix BCD74304, dated Oct. 22, 2015, "Anti-IL-17 Antibody Heavy Chain Variable Region, SEQ ID 39," located at <http://score.uspto.gov/ScoreAccessWeb/getItem.htm?AppId=14934100&seqId=09323b678 . . . >, last visited on Aug. 4, 2017, 2 pages.
Office Action Appendix BCD74337, dated Oct. 22, 2015, "Anti-IL-17 Antibody Heavy Chain, SEQ ID 72," located at <http://score.uspto.gov/ScoreAccessWeb/getItem.htm?AppId=14934100&seqId=09323b678 . . . >, last visited on Aug. 4, 2017, 2 pages.
Office Action Appendix BCD74338, dated Oct. 22, 2015, "Anti-IL-17 Antibody Light Chain, SEQ ID 73," located at <http://score.uspto.gov/ScoreAccessWeb/getItem.htm?AppId=14934100&seqId=09323b678 . . . >, last visited on Aug. 4, 2017, 2 pages.
Office Action Appendix BCD74381, dated Oct. 22, 2015, "Anti-IL-13 Antibody Heavy Chain, Sequence ID 116," located at a http://score.uspto.gov/ScoreAccessWeb/getItem.htm?AppId=14934100&seqID=09323b678 . . .>, last visited on Aug. 7, 2017, 2 pages.
Rosano et al. "Recombinant Protein Expression in *Escherichia coli*: Advances and Challenges," *Frontiers in Microbiology* 5(Article 172):1-17, (Apr. 2014, e-pub. Apr. 17, 2014).

\* cited by examiner

Periplasm
Folding/Assembly

Folding/Assembly = Chaperones

Ppiases:
RotA
SurA
FkpA

Oxidoreductases:
DsbA
DsbC
DsbG

Chaperones:
Skp
Spy
FkpA
SurA

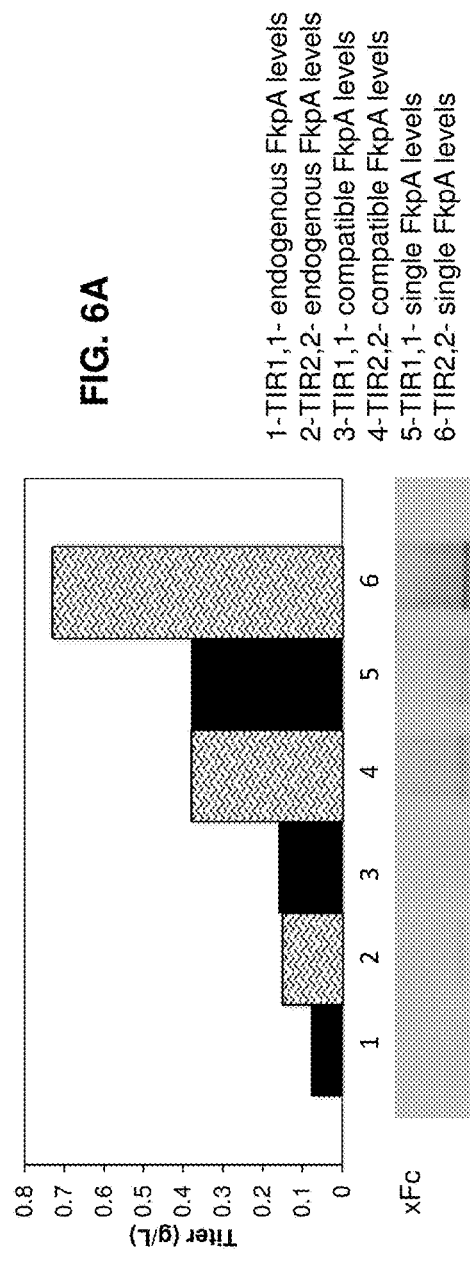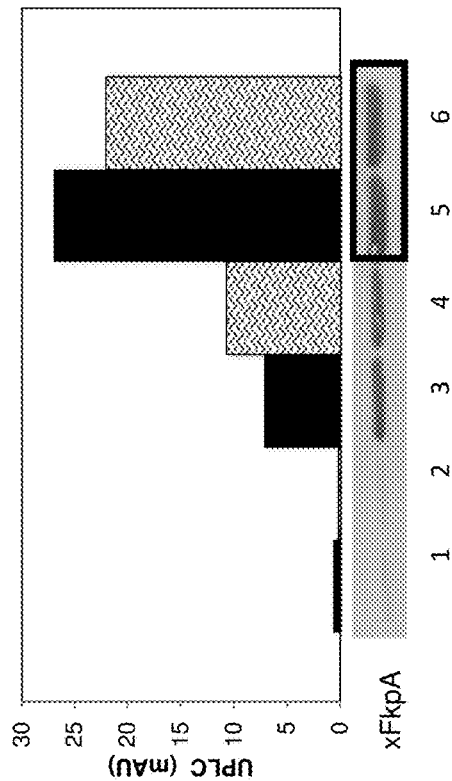
FIG. 6A
FIG. 6B

1- TIR2,2 No Chaperones
2- TIR2,2 FkpA

66F8 = ΔDegP
67A6 = +DegPS210A

Sequence of FkpA Signal Peptide Variants

Pho / Pho (TIR = 1, 1)

Chaperone Vector
pACYC

ImmTac Expression Vector
pBR322

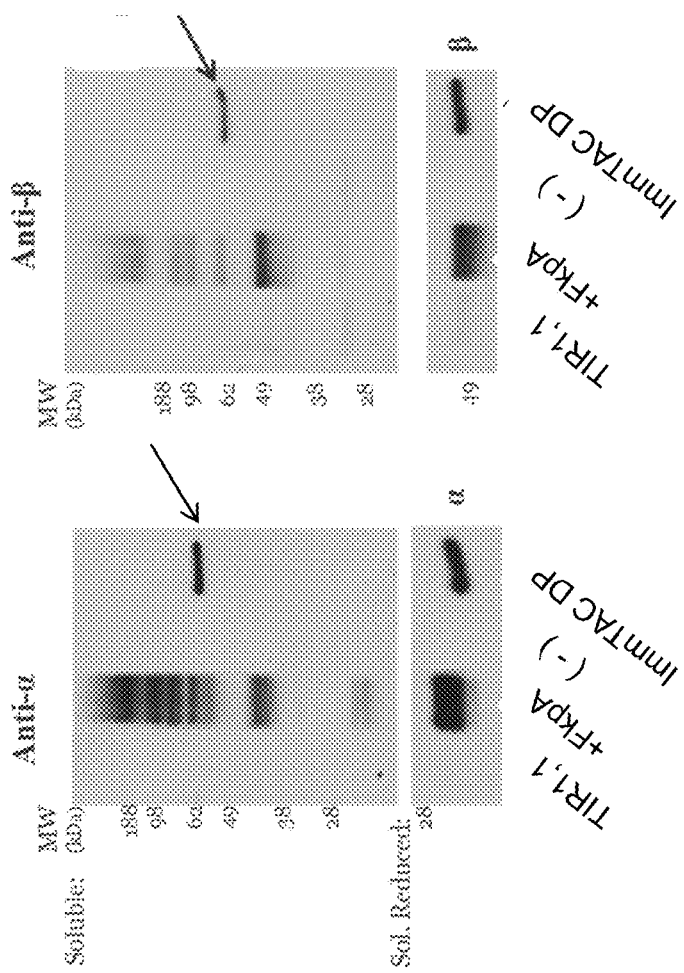
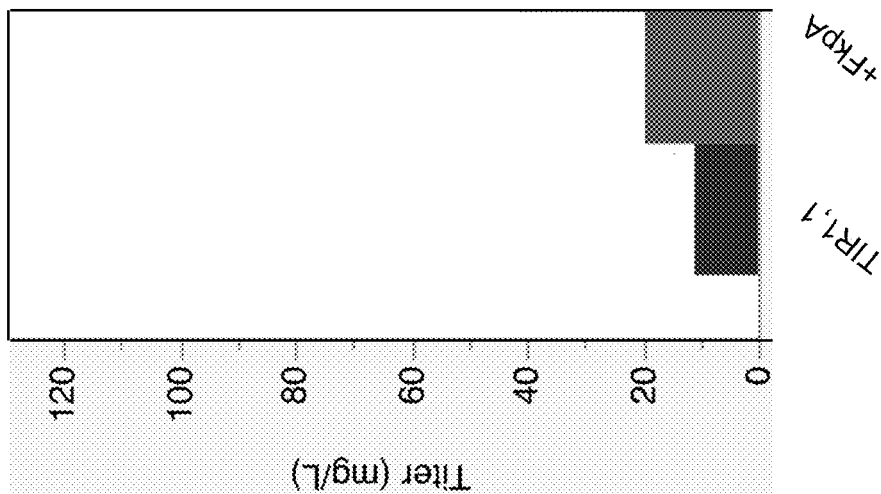
FIG. 54A
FIG. 54B

SEQUENCE LISTING

```
<160> NUMBER OF SEQ ID NOS: 4

<210> SEQ ID NO 1
<211> LENGTH: 80
<212> TYPE: DNA
<213> ORGANISM: Artificial Sequence
<220> FEATURE:
<223> OTHER INFORMATION: Synthetic Construct

<400> SEQUENCE: 1
gaattatgaa gtccctgttt aaagtgacgc tgctggcgac cacaatggcc gttgccctgc    60
atgcaccaat cacttttgct                                                80

<210> SEQ ID NO 2
<211> LENGTH: 80
<212> TYPE: DNA
<213> ORGANISM: Artificial Sequence
<220> FEATURE:
<223> OTHER INFORMATION: Synthetic Construct

<400> SEQUENCE: 2
gaattatgaa gtcgctattc aaagtgacgc tgctggcgac cacaatggcc gttgccctgc    60
atgcaccaat cacttttgct                                                80

<210> SEQ ID NO 3
<211> LENGTH: 80
<212> TYPE: DNA
<213> ORGANISM: Artificial Sequence
<220> FEATURE:
<223> OTHER INFORMATION: Synthetic Construct

<400> SEQUENCE: 3
gaattatgaa gtcgctgttt aaagttacgc tgctggcgac cacaatggcc gttgccctgc    60
atgcaccaat cacttttgct                                                80
```

```
<210> SEQ ID NO 4
<211> LENGTH: 25
<212> TYPE: PRT
<213> ORGANISM: Artificial Sequence
<220> FEATURE:
<223> OTHER INFORMATION: Synthetic Construct

<400> SEQUENCE: 4

Met Lys Ser Leu Phe Lys Val Thr Leu Leu Ala Thr Thr Met Ala Val
1               5                   10                  15

Ala Leu His Ala Pro Ile Thr Phe Ala
            20                  25
```

US 10,066,002 B2

METHODS OF PRODUCING TWO CHAIN PROTEINS IN BACTERIA

CROSS REFERENCE TO RELATED APPLICATION(S)

This application claims the benefit of U.S. Provisional Application No. 62/075,798, filed Nov. 5, 2014, which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392035100SEQLIST.TXT, date recorded: Nov. 5, 2015, size: 2 KB).

FIELD

This disclosure relates to methods of producing recombinant polypeptides, such as immune mobilizing monoclonal T-cell receptor against cancer (ImmTAC) proteins. More specifically, this disclosure relates to methods of producing heterologous secretory proteins in bacteria through utilization of optimized expression vectors and culture processes.

BACKGROUND

Recombinant protein production in prokaryotic host cells has been a source of many important therapeutic agents since the production of human insulin in *E. coli* in 1978. As molecular biology tools and knowledge has advanced, the complexity of recombinant therapeutics has also increased. Production of these recombinant proteins requires that the products exhibit properties such as proper translation, folding, assembly, disulfide bonding, and transport to the periplasm. It is known that expression of many recombinant proteins, particularly those with disulfide bonds (e.g., two chain proteins, including without limitation antibodies and antibody fragments), leads to the formation of inclusion bodies in prokaryotic host cells (Spadiut et al., Trends in Biotechnology, 32:54, 2014). Accordingly, there is a demand for expression systems and processes for the recombinant production of properly folded and assembled two chain proteins in prokaryotic host cells on an industrial scale.

Monoclonal antibodies represent one of the fastest growing types of recombinant therapeutic agent, with numerous monoclonal antibodies already approved or under review for sf-3593591 the treatment of various diseases (Nelson et al., Nature Review Drug Discovery, 9:767, 2010). Traditional monoclonal antibodies bind a single target antigen. For many diseases, it may be advantageous to employ antibodies that bind more than one target antigen, i.e., multispecific antibodies. Such antibodies can be employed in combinatorial approaches directed against multiple therapeutic targets (see, e.g., Bostrom et al., Science 323:1610, 2009; and Wu et al., Nature Biotechnology, 25:1290, 2007). For instance, bispecific antibodies can be produced that simultaneously bind an epitope expressed on the surface of a cancer cell and an epitope expressed on a T cell to induce T cell-mediated killing of tumor cells (Shalaby et al., Clinical Immunology, 74:185, 1995).

The use of bispecific antibodies in the clinic requires the ability to produce two chain proteins in industrially relevant amounts. While vector components that improve recombinant protein production in prokaryotic host cells have been described (see, e.g., Schlapschy et al., Protein Engineering, Design and Selection, 19:385, 2006; and Simmons et al., Journal of Immunological Methods 263: 133, 2002), the results described herein demonstrate that modifications to expression vectors alone do not solve all of the production problems encountered during the manufacture of two chain proteins. There remains a need for optimal methods for efficiently producing recombinant two chain proteins, such as antibody fragments and half-antibodies, on a preparative scale.

All references cited herein, including patent applications, patent publications, and UniProtKB/Swiss-Prot Accession numbers are herein incorporated by reference in their entirety, as if each individual reference were specifically and individually indicated to be incorporated by reference.

SUMMARY

In one aspect, provided herein are methods of producing a polypeptide comprising two chains in a prokaryotic host cell, the method comprising: (a) culturing the host cell to express the two chains of the polypeptide, whereby upon expression the two chains fold and assemble to form a biologically active polypeptide in the host cell; wherein the host cell comprises a polynucleotide comprising (1) a first translational unit encoding a first chain of the polypeptide; (2) a second translational unit encoding a second chain of the polypeptide; and (3) a third translational unit encoding at least one chaperone protein selected from the group consisting of peptidyl-prolyl isomerases, protein disulfide oxidoreductases, and combinations thereof; wherein the host cell is cultured in a culture medium under conditions comprising: a growth phase comprising a growth temperature and a growth agitation rate, and a production phase comprising a production temperature and a production agitation rate, wherein the growth temperature is from 2 to 10° C. above the production temperature, and the growth agitation rate is from 50 to 250 rpm above the production agitation rate; and (b) recovering the biologically active polypeptide from the host cell. Also provided are methods of producing an immune mobilizing monoclonal T-cell receptor against cancer (ImmTAC) comprising a T-cell receptor (TCR) alpha chain and a TCR beta chain in a prokaryotic host cell, the methods comprising: (a) culturing the host cell to express the TCR alpha chain and the TCR beta chain of the ImmTAC in a culture medium under conditions comprising: a growth phase comprising a growth temperature and a growth agitation rate, and a production phase comprising a production temperature and a production agitation rate, whereby upon expression the TCR alpha chain and the TCR beta chain fold and assemble to form a biologically active ImmTAC in the host cell; wherein the host cell comprises a polynucleotide comprising (1) a first translational unit encoding the TCR alpha chain of the ImmTAC; (2) a second translational unit encoding the TCR beta chain of the ImmTAC; and (3) a third translational unit encoding at least one chaperone protein selected from the group consisting of peptidyl-prolyl isomerases, protein disulfide oxidoreductases, and combinations thereof; wherein the growth temperature is from 2 to 10° C. above the production temperature, and the growth agitation rate is from 50 to 250 rpm above the production agitation rate; and (b) recovering the biologically active ImmTAC from the host cell. Also provided are methods of producing a polypeptide comprising two chains in a prokaryotic host cell, the method comprising: (a) culturing the host cell to express the two chains of the polypeptide, whereby upon expression the two chains fold and assemble to form a biologically active polypeptide in the host cell; wherein the host cell comprises a polynucleotide comprising: (1) a first translational unit encoding a first chain of the polypeptide; (2) a second translational unit encoding a second chain of the polypeptide; (3) a third translational unit encoding a first chaperone protein; (4) a fourth translational unit encoding a second chaperone protein; and (5) a fifth translational unit encoding a third chaperone protein, wherein the first, second and third chaperone proteins are selected from the group consisting of peptidyl-prolyl isomerases, protein disulfide oxidoreductases, and combinations thereof; wherein the host cell is cultured in a culture medium under conditions comprising: a growth phase comprising a growth temperature and a growth agitation rate, and a production phase comprising a production temperature and a production agitation rate, wherein the growth temperature is from 2 to 10° C. above the production temperature, and the growth agitation rate is from 50 to 250 rpm above the production agitation rate; and (b) recovering the biologically active polypeptide from the host cell. Also provided are methods of producing an immune mobilizing monoclonal T-cell receptor against cancer (ImmTAC) comprising a T-cell receptor (TCR) alpha chain and a TCR beta chain in a prokaryotic host cell, the methods comprising: (a) culturing the host cell to express the TCR alpha chain and the TCR beta chain of the ImmTAC in a culture medium under conditions comprising: a growth phase comprising a growth temperature and a growth agitation rate, and a production phase comprising a production temperature and a production agitation rate, whereby upon expression the TCR alpha chain and the TCR beta chain fold and assemble to form a biologically active ImmTAC in the host cell; wherein the host cell comprises a polynucleotide comprising: (1) a first translational unit encoding the TCR alpha chain of the ImmTAC; (2) a second translational unit encoding the TCR beta chain of the ImmTAC; (3) a third translational unit encoding a first chaperone protein; (4) a fourth translational unit encoding a second chaperone protein; and (5) a fifth translational unit encoding a third chaperone protein, wherein the first, second and third chaperone proteins are selected from the group consisting of peptidyl-prolyl isomerases, protein disulfide oxidoreductases, and combinations thereof; wherein the growth temperature is from 2 to 10° C. above the production temperature, and the growth agitation rate is from 50 to 250 rpm above the production agitation rate; and (b) recovering the biologically active ImmTAC from the host cell. In some embodiments, the polypeptide comprises three, four or five chains. In some embodiments, pH of the culture medium is maintained at a pH in the range of between 6.7 and 7.3 during the production phase. In some embodiments, the polynucleotide further comprises three copies of a promoter, wherein a first copy is in operable combination with the first translational unit, a second copy is in operable combination with the second translational unit, and a third copy is in operable combination with the third translational unit to drive transcription of the first chain, the second chain and the chaperone protein. In some embodiments, two of the translational units encoding two of the three chaperone proteins are part of a single transcriptional unit (bicistronic unit). In some embodiments, the polynucleotide further comprises a promoter in operable combination with each translational unit. In some embodiments, the promoter is an inducible promoter. In some embodiments, the inducible promoter is an IPTG-inducible promoter that drives transcription of the first chain, the second chain and the chaperone protein in the absence of IPTG induction. In some embodiments, the inducible promoter is an IPTG-inducible promoter that drives transcription of the TCR alpha chain, the TCR beta chain and the chaperone protein in the absence of IPTG induction. In some embodiments, the inducible promoter is a Pho promoter that drives transcription of the first chain, the second chain and the chaperone protein when phosphate in the culture medium has been depleted. In some embodiments, the inducible promoter is a Pho promoter that drives transcription of the TCR alpha chain, the TCR beta chain and the chaperone protein when phosphate in the culture medium has been depleted. In some embodiments, the polynucleotide further comprises a selectable marker and the culture medium comprises a selection agent consisting of a single antibiotic to cause the host cell to retain the polynucleotide. In some embodiments, the first translational unit comprises a first translation initiation region (TIR) in operable combination with a coding region of the first chain, and the second translational unit comprises a second translation initiation region (TIR) in operable combination with a coding region of the second chain, wherein the relative translation strength of the first and second TIR is from about 1.0 to about 3.0. In some embodiments, the first translational unit comprises a first translation initiation region (TIR) in operable combination with a coding region of the TCR alpha chain, and the second translational unit comprises a second translation initiation region (TIR) in operable combination with a coding region of the TCR beta chain, wherein the relative translation strength of the first and second TIR is from about 1.0 to about 3.0. In some embodiments, the at least one chaperone protein, or the first chaperone protein comprises a peptidyl-prolyl isomerase. In some embodiments, the peptidyl-prolyl isomerase is an FkpA protein. In some embodiments, the FkpA is E. coli FkpA. In some embodiments, the at least one chaperone protein further comprises or one or both of the second chaperone protein and the third chaperone protein comprises a protein disulfide oxidoreductase. In some embodiments, the protein disulfide oxidoreductase is one or both of a DsbA protein and a DsbC protein. In some embodiments, the at least one protein disulfide oxidoreductase is one or both of E. coli DsbA and E. coli DsbC. In some embodiments, the prokaryotic host cell is a gram-negative bacterium. In some embodiments, the gram-negative bacterium is E. coli. In some embodiments, the E. coli is of a strain deficient in endogenous protease activity. In some embodiments, the E. coli is a strain with a degpS210A mutation. In some embodiments, the E. coli is a strain with a genotype of W3110 ΔfhuA ΔphoA ilvG2096 (Val$^r$) Δprc spr43H1 ΔdegP ΔmanA lacI$^Q$ ΔompT ΔmenE degpS210A. In some embodiments, the polypeptide is heterologous to the host cell. In some embodiments, the polypeptide is a monomer of a heterodimer (e.g., bispecific antibody). In some embodiments, the TCR alpha chain comprises a TCR alpha chain variable domain and a TCR alpha chain constant domain, and the TCR beta chain comprises a TCR beta chain variable domain and a TCR beta chain constant domain. In some embodiments, the two chains of the polypeptide are linked to each other by at least one disulfide bond. In some embodiments, the two chains of the ImmTAC are linked to each other by at least one disulfide bond. In some embodiments, the ImmTAC further comprises an antibody fragment that binds a T cell and activates a T cell response. In some embodiments, the antibody fragment comprises an anti-CD3 single chain antibody fragment. In some embodiments, the ImmTAC comprises a TCR engineered to possess increased affinity for an antigen, as compared to affinity for the antigen of TCR that has not been engineered. In some embodiments, the two chains of the polypeptide are linked to each other by a polypeptide linker. In some embodiments, the polypeptide is a monovalent antibody in which the first chain and the second chain comprise an immunoglobulin heavy chain and an immunoglobulin light chain. In some embodiments, the immunoglobulin heavy chain is an IgG1 or an IgG4 isotype. In some embodiments, the monovalent antibody is capable of specifically binding an antigen. In some embodiments, the antigen is a cytokine. In some embodiments, the cytokine is selected from the group consisting of a chemokine, an interferon, an interleukin, a lymphokine, and tumour necrosis factor. In some embodiments, the growth factor is a vascular endothelial growth factor. In some embodiments, the antigen is selected from the group consisting of IL-4, IL13, IL-14, IL-17, VEGFA and VEGFC. In some embodiments, the polypeptide is a secretory protein recovered from the periplasm of the host cell. In some embodiments, the ImmTAC is recovered from the periplasm of the host cell. In some embodiments, the polypeptide is an immune mobilizing monoclonal T-cell receptor against cancer (ImmTAC) comprising a soluble affinity enhanced T cell receptor fused to an anti-CD3 single-chain variable fragment (scFv). In some embodiments, the growth temperature is in the range of about 30° C. to about 34° C. during the growth phase, and the production temperature in the range of about 25° C. to about 29° C. during the production phase. In some embodiments, the growth agitation rate is in the range of about 600 to 800 rpm during the growth phase, and the production agitation rate is in the range of about 300 to about 500 rpm during the production phase. In some embodiments, the growth agitation rate is sufficient to achieve an oxygen uptake rate in the host cell during the growth phase of from 0.5 to 2.5 mmol/L/min above a peak oxygen uptake rate in the host cell during the production phase. In some embodiments, the peak oxygen uptake rate of the host cell during the growth phase is in the range of 3.5 to 4.5 mmol/L/min, and the oxygen uptake rate of the host cell during the production phase is in the range of 1.0 to 3.0 mmol/L/min. In some embodiments, the growth agitation rate is from about 10% to about 40% (rpm/rpm) higher than the production agitation rate.

It is to be understood that one, some, or all of the properties of the various embodiments described herein may be combined to form other embodiments of the present disclosure. These and other aspects of the disclosure will become apparent to one of skill in the art. These and other embodiments of the disclosure are further described by the detailed description that follows.

BRIEF DESCRIPTION OF THE DRAWINGS

FIG. 1A provides a graph of total subunits for LCs and HCs produced from TIR1,1 (black bars) and TIR2,2 (striped bars) production vectors, as measured by RP-HPLC. FIG. 1B provides a graph of total subunits produced for LC and HC (black bars) or soluble LC and HC (gray bars) from the TIR1,1 production vectors. FIG. 1C provides a graph of total subunits produced for total LC and HC (black bars) or soluble LC and HC (gray bars) from the TIR2,2 production vectors.

FIG. 3A is a schematic depicting bacterial protein production, illustrating the folding and assembly of proteins in the periplasm using chaperones. FIG. 3B is a list of chaperone proteins, including peptidyl-prolyl isomerases ("Ppiases"), oxidoreducatases, and other chaperones.

FIG. 5A depicts a Western blot showing hAb and soluble monomeric heavy chain accumulation upon expression of different levels of FkpA, while a Coomassie-stained gel shows total soluble protein production under each condition. FIG. 5B A graph shows the titer of hAb produced upon expression of different levels of FkpA.

FIG. 6A-B shows the production of the xIL13 IgG4 hAb upon expression of different levels of FkpA. FIG. 6A provides a graph showing the titer of the xIL13 hAb produced using different vector systems, and is accompanied by a Western blot showing hAb and soluble monomeric heavy chain accumulation in each condition. FIG. 6B provides a graph showing the amount of FkpA produced using different vector systems, and is accompanied by a Western blot showing expression of FkpA in each condition. In both panels, "endogenous FkpA levels" refers to bacterial host cells that do not contain a plasmid encoding FkpA; "compatible FkpA levels" refers to expression of xIL13 and FkpA from separate (compatible) plasmids; and "single FkpA levels" refers to a single vector expressing both xIL13 and FkpA.

FIG. 7A depicts a Western blot showing hAb and soluble monomeric heavy chain accumulation. FIG. 7B provides a graph showing the titer of the xIL4 hAb produced using inducible expression of FkpA, and is accompanied by a Western blot showing expression of FkpA. In both panels, sample 1 uses a TIR1,1 vector for the production of the xIL4 hAb and does not overexpress FkpA; sample 2 uses a TIR2,2 vector for the production of the xIL4 hAb and does not overexpress FkpA; sample 3 uses TIR1,1 to produce the xIL4 hAb and IPTG to induce FkpA expression; and sample 4 uses TIR2,2 to produce the xIL4 hAb and IPTG to induce FkpA expression.

FIG. 8A provides a graph showing the titer of the xVEGFC hAb produced using different vector systems. FIG. 8B depicts a gel showing total soluble protein production under both conditions, with FkpA bands as labeled. FIG. 8C depicts a Western blot showing accumulation of the xVEGFC hAb and soluble monomeric heavy chain. In panels all panels, sample 1 uses a TIR2,2 vector for the production of the xVEGFC hAb and does not contain a plasmid for expression of FkpA; sample 2 uses a TIR2,2 vector for the production of the xIL4 hAb and IPTG to induce FkpA expression.

FIG. 12A depicts a Western blot showing accumulation of the xIL4 hAb and soluble monomeric heavy chain under various conditions. FIG. 12B provides a graph showing the titer of the xIL4 hAb produced under various conditions, and is accompanied by a Western blot showing expression of FkpA.

FIG. 42 provides the nucleotide sequence of the TIR1 (SEQ ID NO:1), TIR2 (SEQ ID NO:2) and TIR3 (SEQ ID NO:3) FkpA signal sequence variants. Single nucleotide substitutions were made in the third position of specific codons and represent synonymous codon changes that do not alter the amino acid sequence of the FkpA signal peptide sequence (SEQ ID NO:4).

FIG. 47A shows a plot of the accumulation of the xIL13 hAb in fermentations performed with FkpA TIR variants. FIG. 47B shows the level of FkpA present in the soluble fraction from the xIL13 hAb process at the end of the fermentation.

FIG. 54A shows the soluble and soluble reduced anti-alpha and anti-beta Western blots for the following conditions: without chaperones (TIR1,1), with FkpA (+FkpA), negative control (−), and the ImmTAC 1 positive control (ImmTAC DP). The arrow designates the assembled ImmTac. FIG. 54B shows the final titers for the TIR1,1 alone and TIR1,1 with FkpA conditions.

DETAILED DESCRIPTION

Figure 1A:
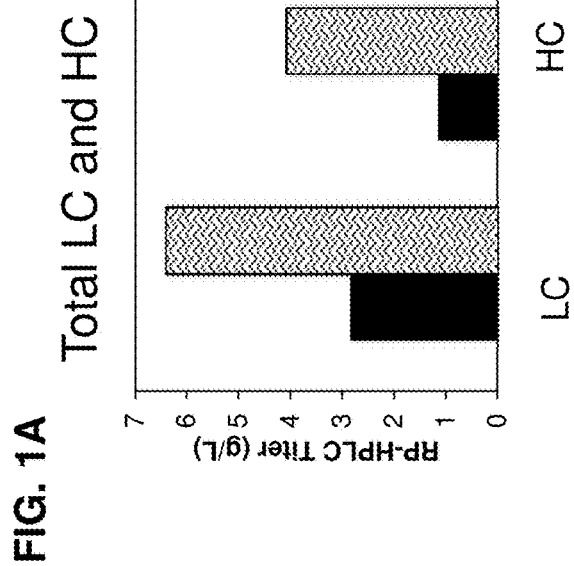
FIG. 1A-C shows the production of total light chain (LC) and heavy chain (HC) subunits from the xIL13 half-antibody (hAb) production vector.

The examples provided herein demonstrate that co-expression of one or more specific chaperone proteins in combination with translational units encoding each chain of a multiple chain protein (e.g., light chain and heavy chain of a half-antibody) increases the production of an assembled multiple chain protein in a prokaryotic host cell system. The examples further demonstrate that subsequent process improvements, such as specific temperatures and agitation rates for certain phases of the fermentation, result in significant enhancements in production and robustness beyond the expression vector improvements. Overall, the methods described herein achieve an at least 10-fold gain in production of exemplary two chain polypeptides (e.g., half antibody).

In one aspect, provided herein are methods of producing a polypeptide containing two chains in a prokaryotic host cell by culturing the host cell to express the two chains of the polypeptide, where upon expression the two chains fold and assemble to form a biologically active polypeptide in the host cell; where the host cell contains a polynucleotide including (1) a first translational unit encoding a first chain of the polypeptide; (2) a second translational unit encoding a second chain of the polypeptide; and (3) a third translational unit encoding at least one chaperone protein selected from peptidyl-prolyl isomerases, protein disulfide oxidoreductases, and combinations thereof; where the host cell is cultured in a culture medium under conditions including: a growth phase including a growth temperature and a growth agitation rate, and a production phase including a production temperature and a production agitation rate, where the growth temperature is from 2 to 10° C. above the production temperature, and the growth agitation rate is from 50 to 250 rpm above the production agitation rate; and (b) recovering the biologically active polypeptide from the host cell. In one aspect the polypeptide consists of two chains, while in another aspect the polypeptide comprises three, four, five or more chains.

In another aspect, provided herein are methods of producing a polypeptide containing two chains in a prokaryotic host cell by culturing the host cell to express the two chains of the polypeptide, where upon expression the two chains fold and assemble to form a biologically active polypeptide in the host cell; where the host cell contains a polynucleotide including (1) a first translational unit encoding a first chain of the polypeptide; (2) a second translational unit encoding a second chain of the polypeptide; (3) a third translational unit encoding a first chaperone protein; (4) a fourth translational unit encoding a second chaperone protein; and (5) a fifth translational unit encoding a third chaperone protein, where the first, second, and third chaperone proteins are selected from peptidyl-prolyl isomerases, protein disulfide oxidoreductases, and combinations thereof; where the host cell is cultured in a culture medium under conditions including: a growth phase including a growth temperature and a growth agitation rate, and a production phase including a production temperature and a production agitation rate, where the growth temperature is from 2 to 10° C. above the production temperature, and the growth agitation rate is from 50 to 250 rpm above the production agitation rate; and (b) recovering the biologically active polypeptide from the host cell. In one aspect the polypeptide consists of two chains, while in another aspect the polypeptide comprises three, four, five or more chains.

I. Definitions

Before describing the disclosure in detail, it is to be understood that this disclosure is not limited to particular compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se. At a maximum, the term "about" as used herein in reference to a value, encompasses from 90% to 110% of that value (e.g., relative translation strength of a first and second TIR of about 1.0 to about 3.0 refers to a relative translation strength in the range of between 0.9 and 3.3).

It is understood that aspects and embodiments of the disclosure described herein include "comprising," "consisting," and "consisting essentially of" aspects and embodiments.

The term "polypeptide comprising two chains," (the terms "two chain protein" and "two chain polypeptide" may also be used interchangeably herein), as used herein is intended to refer to any polypeptide containing more than one distinct polypeptide chain. In some embodiments, a two chain protein may include a macromolecular complex of two or more polypeptides linked together through one or more intermolecular linkages, including without limitation a disulfide bond. In some embodiments, a two chain protein may include a single polypeptide with amino acid sequences belonging to two distinct polypeptide chains (e.g., an antibody heavy chain and an antibody light chain) linked by a polypeptide linker. In this case, a two chain protein may physically represent a single chain, but two or more portions of the single chain may functionally behave as if they are two separate protein chains. For example, a single chain antibody may include a functional heavy chain and a functional light chain that, while joined by a polypeptide linker, nonetheless fold and assemble as if they were separate polypeptides associated only by intermolecular linkages (e.g., one or more disulfide bonds).

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

The term "cistron," as used herein, is intended to refer to a genetic element broadly equivalent to a translational unit comprising the nucleotide sequence coding for a polypeptide chain and adjacent control regions. A "cistron" may include, for example, one or more open-reading frames, a translational initiation region (TIR; as defined herein below), a signal sequence and a termination region.

A "polycistronic" expression vector refers to a single vector that contains and expresses multiple cistrons under the regulatory control of one single promoter. A common example of polycistronic vector is a "dicistronic" vector that contains and expresses two different polypeptides under the control of one promoter. Upon expression of a dicistronic or polycistronic vector, multiple genes are first transcribed as a single transcriptional unit, and then translated separately.

A "transcriptional unit" refers to a polynucleotide that is transcribed as a single RNA transcript. A "translational unit" refers to a segment of a polynucleotide that encodes and, when translated, produces a polypeptide. As described above, a polycistronic polynucleotide may contain a single transcriptional unit with multiple translational units.

A "separate cistron" expression vector according to the present disclosure refers to a single vector comprising at least two separate promoter-cistron pairs, wherein each cistron is under the control of its own promoter. Upon expression of a separate cistron expression vector, both transcription and translation processes of different genes are separate and independent.

A "chaperone protein" as used herein refers to any protein that aids in the folding or assembly of other macromolecules, including without limitation two chain proteins. Generally, chaperone proteins may act by many different mechanisms to promote protein folding or assembly. For example, chaperone proteins may promote protein folding and/or assembly, catalyze the formation of intrachain disulfide bonds, promote protein un-folding and/or disassembly (e.g., of aggregated or misfolded proteins or multiprotein complexes), prevent aggregation, aid in protein degradation, and so forth.

The "translation initiation region" or TIR or translational initiation region or translational initiation sequence, as used herein refers to a nucleic acid region providing the efficiency of translational initiation of a gene of interest. In general, a TIR within a particular cistron encompasses the ribosome binding site (RBS) and sequences 5' and 3' to RBS. The RBS is defined to contain, minimally, the Shine-Dalgarno region and the start codon (AUG). Accordingly, a TIR also includes at least a portion of the nucleic acid sequence to be translated. Preferably, a TIR of the disclosure includes a secretion signal sequence encoding a signal peptide that precedes the sequence encoding for the light or heavy chain within a cistron. A TIR variant contains sequence variants (particularly substitutions) within the TIR region that alter the property of the TIR, such as its translational strength as defined herein below. Preferably, a TIR variant of the disclosure contains sequence substitutions within the first 2 to about 14, preferably about 4 to 12, more preferably about 6 codons of the secretion signal sequence that precedes the sequence encoding for the light or heavy chain within a cistron.

The term "translational strength" as used herein refers to a measurement of a secreted polypeptide in a control system wherein one or more variants of a TIR is used to direct secretion of a polypeptide and the results compared to the wild-type TIR or some other control under the same culture and assay conditions. Without being limited to any one theory, "translational strength" as used herein can include, for example and without limitation, a measure of mRNA stability, efficiency of ribosome binding to the ribosome binding site, and so forth.

"Secretion signal sequence" or "signal sequence" refers to a nucleic acid sequence encoding for a short signal peptide that can be used to direct a newly synthesized protein of interest through a cellular membrane, usually the inner membrane or both inner and outer membranes of prokaryotes. As such, the protein of interest such as the immunoglobulin light or heavy chain polypeptide is secreted into the periplasm of the prokaryotic host cells or into the culture medium. The signal peptide encoded by the secretion signal sequence may be endogenous to the host cells, or they may be exogenous, including signal peptides native to the polypeptide to be expressed. Secretion signal sequences are typically present at the amino terminus of a polypeptide to be expressed, and are typically removed enzymatically between biosynthesis and secretion of the polypeptide from the cytoplasm. Thus, the signal peptide is usually not present in a mature protein product.

"Operably linked" refers to a juxtaposition of two or more components, wherein the components so described are in a relationship permitting them to function in their intended manner. For example, a promoter is operably linked to a coding sequence if it acts in cis to control or modulate the transcription of the linked sequence. Generally, but not necessarily, the DNA sequences that are "operably linked" are contiguous and, where necessary to join two protein coding regions or in the case of a secretory leader, contiguous and in the reading frame. However, although an operably linked promoter is generally located upstream of the coding sequence, it is not necessarily contiguous with it. Operably linked enhancers can be located upstream, within or downstream of coding sequences and at considerable distances from the promoter. Linking is accomplished by recombinant methods known in the art, e.g., using PCR methodology, by annealing, or by ligation at convenient restriction sites. If convenient restriction sites do not exist, then synthetic oligonucleotide adaptors or linkers are used in accord with conventional practice.

"Regulatory elements" as used herein, refer to nucleotide sequences present in cis, necessary for transcription and translation of a polynucleotide encoding a heterologous polypeptide into polypeptides. The transcriptional regulatory elements normally comprise a promoter 5' of the gene sequence to be expressed, transcriptional initiation and termination sites, and polyadenylation signal sequence. The term "transcriptional initiation site" refers to the nucleic acid in the construct corresponding to the first nucleic acid incorporated into the primary transcript, i.e., the mRNA precursor; the transcriptional initiation site may overlap with the promoter sequences.

A "promoter" refers to a polynucleotide sequence that controls transcription of a gene or sequence to which it is operably linked. A promoter includes signals for RNA polymerase binding and transcription initiation. The promoters used will be functional in the cell type of the host cell in which expression of the selected sequence is contemplated. A large number of promoters including constitutive, inducible and repressible promoters from a variety of different sources, are well known in the art (and identified in databases such as GenBank) and are available as or within cloned polynucleotides (from, e.g., depositories such as ATCC as well as other commercial or individual sources). With inducible promoters, the activity of the promoter increases or decreases in response to a signal, e.g., the presence of IPTG or phosphate depletion.

The term "host cell" (or "recombinant host cell"), as used herein, is intended to refer to a cell that has been genetically altered, or is capable of being genetically altered by introduction of an exogenous polynucleotide, such as a recombinant plasmid or vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

A "subject" or an "individual" for purposes of treatment refers to any animal classified as a mammal, including humans, domestic and farm animals, and zoo, sports, or pet animals, such as dogs, horses, cats, cows, etc. Preferably, the mammal is human.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "constant domain" refers to the portion of an immunoglobulin molecule having a more conserved amino acid sequence relative to the other portion of the immunoglobulin, the variable domain, which contains the antigen binding site. The constant domain contains the $C_H1$, $C_H2$ and $C_H3$ domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "$V_H$." The variable domain of the light chain may be referred to as "$V_L$." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any mammalian species can be assigned to one of two clearly distinct types, called kappa ("κ") and lambda ("k"), based on the amino acid sequences of their constant domains.

The term IgG "isotype" or "subclass" as used herein is meant any of the subclasses of immunoglobulins defined by the chemical and antigenic characteristics of their constant regions.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, γ, ε, γ, and μ, respectively. The subunit structures and three-dimensional configurations of different classes of immunoglobulins are well known and described generally in, for example, Abbas et al. *Cellular and Mol. Immunology*, 4th ed. (W.B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. In some embodiments, the antibody fragment described herein is an antigen-binding fragment. Examples of antibody fragments include Fab, Fab', $F(ab')_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this disclosure. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the disclosure may be made by a variety of techniques, including, for example, expression in a prokaryotic host cell, the hybridoma method (e.g., Kohler and Milstein, *Nature,* 256:495-97 (1975); Hongo et al., *Hybridoma,* 14 (3): 253-260 (1995), Harlow et al., *Antibodies: A Laboratory Manual,* (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATTZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227: 381 (1991); Marks et al., *J. Mol. Biol.,* 222:581 (1991). Also available for the preparation of human monoclonal antibodies are methods described in Cole et al., *Monoclonal Antibodies and Cancer Therapy,* Alan R. Liss, p. 77 (1985); Boerner et al., *J. Immunol.,* 147(1):86-95 (1991). See also van Dijk and van de Winkel, *Curr. Opin. Pharmacol.,* 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 103:3557-3562 (2006) regarding human antibodies generated via a human B-cell hybridoma technology.

A "species-dependent antibody" is one which has a stronger binding affinity for an antigen from a first mammalian species than it has for a homologue of that antigen from a second mammalian species. Normally, the species-dependent antibody "binds specifically" to a human antigen (e.g., has a binding affinity (Kd) value of no more than about $1\times10^{-7}$ M, preferably no more than about $1\times10^{-8}$ M and preferably no more than about $1\times10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but preferably is a humanized or human antibody.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

TABLE 1a

Antibody Hypervariable Regions

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The expression "linear antibodies" refers to the antibodies described in Zapata et al. (1995 *Protein Eng,* 8(10):1057-1062). Briefly, these antibodies comprise a pair of tandem Fd segments (VH—CH1-VH—CH1) which, together with complementary light chain polypeptides, form a pair of antigen binding regions. Linear antibodies can be bispecific or monospecific.

II. Molecular Optimization

Provided herein are methods of producing a polypeptide containing two chains in a prokaryotic host cell by culturing the host cell to express the two chains of the polypeptide, where upon expression the two chains fold and assemble to form a biologically active polypeptide in the host cell; where the host cell contains a polynucleotide including (1) a first translational unit encoding a first chain of the polypeptide; (2) a second translational unit encoding a second chain of the polypeptide; and (3) a third translational unit encoding at least one chaperone protein selected from peptidyl-prolyl isomerases, protein disulfide oxidoreductases, and combinations thereof. Also provided herein are methods of producing a polypeptide containing two chains in a prokaryotic host cell by culturing the host cell to express the two chains of the polypeptide, where upon expression the two chains fold and assemble to form a biologically active polypeptide in the host cell; where the host cell contains a polynucleotide including (1) a first translational unit encoding a first chain of the polypeptide; (2) a second translational unit encoding a second chain of the polypeptide; (3) a third translational unit encoding a first chaperone protein; (4) a fourth translational unit encoding a second chaperone protein; and (5) a fifth translational unit encoding a third chaperone protein, where the first, second, and third chaperone proteins are selected from peptidyl-prolyl isomerases, protein disulfide oxidoreductases, and combinations thereof.

In some embodiments, a host cell is cultured to express the two chains of a polypeptide, where upon expression the two chains fold and assemble to form a biologically active polypeptide in the host cell. As used herein, two chain folding and assembly may refer to any or all steps that promote the ultimate adoption of proper three-dimensional two chain protein conformation, two chain protein assembly, or both. Folding and assembly may refer to the folding and assembly of each chain into its proper conformation and folding, or it may refer to the folding and assembly of the complex created by the intermolecular linkage of two protein chains. Similarly, each chain may fold and assemble to form a biologically active polypeptide, or the complex created by the intermolecular linkage of two protein chains may fold and assemble to form, as a whole, a biologically active polypeptide.

A biologically active polypeptide may refer to any polypeptide that is able to carry out a function ascribed to the polypeptide. Functions of biologically active polypeptides may include, without limitation, proper folding or assembly, binding or other interaction with another macromolecule, and enzymatic activity. By way of illustration, a biologically active antibody may refer to an antibody that is able to carry out at least one function ascribed to antibodies, including without limitation binding to an epitope or possessing a property of an antibody Fc region, as described in further detail below.

Chaperone Proteins

In some embodiments, a polynucleotide of the present disclosure contains a translational unit encoding at least one chaperone protein. As described above, a chaperone protein may refer to any protein that aids in the folding or assembly of other macromolecules, including without limitation two chain proteins. Examples of chaperone proteins may include without limitation peptidyl-prolyl isomerases, protein disulfide oxidoreductases, and heat shock proteins (such as Hsp60, Hsp70, Hsp90, and Hsp100 proteins). Chaperone proteins may also aid in transporting proteins across membranes, e.g., translocation of polypeptide chains across the plasma membrane or endoplasmic reticulum membrane.

In some embodiments, a chaperone protein may be a peptidyl-prolyl isomerase. Peptidyl-prolyl isomerase (the terms "prolyl isomerase," "rotamase," and "PPiase" may be used interchangeably herein) may refer to any enzyme catalyzing the interconversion of cis and trans isomers of proline or prolyl-iminopeptide bonds. The EC number for this reaction is EC 5.2.1.8. Any protein known or predicted to catalyze the reaction described by this EC number may be a peptidyl-prolyl isomerase of the present disclosure. Peptidyl-prolyl isomerase activity may also be described by the GO term ID GO:0003755. Any protein known or predicted to possess the molecular function described by this GO term ID may be a peptidyl-prolyl isomerase of the present disclosure.

Peptidyl-prolyl isomerase activity is known in the art to promote protein folding and assembly. In some embodiments, peptidyl-prolyl isomerases may aid in protein folding and assembly by converting trans prolyl bonds to cis prolyl bonds for proteins whose properly folded structure includes a cis prolyl bond. Some peptidyl-prolyl isomerases are also known to enhance the folding and assembly of proteins that lack cis prolyl bonds (Bothmann H and Pluckthun A 2000 J. Biol. Chem. 275:17100). In some embodiments, peptidyl-prolyl isomerases may aid in protein folding and assembly of proteins that lack cis prolyl bonds. Thus, while peptidyl-prolyl isomerase activity may serve as a functional characteristic to identify a chaperone protein useful for the methods described herein, the utility of a peptidyl-prolyl isomerase is not necessarily limited to its catalytic activity per se.

In some embodiments, the peptidyl-prolyl isomerase is an FkpA protein. In some embodiments, the FkpA protein is $E.$ $coli$ FkpA. An $E.$ $coli$ FkpA may refer to any polypeptide encoded by an fkpA gene in any strain or isolate of bacteria belonging to the species $E.$ $coli$. In some embodiments, $E.$ $coli$ FkpA refers a protein encoded by an fkpA gene described by EcoGene Accession Number EG12900. In some embodiments, $E.$ $coli$ FkpA refers a protein having the sequence described by the NCBI RefSeq Accession Number NP_417806.

Other FkpA proteins are known in the art. Examples of FkpA proteins may include, without limitation, $S.$ $boydii$ peptidyl-prolyl isomerase (NCBI RefSeq No. WP_000838252), $C.$ $youngae$ peptidyl-prolyl isomerase (NCBI RefSeq No. WP_006687366), $K.$ $oxytoca$ peptidyl-prolyl isomerase (NCBI RefSeq No. WP_004125943), $S.$ $enterica$ peptidyl-prolyl isomerase (NCBI RefSeq No. WP_000838233), $K.$ $pneumoniae$ peptidyl-prolyl isomerase (NCBI RefSeq No. WP_019704642), $S.$ $cerevisiae$ FPR3p (NCBI RefSeq No. NP_013637), $M.$ $musculus$ Fkpb1a (NCBI RefSeq No. NP_032045), $M.$ $musculus$ Fkpb2 (NCBI RefSeq No. NP_032046), $H.$ $sapiens$ FKBP2 (NCBI RefSeq No. NP_001128680), and $D.$ $melanogaster$ CG14715 (NCBI RefSeq No. NP_650101). In some embodiments, an FkpA protein of the present disclosure has at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identity to $E.$ $coli$ FkpA.

In some embodiments, a chaperone protein may be a protein disulfide oxidoreductase. Protein disulfide oxidoreductase (the terms "protein disulfide isomerase" and "thiol-disulfide isomerase" may be used interchangeably herein) may refer to any enzyme catalyzing the rearrangement of disulfide bonds in proteins. For example, a protein disulfide oxidoreductase may catalyze the oxidation of cysteines to form disulfide bonds in proteins. A protein disulfide oxidoreductase may also catalyze the isomerization of mispaired disulfide bonds in proteins. The EC number for this reaction is EC 5.3.4.1. Any protein known or predicted to catalyze the reaction described by this EC number may be a protein disulfide oxidoreductase of the present disclosure. Protein disulfide oxidoreductase activity may also be described by the GO term ID GO:0015035. Any protein known or predicted to possess the molecular function described by this GO term ID may be a protein disulfide oxidoreductase of the present disclosure.

Protein disulfide oxidoreductase activity is known in the art to promote protein folding and assembly. For example, protein disulfide oxidoreductase activity promotes the formation of proper intramolecular and intermolecular disulfide bonds during protein folding and assembly. In particular, protein disulfide oxidoreductase activity is important for proteins with disulfide bonds that are expressed in the periplasm of prokaryotic cells.

In some embodiments, the protein disulfide oxidoreductase is a DsbA protein. In some embodiments, the DsbA protein is $E.$ $coli$ DsbA. An $E.$ $coli$ DsbA may refer to any polypeptide encoded by a dsbA gene in any strain or isolate of bacteria belonging to the species *E. coli*. In some embodiments, *E. coli* DsbA refers a protein encoded by a dsbA gene described by EcoGene Accession Number EG11297. In some embodiments, *E. coli* DsbA refers a protein having the sequence described by the NCBI RefSeq Accession Number NP_418297.

Other DsbA proteins are known in the art. Examples of DsbA proteins may include, without limitation, *S. flexneri* thiol-disulfide isomerase (NCBI RefSeq No. WP_000725335), *S. dysenteriae* thiol-disulfide isomerase (NCBI RefSeq No. WP_000725348), *C. youngae* thiol-disulfide isomerase (NCBI RefSeq No. WP_006686108), and *S. enterica* thiol-disulfide isomerase (NCBI RefSeq No. WP_023240584). In some embodiments, a DsbA protein of the present disclosure has at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identity to *E. coli* DsbA.

In some embodiments, the protein disulfide oxidoreductase is a DsbC protein. In some embodiments, the DsbC protein is *E. coli* DsbC. An *E. coli* DsbC may refer to any polypeptide encoded by a dsbC gene in any strain or isolate of bacteria belonging to the species *E. coli*. In some embodiments, *E. coli* DsbC refers a protein encoded by a dsbC gene described by EcoGene Accession Number EG11070. In some embodiments, *E. coli* DsbC refers a protein having the sequence described by the NCBI RefSeq Accession Number NP_417369.

Other DsbC proteins are known in the art. Examples of DsbC proteins may include, without limitation, *S. sonnei* protein-disulfide isomerase (NCBI RefSeq No. WP_000715206), *S. dysenteriae* protein-disulfide isomerase (NCBI RefSeq No. WP_000715209), *E. fergusonii* protein-disulfide isomerase (NCBI RefSeq No. WP_000715225), *S. bongori* thiol:disulfide interchange protein DsbC (NCBI RefSeq No. WP_020845161), and *S. enterica* protein disulfide isomerase DsbC (NCBI RefSeq No. WP_023183515). In some embodiments, a DsbC protein of the present disclosure has at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identity to *E. coli* DsbC.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 50%, typically at least 75%, and even more typically at least 80%, 85%, 90%, 95% or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted using known algorithms (e.g., by the local homology algorithm of Smith and Waterman, Adv Appl Math, 2:482, 1981; by the homology alignment algorithm of Needleman and Wunsch, J Mol Biol, 48:443, 1970; by the search for similarity method of Pearson and Lipman, Proc Natl Acad Sci USA, 85:2444, 1988; by computerized implementations of these algorithms FASTDB (Intelligenetics), BLAST (National Center for Biomedical Information), GAP, BESTFIT, FASTA, and TFASTA in the Wisconsin Genetics Software Package (Genetics Computer Group, Madison, Wis.), or by manual alignment and visual inspection.

A preferred example of an algorithm that is suitable for determining percent sequence identity and sequence similarity is the FASTA algorithm (Pearson and Lipman, Proc Natl Acad Sci USA, 85:2444, 1988; and Pearson, Methods Enzymol, 266:227-258, 1996). Preferred parameters used in a FASTA alignment of DNA sequences to calculate percent identity are optimized, BL50 Matrix 15:-5, k-tuple=2; joining penalty=40, optimization=28; gap penalty-12, gap length penalty=-2; and width=16.

Another preferred example of algorithms suitable for determining percent sequence identity and sequence similarity are the BLAST and BLAST 2.0 algorithms (Altschul et al., Nuc Acids Res, 25:3389-3402, 1977; and Altschul et al., J Mol Biol, 215:403-410, 1990, respectively). BLAST and BLAST 2.0 are used, with the parameters described herein, to determine percent sequence identity for the nucleic acids and proteins of the disclosure. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (Henikoff and Henikoff, Proc Natl Acad Sci USA, 89:10915, 1989) alignments (B) of 50, expectation (E) of 10, M=5, N=−4, and a comparison of both strands.

The BLAST algorithm also performs a statistical analysis of the similarity between two sequences (See, e.g., Karlin and Altschul, Proc Natl Acad Sci USA, 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method (Feng and Doolittle, J Mol Evol, 35:351-360, 1987), employing a method similar to a published method (Higgins and Sharp, CABIOS 5:151-153, 1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc Acids Res, 12:387-395, 1984).

Another preferred example of an algorithm that is suitable for multiple DNA and amino acid sequence alignments is the CLUSTALW program (Thompson et al., Nucl Acids. Res, 22:4673-4680, 1994). ClustalW performs multiple pairwise comparisons between groups of sequences and assembles them into a multiple alignment based on homology. Gap open and Gap extension penalties were 10 and 0.05 respectively. For amino acid alignments, the BLOSUM algorithm can be used as a protein weight matrix (Henikoff and Henikoff, Proc Natl Acad Sci USA, 89:10915-10919, 1992).

Expression Cassettes and Vectors

In some embodiments, a host cell contains a polynucleotide including (1) a first translational unit encoding a first chain of the polypeptide; (2) a second translational unit encoding a second chain of the polypeptide; and (3) a third translational unit encoding at least one chaperone protein selected from peptidyl-prolyl isomerases, protein disulfide oxidoreductases, and combinations thereof. In some embodiments, a host cell contains a polynucleotide including (1) a first translational unit encoding a first chain of the polypeptide; (2) a second translational unit encoding a second chain of the polypeptide; (3) a third translational unit encoding a first chaperone protein; (4) a fourth translational unit encoding a second chaperone protein; and (5) a fifth translational unit encoding a third chaperone protein, where the first, second, and third chaperone proteins are selected from peptidyl-prolyl isomerases, protein disulfide oxidoreductases, and combinations thereof. It is a discovery of the present disclosure that increased production of properly folded and assembled two chain proteins may be achieved using a single plasmid system (i.e., a single polynucleotide containing translational units encoding each chain of the two chain protein and one or more translational units encoding one or more chaperone proteins) or a compatible plasmid system (i.e., a first polynucleotide containing translational units encoding each chain of the two chain protein and a second polynucleotide containing one or more translational units encoding one or more chaperone proteins).

In some embodiments, the polynucleotide further contains three copies of a promoter, where a first copy is in operable combination with the first translational unit, a second copy is in operable combination with the second translational unit, and a third copy is in operable combination with the third translational unit to drive transcription of the first chain, the second chain and the chaperone protein. In some embodiments, two of the translational units encoding two of the three chaperone proteins are part of a single translational unit. In some embodiments, the polynucleotide further contains a promoter in operable combination with each translational unit.

In some embodiments, the promoter is an inducible promoter. As described above, the activity of an inducible promoter increases or decreases in response to a signal. For example, an inducible promoter may promote transcription in response to the presence of a signal, such as IPTG. An inducible promoter may promote transcription in response to the absence of a signal, such as phosphate. In either of these scenarios, the amount of transcription may or may not be proportional to the amount of signal, or the deficiency thereof. Numerous examples of inducible promoters suitable for prokaryotic host cells are known in the art. These may include, without limitation, lac, tac, trc, trp, pho, recA, tetA, nar, phage $P_L$, cspA, T7, and $P_{BAD}$ promoters (see Terpe K.

2006 Appl. Microbiol. Biotechnol. 72:211 for more detailed description). In some embodiments, three copies of an inducible promoter are used to drive expression of separate translational units, e.g., both chains of a two chain protein and a chaperone protein, in a coordinated manner.

In some embodiments, the inducible promoter is an IPTG-inducible promoter. An IPTG-inducible promoter may refer to any polynucleotide sequence that promotes transcription in a manner responsive to isopropyl β-D-1-thiogalactopyranoside (IPTG) or any other lactose derivative that is able to promote transcription from the lac operon (e.g., allolactose). Many examples of IPTG-inducible promoters are known in the art, including without limitation tac (e.g, tacI, tacII, etc.) promoters, lac promoters, and derivatives thereof (e.g., lacUV5, taclac, and so forth).

In some embodiments, the inducible promoter is an IPTG-inducible promoter that drives transcription of the first chain, the second chain and the chaperone protein. It is a surprising discovery of the present disclosure that an IPTG-inducible promoter regulating expression of a chaperone protein may, without induction by IPTG, promote expression of the chaperone protein at a level that promotes a higher product titer, as compared to expression of the chaperone protein when the IPTG-inducible promoter is induced by IPTG.

In some embodiments, the inducible promoter is a pho promoter that drives transcription of the first chain, the second chain and the chaperone protein when phosphate in the culture medium has been depleted. A pho promoter may refer to any polynucleotide sequence that promotes transcription in a manner responsive to extracellular phosphate (for example, inorganic phosphate). For example, the phosphate (Pho) regulon in *E. coli* includes protein components that sense extracellular phosphate and, in response to phosphate levels, regulate the expression of numerous downstream genes through Pho promoters (see Hsieh Y J and Wanner B L 2010 Curr. Opin. Microbiol. 13(2):198 for more detailed description). When bacteria are grown in a culture medium, expression of this Pho regulon is known to be repressed when phosphate (e.g., inorganic phosphate, Pi) is available in the medium and induced when phosphate has been depleted. One non-limiting example of a pho promoter used in the methods described herein is the *E. coli* phoA promoter. This promoter is widely known and used in the art to regulate recombinant protein expression in prokaryotic host cells in a manner dependent upon the concentration of phosphate in the cell culture medium (see Lubke C et al. 1995 Enzyme Microb. Technol. 17(10):923 for more detailed description).

In some embodiments, the polynucleotide further contains a selectable marker and the culture medium includes a selection agent with a single antibiotic to cause the host cell to retain the polynucleotide. Advantageously, the methods described herein allow the production of the chains of a two chain protein with co-expression of one or more chaperone proteins such that the translational units encoding each of these components are all included in a single polynucleotide (e.g., an expression plasmid or a single plasmid system as described herein). The advantage of such a system is that since all of these components are encoded by the same plasmid, only one selectable marker is required for the maintenance of these polynucleotides in a prokaryotic host cell.

A selectable marker may refer to any polynucleotide that encodes a protein that promotes the survival of a host cell when the cell undergoes selection, i.e., any condition used to preferentially increase the abundance of cell(s) bearing a selectable marker relative to the abundance of cell(s) lacking the selectable marker. Examples of selectable markers are genes that promote host cell survival in the presence of an antibiotic. Numerous selectable markers and corresponding selection agents with single antibiotics are known in the art. For example and without limitation, many selectable markers and corresponding antibiotics are described and cited in Jang C W and Magnuson T 2013 PLoS ONE 8(2):e57075. In some embodiments, a selectable marker may refer to a gene (e.g., a gene expressed from a plasmid) that complements a gene deletion present within the host cell's genome. In these examples, when the cell undergoes selection (i.e., growth under a condition that requires the activity of the gene deleted from the host genome), the copy of the gene supplied by the plasmid complements the deficiency of the host genome, thereby selecting for cell(s) bearing the exogenous complementing gene. Such genes may include auxotrophic markers or genes required to produce a specific nutrient lacking in a cell medium, examples of which are further described herein. Several exemplary selectable markers and antibiotics are further described below.

In some embodiments, the first translational unit includes a first translation initiation region (TIR) in operable combination with a coding region of the first chain, and the second translational unit includes a second translation initiation region (TIR) in operable combination with a coding region of the second chain. Translational initiation regions (TIRs) are known to be important for translation of recombinant proteins in prokaryotic host cells (see, e.g., Simmons LC and Yansura D G 1996 Nat. Biotechnol. 14:629 and Vimberg V et al. 2007 BMC Mol. Biol. 8:100). A TIR may determine the efficiency of translation of a translational unit. A TIR typically includes translational unit features such as the initiation codon, Shine-Dalgarno (SD) sequence, and translational enhancers. A TIR may further include a secretion signal sequence that encodes a signal peptide. The sequence and spacing between features of a TIR may regulate translational initiation efficiency.

In some embodiments, the relative translation strength of the first and second TIR is from about 1.0 to about 3.0. Described herein are vectors that include translational units encoding each chain of a two chain protein, and each translational unit may include a TIR. As used herein, "translational strength" may refer to the production of a polypeptide through translation of a translational unit. This production may depend upon a number of features, including without limitation mRNA translation, mRNA stability, efficiency of ribosomal binding to an mRNA, and the folding, assembly, and/or translocation of a polypeptide encoded thereby. Relative translational strength may refer to the production of a polypeptide encoded by a translational unit with a specific or experimental TIR, as compared to the production of a polypeptide encoded by a translational unit with a wild-type or control TIR, when both the experimental TIR and the control TIR are expressed by a similar prokaryotic host cell (e.g., same genus and species) cultured under the same conditions. Further description of TIRs may be found in U.S. Pat. No. 8,361,744.

Recombinant Polypeptides

Certain aspects of the present disclosure relate to methods of producing polypeptides with two chains. Advantageously, the methods described herein may be useful for promoting the expression, folding and assembly of many different types of proteins, particularly those with disulfide bonds, such as two chain proteins as described above. Particular two chain proteins are described below, but the methods described herein are not limited to these particular embodiments. As used herein, two chain proteins may include proteins containing more than one distinct polypeptide chain. Although many embodiments described herein involve two chain proteins with two polypeptide chains, two chain proteins with more than two polypeptide chains (e.g., three or more polypeptides) are contemplated and may be produced by the methods described herein. As described above, two chain proteins made of a single polypeptide chain that otherwise associate as they would if they were two distinct polypeptide chains (e.g., single chain antibodies, single chain variable fragments, and the like) are also contemplated and may be produced by the methods described herein.

In some embodiments, the two chains of a two chain polypeptide of the present disclosure are linked to each other by at least one disulfide bond. Disulfide bonds may refer to any covalent bond linking two thiol groups. Disulfide bonds in polypeptides typically form between the thiol groups of cysteine residues. Polypeptide disulfide bonds are known in the art to be important for the folding and assembly of many polypeptides, such as two chain proteins of the present disclosure. Polypeptide disulfide bonds may include disulfide bonds between cysteine residues in a single polypeptide chain (i.e., intramolecular or intra-chain disulfide bonds). Polypeptide disulfide bonds may also include disulfide bonds between cysteine residues found on separate polypeptide chains (i.e., intermolecular or inter-chain disulfide bonds). Therefore, in some embodiments, two chains of a two chain polypeptide are linked to each other by at least one disulfide bond.

Disulfide bonds are known in the art to be important for the folding and assembly of antibodies and antibody fragments. Different antibody isotypes, and different subclasses within an isotype, are known to possess different patterns of disulfide bonds. For example, IgG antibodies may contain 12 intra-chain disulfide bonds, one inter-chain disulfide bond between each light chain and its corresponding heavy chain, and between 2 and 11 inter-chain disulfide bonds between heavy chains, depending upon the particular IgG subclass (see Liu H and May K 2012 MAbs. 4(1):17 for more detailed description). IgM (see, e.g., Wiersma E J and Shulman M J 1995 J. Immunol. 154(10):5265), IgE (see, e.g., Helm B A et al. 1991 Eur. J. Immunol. 21(6):1543), IgA (see, e.g., Chintalacharuvu K R et al. 2002 J. Immunol. 169(9):5072), and IgD (see, e.g., Shin S U et al. 1992 Hum. Antibodies Hybridomas 3(2):65) are also known to form disulfide bonds during folding and assembly.

In some embodiments, a two chain polypeptide of the present disclosure is heterologous to the host cell. As used herein, a heterologous polypeptide when used in reference to a host cell may refer to any polypeptide that is not endogenously expressed in the host cell, i.e., when the host cell is isolated from nature. A heterologous polypeptide may also refer to a polypeptide that may be expressed endogenously by the host cell, but is expressed under different regulation than when the host cell is isolated from nature. Examples of different regulation may include without limitation a different amount of expression, expression in response to a different stimulus, or any other altered context of expression, such as by use of a heterologous promoter, such as an inducible promoter.

In some embodiments, a two chain polypeptide of the present disclosure is a monomer of a heterodimer. As used herein, a heterodimer may refer to any polypeptide complex that contains two distinct polypeptides or polypeptide complexes in operable linkage. A non-limiting example of a heterodimer is a bispecific or bivalent antibody composed of two distinct antibody monomers (i.e., a light chain-heavy chain pair in operable linkage). In this example, the folding and assembly of a first heavy chain-light chain pair recognizing a first antigen produces a first antibody monomer. The folding and assembly of a second heavy chain-light chain pair recognizing a second antigen produces a second antibody monomer. These monomers may be assembled by any means known in the art (described below in more detail with respect to bispecific antibodies) to form a heterodimer. For more details on an illustrative example of heterodimeric antibody formation, see Ridgway J B B et al. 1996 Protein Eng. 9(7):617.

In some embodiments, a two chain polypeptide of the present disclosure is a monovalent antibody in which the first chain and the second chain represent an immunoglobulin heavy chain and an immunoglobulin light chain. As used herein, a monovalent antibody may refer to any polypeptide complex made from an antibody heavy chain and an antibody light chain operably linked together to form a heavy chain-light chain pair in which the heavy chain-light chain pair is not operably linked to a second heavy chain-light chain pair. The term "half-antibody (hAb)" may be used interchangeably herein.

In some embodiments, a monovalent antibody of the present disclosure is capable of specifically binding an antigen. As used herein, the term "binds", "specifically binding an," or is "specific for" refers to measurable and reproducible interactions such as binding between a target (i.e., and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 μM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require, exclusive binding.

In some embodiments, a two chain polypeptide of the present disclosure is a secretory protein. As used herein, a secretory protein may refer to any protein that is secreted by a host cell into the host cell periplasm or extracellular milieu. A secretory protein may be a protein that is endogenously secreted by a host cell, or a secretory protein may be a protein that is not endogenously secreted by a host cell but is modified in such a way as to promote its secretion. For example, the presence of a signal sequence, typically found at the N-terminus of a polypeptide, may direct a polypeptide to the secretory pathway for secretion. Numerous signal sequences are known in the art and may be useful for promoting the secretion of a secretory protein or allowing the secretion of protein not naturally secreted by a host cell; see, e.g., Picken et al., Infect. Immun. 42:269-275 (1983); Simmons and Yansura, Nature Biotechnology 14:629-634 (1996); and Humphreys D P et al. 2000 Protein Expr. Purif. 20(2):252. One non-limiting example of a signal sequence is a heat stable enterotoxin II (STII) signal sequence.

In some embodiments, a two chain polypeptide of the present disclosure is an immune mobilizing monoclonal T-cell receptor against cancer (ImmTAC). ImmTAC may refer to a fusion protein combining an anti-CD3 single chain antibody fragment (or analogous antibody fragment that binds a T cell and activates a T cell response) with a soluble, monoclonal T-cell receptor (TCR). In some embodiments, a soluble, monoclonal TCR of an ImmTAC may be engineered to possess increased affinity for a particular antigen, as compared to the affinity for the antigen of a TCR that has not been engineered (e.g., a naturally occurring TCR). ImmTACs may be used for a number of applications, including without limitation activation of a T-cell response against a cell, such as a tumor cell, presenting the cognate antigen recognized by the ImmTAC. In some embodiments, the soluble monoclonal TCR comprises a TCR alpha chain variable domain and a TCR beta chain variable domain. In some embodiments, the soluble monoclonal TCR further comprises a TCR alpha chain constant domain and a TCR beta chain constant domain linked by a native or non-native disulfide bond. For a more detailed description of ImmTACs, see, e.g., U.S. Pat. No. 7,569,664; Liddy et al., Nat. Med. 18:908-7 (2012); and Oates and Jakobsen, OncoImmunology 2:e22891 (2013).

In some embodiments, a secretory protein of the present disclosure is recovered from the periplasm of the host cell. Periplasm is known in the art to refer to the space between the inner or cytoplasmic membrane and the outer membrane of a Gram-negative bacterial cell. Without wishing to be bound by theory, it is thought that the periplasm is an oxidizing environment that favors the formation of disulfide bonds. Therefore, it may be advantageous to localize a polypeptide with disulfide bonds as part of its properly folded and assembled structure (e.g., a two chain protein of the present disclosure) to the periplasm (see Schlapschy M et al. 2006 Protein Eng. Des. Sel. 19(8):385 for more detailed description).

Numerous methods for recovering a periplasmic protein are known in the art. One non-limiting example of large-scale purification of periplasmic proteins is described in European Patent No. EP1356052 B1 (see, e.g., Example 4). Periplasmic proteins may be recovered by extracting a periplasmic fraction from a spheroblast preparation (see, e.g., Schlapschy M et al. 2006 Protein Eng. Des. Sel. 19(8):385). Once a periplasmic extract has been generated, periplasmic proteins may be purified by any standard protein purification technique known in the art, such as affinity purification, chromatography, and the like.

Antibodies

The two chain proteins described herein may be prepared by any suitable techniques known in the art. One exemplary class of two chain proteins is the antibody. As described below, antibodies are prepared using techniques available in the art for generating antibodies, exemplary methods of which are described in more detail in the following sections. One of skill in the art will recognize that many of the methods described below may be applied to two chain proteins other than antibodies.

The antibody is directed against an antigen of interest (e.g., and without limitation, PD-L1 (such as a human PD-L1), HER2, or CD3 (such as a human CD3), IL13, IL4, VEGFC, VEGFA, and VEGF). Preferably, the antigen is a biologically important polypeptide and administration of the antibody to a mammal suffering from a disorder can result in a therapeutic benefit in that mammal.

In certain embodiments, an antibody provided herein has a dissociation constant (Kd) of ≤1 μM, ≤150 nM, ≤100 nM, ≤50 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest. The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

(i) Antigen Preparation

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

(ii) Certain Antibody-Based Methods

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies of the disclosure can be made using the hybridoma method first described by Kohler et al., *Nature*, 256:495 (1975), and further described, e.g., in Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981), and Ni, *Xiandai Mianyixue*, 26(4): 265-268 (2006) regarding human-human hybridomas. Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005). Once desired monoclonal antibodies have been isolated from hybridomas, polynucleotides encoding them may be subcloned into a prokaryotic expression vector, and antibodies may be produced by expression in a prokaryotic host cell by any of the methods described herein.

(iii) Library-Derived Antibodies

Antibodies of the disclosure may be isolated by screening combinatorial libraries for antibodies with the desired activity or activities. For example, a variety of methods are known in the art for generating phage display libraries and screening such libraries for antibodies possessing the desired binding characteristics such as the methods described in Example 3. Additional methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

(iv) Chimeric, Humanized and Human Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008). Human antibodies can be made, for example and without limitation, by expression in a prokaryotic host cell from a prokaryotic expression vector by any of the methods described herein.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

(v) Antibody Fragments

Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli,* thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See *Antibody Engineering,* ed. Borrebaeck, supra. The antibody fragment may also be a "linear antibody", e.g., as described in U.S. Pat. No. 5,641,870, for example. Such linear antibodies may be monospecific or bispecific.

(vi) Multispecific Antibodies

Multispecific antibodies have binding specificities for at least two different epitopes, where the epitopes are usually from different antigens. While such molecules normally will only bind two different epitopes (i.e. bispecific antibodies, BsAbs), antibodies with additional specificities such as trispecific antibodies are encompassed by this expression when used herein. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991).

One approach known in the art for making bispecific antibodies is the "knobs-into-holes" or "protuberance-into-cavity" approach (see, e.g., U.S. Pat. No. 5,731,168). In this approach, two immunoglobulin polypeptides (e.g., heavy chain polypeptides) each comprise an interface. An interface of one immunoglobulin polypeptide interacts with a corresponding interface on the other immunoglobulin polypeptide, thereby allowing the two immunoglobulin polypeptides to associate. These interfaces may be engineered such that a "knob" or "protuberance" (these terms may be used interchangeably herein) located in the interface of one immunoglobulin polypeptide corresponds with a "hole" or "cavity" (these terms may be used interchangeably herein) located in the interface of the other immunoglobulin polypeptide. In some embodiments, the hole is of identical or similar size to the knob and suitably positioned such that when the two interfaces interact, the knob of one interface is positionable in the corresponding hole of the other interface. Without wishing to be bound to theory, this is thought to stabilize the heteromultimer and favor formation of the heteromultimer over other species, for example homomultimers. In some embodiments, this approach may be used to promote the heteromultimerization of two different immunoglobulin polypeptides, creating a bispecific antibody comprising two immunoglobulin polypeptides with binding specificities for different epitopes.

In some embodiments, a knob may be constructed by replacing a small amino acid side chain with a larger side chain. In some embodiments, a hole may be constructed by replacing a large amino acid side chain with a smaller side chain. Knobs or holes may exist in the original interface, or they may be introduced synthetically. For example, knobs or holes may be introduced synthetically by altering the nucleic acid sequence encoding the interface to replace at least one "original" amino acid residue with at least one "import" amino acid residue. Methods for altering nucleic acid sequences may include standard molecular biology techniques well known in the art. The side chain volumes of various amino acid residues are shown in the following table. In some embodiments, original residues have a small side chain volume (e.g., alanine, asparagine, aspartic acid, glycine, serine, threonine, or valine), and import residues for forming a knob are naturally occurring amino acids and may include arginine, phenylalanine, tyrosine, and tryptophan. In some embodiments, original residues have a large side chain volume (e.g., arginine, phenylalanine, tyrosine, and tryptophan), and import residues for forming a hole are naturally occurring amino acids and may include alanine, serine, threonine, and valine.

TABLE 1b

Properties of amino acid residues

| Amino Acid | One-letter abbreviation | Mass[a] (daltons) | Volume[b] (Å$^3$) | Accessible surface area[c] (Å$^2$) |
|---|---|---|---|---|
| Alanine (Ala) | A | 71.08 | 88.6 | 115 |
| Arginine (Arg) | R | 156.20 | 173.4 | 225 |
| Asparagine (Asn) | N | 114.11 | 117.7 | 160 |
| Aspartic Acid (Asp) | D | 115.09 | 111.1 | 150 |
| Cysteine (Cys) | C | 103.14 | 108.5 | 135 |
| Glutamine (Gln) | Q | 128.14 | 143.9 | 180 |
| Glutamic Acid (Glu) | E | 129.12 | 138.4 | 190 |
| Glycine (Gly) | G | 57.06 | 60.1 | 75 |
| Histidine (His) | H | 137.15 | 153.2 | 195 |
| Isoleucine (Ile) | I | 113.17 | 166.7 | 175 |
| Leucine (Leu) | L | 113.17 | 166.7 | 170 |
| Lysine (Lys) | K | 128.18 | 168.6 | 200 |
| Methionine (Met) | M | 131.21 | 162.9 | 185 |
| Phenylalanine (Phe) | F | 147.18 | 189.9 | 210 |
| Proline (Pro) | P | 97.12 | 122.7 | 145 |
| Serine (Ser) | S | 87.08 | 89.0 | 115 |
| Threonine (Thr) | T | 101.11 | 116.1 | 140 |
| Tryptophan (Trp) | W | 186.21 | 227.8 | 255 |
| Tyrosine (Tyr) | Y | 163.18 | 193.6 | 230 |
| Valine (Val) | V | 99.14 | 140.0 | 155 |

[a]Molecular weight of amino acid minus that of water. Values from Handbook of Chemistry and Physics, 43$^{rd}$ ed. Cleveland, Chemical Rubber Publishing Co., 1961.
[b]Values from A. A. Zamyatnin, Prog. Biophys. Mol. Biol. 24: 107-123, 1972.
[c]Values from C. Chothia, J. Mol. Biol. 105: 1-14, 1975. The accessible surface area is defined in FIGS. 6-20 of this reference.

In some embodiments, original residues for forming a knob or hole are identified based on the three-dimensional structure of the heteromultimer. Techniques known in the art for obtaining a three-dimensional structure may include X-ray crystallography and NMR. In some embodiments, the interface is the CH3 domain of an immunoglobulin constant domain. In these embodiments, the CH3/CH3 interface of human IgG$_1$ involves sixteen residues on each domain located on four anti-parallel β-strands. Without wishing to be bound to theory, mutated residues are preferably located on the two central anti-parallel β-strands to minimize the risk that knobs can be accommodated by the surrounding solvent, rather than the compensatory holes in the partner CH3 domain. In some embodiments, the mutations forming corresponding knobs and holes in two immunoglobulin polypeptides correspond to one or more pairs provided in the following table.

TABLE 2

Exemplary sets of corresponding knob-and hole-forming mutations

| CH3 of first immunoglobulin | CH3 of second immunoglobulin |
|---|---|
| T366Y | Y407T |
| T366W | Y407A |
| F405A | T394W |
| Y407T | T366Y |
| T366Y: F405A | T394W: Y407T |
| T366W: F405W | T394S: Y407A |
| F405W: Y407A | T366W: T394S |
| F405W | T394S |

Mutations are denoted by the original residue, followed by the position using the Kabat numbering system, and then the import residue (all residues are given in single-letter amino acid code). Multiple mutations are separated by a colon.

In some embodiments, an immunoglobulin polypeptide comprises a CH3 domain comprising one or more amino acid substitutions listed in Table 2 above. In some embodiments, a bispecific antibody comprises a first immunoglobulin polypeptide comprising a CH3 domain comprising one or more amino acid substitutions listed in the left column of Table 2, and a second immunoglobulin polypeptide comprising a CH3 domain comprising one or more corresponding amino acid substitutions listed in the right column of Table 2.

Following mutation of the DNA as discussed above, polynucleotides encoding modified immunoglobulin polypeptides with one or more corresponding knob- or hole-forming mutations may be expressed and purified using standard recombinant techniques and cell systems known in the art. See, e.g., U.S. Pat. Nos. 5,731,168; 5,807,706; 5,821,333; 7,642,228; 7,695,936; 8,216,805; U.S. Pub. No. 2013/0089553; and Spiess et al., Nature Biotechnology 31: 753-758, 2013. Modified immunoglobulin polypeptides may be produced using prokaryotic host cells, such as E. coli. Corresponding knob- and hole-bearing immunoglobulin polypeptides may be expressed in host cells in co-culture and purified together as a heteromultimer, or they may be expressed in single cultures, separately purified, and assembled in vitro. In some embodiments, two strains of bacterial host cells (one expressing an immunoglobulin polypeptide with a knob, and the other expressing an immunoglobulin polypeptide with a hole) are co-cultured using standard bacterial culturing techniques known in the art. In some embodiments, the two strains may be mixed in a specific ratio, e.g., so as to achieve equal expression levels in culture. In some embodiments, the two strains may be mixed in a 50:50, 60:40, or 70:30 ratio. After polypeptide expression, the cells may be lysed together, and protein may be extracted. Standard techniques known in the art that allow for measuring the abundance of homo-multimeric vs. hetero-multimeric species may include size exclusion chromatography. In some embodiments, each modified immunoglobulin polypeptide is expressed separately using standard recombinant techniques, and they may be assembled together in vitro. Assembly may be achieved, for example, by purifying each modified immunoglobulin polypeptide, mixing and incubating them together in equal mass, reducing disulfides (e.g., by treating with dithiothreitol), concentrating, and reoxidizing the polypeptides. Formed bispecific antibodies may be purified using standard techniques including cation-exchange chromatography and measured using standard techniques including size exclusion chromatography. For a more detailed description of these methods, see Speiss et al., *Nat Biotechnol* 31:753-8, 2013. In some embodiments, modified immunoglobulin polypeptides may be expressed separately in CHO cells and assembled in vitro using the methods described above.

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is typical to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. One interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al, *J. Immunol*, 152:5368 (1994).

Another technique for making bispecific antibody fragments is the "bispecific T cell engager" or BiTE® approach (see, e.g., WO2004/106381, WO2005/061547, WO2007/042261, and WO2008/119567). This approach utilizes two antibody variable domains arranged on a single polypeptide. For example, a single polypeptide chain includes two single chain Fv (scFv) fragments, each having a variable heavy chain ($V_H$) and a variable light chain ($V_L$) domain separated by a polypeptide linker of a length sufficient to allow intramolecular association between the two domains. This single polypeptide further includes a polypeptide spacer sequence between the two scFv fragments. Each scFv recognizes a different epitope, and these epitopes may be specific for different cell types, such that cells of two different cell types are brought into close proximity or tethered when each scFv is engaged with its cognate epitope. One particular embodiment of this approach includes a scFv recognizing a cell-surface antigen expressed by an immune cell, e.g., a CD3 polypeptide on a T cell, linked to another scFv that recognizes a cell-surface antigen expressed by a target cell, such as a malignant or tumor cell.

As it is a single polypeptide, the bispecific T cell engager may be expressed using any prokaryotic cell expression system known in the art. However, specific purification techniques (see, e.g., EP1691833) may be necessary to separate monomeric bispecific T cell engagers from other multimeric species, which may have biological activities other than the intended activity of the monomer. In one exemplary purification scheme, a solution containing secreted polypeptides is first subjected to a metal affinity chromatography, and polypeptides are eluted with a gradient of imidazole concentrations. This eluate is further purified using anion exchange chromatography, and polypeptides are eluted using with a gradient of sodium chloride concentrations. Finally, this eluate is subjected to size exclusion chromatography to separate monomers from multimeric species.

Antibodies with more than two valencies are contemplated. For example, trispecific antibodies can be prepared. Tuft et al. *J. Immunol.* 147: 60 (1991).

In some embodiments, the two chain protein is a part of a multispecific antibody or a bispecific antibody. A multispecific antibody or a bispecific antibody may contain two or more monovalent antibodies of the present disclosure.

In some embodiments, the first antigen binding domain of the bispecific antibody comprises one or more heavy chain constant domains, wherein the one or more heavy chain constant domains are selected from a first CH1 ($CH1_1$) domain, a first CH2 ($CH2_1$) domain, a first CH3 ($CH3_1$) domain; and the second antigen binding domain of the bispecific antibody comprises one or more heavy chain constant domains, wherein the one or more heavy chain constant domains are selected from a second CH1 ($CH1_2$) domain, second CH2 ($CH2_2$) domain, and a second CH3 ($CH3_2$) domain. In some embodiments, at least one of the one or more heavy chain constant domains of the first antigen binding domain is paired with another heavy chain constant domain of the second antigen binding domain. In some embodiments, the $CH3_1$ and $CH3_2$ domains each comprise a protuberance or cavity, and wherein the protuberance or cavity in the $CH3_1$ domain is positionable in the cavity or protuberance, respectively, in the $CH3_2$ domain. In some embodiments, the $CH3_1$ and $CH3_2$ domains meet at an interface between said protuberance and cavity. Examplary sets of amino acid substitutions in $CH3_1$ and $CH3_2$ domains are shown in Table 2 herein. In some embodiments, the $CH2_1$ and $CH2_2$ domains each comprise a protuberance or cavity, and wherein the protuberance or cavity in the $CH2_1$ domain is positionable in the cavity or protuberance, respectively, in the $CH2_2$ domain. In some embodiments, the $CH2_1$ and $CH2_2$ domains meet at an interface between said protuberance and cavity. In some embodiments, the $CH3_1$ and/or $CH3_2$ domain of an IgG contain one or more amino acid substitutions at residues selected from the group consisting of 347, 349, 350, 351, 366, 368, 370, 392, 394, 395, 398, 399, 405, 407, and 409 according to the amino acid numbering as shown in FIG. 5 of the U.S. Pat. No. 8,216,805. In some embodiments, the protuberance comprises one or more introduced residues selected from the group consisting of arginine (R) residue, phenylalanine (F) residue, tyrosine (Y) residue, and tryptophan (W) residue. In some embodiments, the cavity comprises one or more introduced residues selected from the group consisting of alanine (A) residue, serine (S) residue, threonine (T) residue, and valine (V) residue. In some embodiments, the CH3 and/or CH2 domains are from an IgG (e.g., IgG1 subtype, IgG2 subtype, IgG2A subtype, IgG2B subtype, IgG3, subtype, or IgG4 subtype). In some embodiments, one CH3 domain of the bispecific antibody comprises amino acid substitution T366Y, and the other CH3 domain comprises amino acid substitution Y407T. In some embodiments, one CH3 domain comprises amino acid substitution T366W, and the other CH3 domain comprises amino acid substitution Y407A. In some embodiments, one CH3 domain comprises amino acid substitution F405A, and the other CH3 domain comprises amino acid substitution T394W. In some embodiments, one CH3 domain comprises amino acid substitutions T366Y and F405A, and the other CH3 domain comprises amino acid substitutions T394W and Y407T. In some embodiments, one CH3 domain comprises amino acid substitutions T366W and F405W, and the other CH3 domain comprises amino acid substitutions T394S and Y407A. In some embodiments, one CH3 domain comprises amino acid substitutions F405W and Y407A, and the other CH3 domain comprises amino acid substitutions T366W and T394S. In some embodiments, one CH3 domain comprises amino acid substitution F405W, and the other CH3 domain comprises amino acid substitution T394S. The mutations are denoted by the original residue, followed by the position using the Kabat numbering system, and then the import residues. See also numbering in FIG. 5 of U.S. Pat. No. 8,216,805.

(vii) Single-Domain Antibodies

In some embodiments, an antibody of the disclosure is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

(viii) Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

(ix) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 3

Exemplary Substitutions.

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
 a. hydrophobic: Norleucine, Met, Ala, Val, Leu, Ile;
 b. neutral hydrophilic: Cys, Ser, Thr, Asn, Gln;
 c. acidic: Asp, Glu;
 d. basic: His, Lys, Arg;
 e. residues that influence chain orientation: Gly, Pro;
 f. aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

(x) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the disclosure contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues). In an exemplary embodiment, the antibody comprising the following amino acid substitutions in its Fc region: S298A, E333A, and K334A, In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.)). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature* 322:738-40 (1988); U.S. Pat. No. 5,648,260; U.S. Pat. No. 5,624,821; and WO 94/29351 concerning other examples of Fc region variants.

(xi) Antibody Derivatives

The antibodies of the disclosure can be further modified to contain additional nonproteinaceous moieties that are known in the art and readily available. In certain embodiments, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

(xii) Vectors, Host Cells, and Recombinant Methods

Antibodies may also be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(a) Signal Sequence Component

An antibody of the disclosure may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (e.g., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, lpp, or heat-stable enterotoxin II leaders.

(b) Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of prokaryotic host cells. For example, the origin of replication from the plasmid pBR322 is suitable for most Gram-negative bacteria.

(c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another selection scheme uses a prokaryotic host cell with a chromosomal deletion removing a gene whose gene product is essential for growth in a particular culture medium. In these examples, those cells that are successfully transformed with a heterologous gene that complements the chromosomal deletion of the host cell will survive when grown in the particular culture medium. Examples of genes useful in this schemes may include auxotrophic marker genes or other genes that are required to generate an essential nutrient when the host cell is grown in a particular culture medium.

(d) Promoter Component

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding an antibody.

(e) Translation Initiation Region Component

As described above, translational initiation regions (TIRs) are known to be important for translation of recombinant proteins in prokaryotic host cells (see, e.g., Simmons L C and Yansura D G 1996 Nat. Biotechnol. 14:629 and Vimberg V et al. 2007 BMC Mol. Biol. 8:100). A TIR may determine the efficiency of translation of a translational unit. A TIR typically includes translational unit features such as the initiation codon, Shine-Dalgarno (SD) sequence, and translational enhancers. A TIR may further include a secretion signal sequence that encodes a signal peptide. The sequence and spacing between features of a TIR may regulate translational initiation efficiency. For further descriptions of the uses of TIRs in protein production, see, e.g., U.S. Pat. No. 5,840,523 (Simmons et al.), which describes translation initiation region (TIR) and signal sequences for optimizing expression and secretion.

(f) Transcription Termination Component

Expression vectors used in prokaryotic host cells may also contain sequences necessary for the termination of transcription and for stabilizing the mRNA. In prokaryotic cells, terminators may include Rho-dependent or Rho-independent terminators. One example of a terminator useful in prokaryotic host cells includes without limitation the λt0 terminator (Scholtissek and Grosse, Nucleic Acids Res. 15:3185, 1987).

III. Process Optimization

Provided herein are methods of producing a polypeptide containing two chains in a prokaryotic host cell by culturing the host cell to express the two chains of the polypeptide, where upon expression the two chains fold and assemble to form a biologically active polypeptide in the host cell, wherein the host cell is cultured in a culture medium under conditions including: a growth phase including a growth temperature and a growth agitation rate, and a production phase including a production temperature and a production agitation rate, where the growth temperature is from 2 to 10° C. above the production temperature, and the growth agitation rate is from 50 to 250 rpm above the production agitation rate. It is a surprising discovery of the present disclosure that certain production process optimizations have a dramatic increase in the yield of two chain proteins, as demonstrated by the data described herein.

(g) Selection and Transformation of Host Cells

Certain aspects of the present disclosure relate to prokaryotic host cells. Suitable prokaryotes for cloning or expressing the DNA in the vectors herein include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In some embodiments, the prokaryotic host cell is a gram-negative bacterium. Gram-negative bacterium refers to any bacterium that contains an outer membrane surrounding the peptidoglycan layer detected by Gram staining. Many gram-negative bacterial host cells are known in the art. For example, gram-negative bacteria are known to include without limitation proteobacteria, such as Alphaproteobacteria, Betaproteobacteria, Gammaproteobacteria, Zetaproteobacteria, Epsilonproteobacteria, Deltaproteobacteria, and Acidobacteria; cyanobacteria; and spirochaetes. Well known gram-negative bacteria may include species from genera such as *Eschericia*, *Salmonella*, *Shigella*, *Pseudomonas*, *Heliobacter*, *Legionella*, *Neisseria*, and *Klebsiella*.

In some embodiments, a gram-negative bacterium of the present disclosure is *E. coli*. As used herein, *E. coli* may refer to any strain or isolate of bacteria belonging to the species *E. coli*. *E. coli* may include naturally occurring strains or strains that have been genetically modified, such as by mutation or transformation with a plasmid as described herein.

In some embodiments, an *E. coli* of the present disclosure is of a strain deficient in endogenous protease activity. Without wishing to be bound to theory, it is thought that strains deficient in endogenous protease activity may allow for enhanced production of recombinant proteins, such as periplasmic proteins of the present disclosure, because some endogenous proteases have activity against recombinantly expressed substrates (see Baneyx F and Georgiu G 1990 J. Bacteriol. 172(1):491 for one such example). Strains deficient in endogenous protease activity may include strains in which a gene encoding an endogenous protease is mutated, deleted, or otherwise inactivated. Examples of such genes may include, without limitation, degP, prc, and ompT. Methods for introducing mutations in a wide variety of prokaryotic host cells (e.g., for engineering strains deficient in endogenous protease activity) are well known in the art; see, e.g., Snyder L et al. 2013 Molecular Genetics of Bacteria 4$^{th}$ ed. ASM Press).

Two chain proteins such as full length antibody, antibody fusion proteins, and antibody fragments can be produced in bacteria, in particular when glycosylation and Fc effector function are not needed, such as when the therapeutic antibody is conjugated to a cytotoxic agent (e.g., a toxin) that by itself shows effectiveness in tumor cell destruction. Full length antibodies have greater half-life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, *Methods in Molecular Biology*, Vol. 248 (B. K. C. Lo, ed., Humana Press, Totowa, N.J., 2003), pp. 245-254, describing expression of antibody fragments in *E. coli*. After expression, the antibody may be isolated from the *E. coli* cell paste in a soluble fraction and can be purified through, e.g., a protein A or G column depending on the isotype. Final purification can be carried out similar to the process for purifying antibody expressed e.g., in CHO cells.

Host cells are transformed with the above-described expression or cloning vectors for two chain protein production and cultured in conventional nutrient media modified as appropriate for inducing promoters, selecting transformants, or amplifying the genes encoding the desired sequences.

(h) Culturing the Host Cells

Certain aspects of the present disclosure relate to culturing a host cell in a culture medium under conditions including a growth phase and a production phase. Each of these phases may further refer to conditions under which the host cell is grown during the particular phase. For example, as used herein, a growth phase may include a growth temperature and a growth agitation rate, and a production phase may include a production temperature and a production agitation rate.

A growth phase may refer to any time during which a culture of host cells is exponentially growing. Growth temperature as used herein may refer to the temperature of a culture medium containing a host cell of the present disclosure during a growth phase of the host cell. A growth phase of a host cell culture may be determined by methods commonly known in the art, e.g., by measuring the optical density of the culture (e.g., at a wavelength of about 550 nm, about 600 nm, or a wavelength in between) over time and determining at what time the exponential growth phase ceases. If a host cell contains a vector with a pho promoter, a growth phase may refer to any time during which a culture of host cells is exponentially growing and the concentration of phosphate in the culture medium is sufficient to prevent the induction of pho promoter-mediated gene transcription.

A production phase may refer to any time during which a culture of host cells is producing a product. Production temperature as used herein may refer to the temperature of a culture medium containing a host cell of the present disclosure during a production phase of the host cell. If a host cell contains a vector with a pho promoter driving expression of a product, a production phase may refer to any time during which the concentration of phosphate in the culture medium is sufficiently low to induce pho promoter-mediated product gene transcription.

In some embodiments, a host cell of the present disclosure is cultured at a growth temperature from 2° C. to 10° C. above the production temperature. In some embodiments, a host cell of the present disclosure is cultured at a growth temperature 2° C., 3° C., 4° C., 5° C., 6° C., 7° C., 8° C., 9° C., or 10° C. above the production temperature. In some embodiments, the growth temperature is above the production temperature by less than about any of the following amounts (in ° C.): 10, 9.5, 9, 8.5, 8, 7.5, 7, 6.5, 6, 5.5, 5, 4.5, 4, 3.5, 3, or 2.5. In some embodiments, the growth temperature is above the production temperature by greater than about any of the following amounts (in ° C.): 2, 2.5, 3, 3.5, 4, 4.5, 5, 5.5, 6, 6.5, 7, 7.5, 8, 8.5, 9, or 9.5. That is, the growth temperature is above the production temperature by any of a range of amounts (in ° C.) having an upper limit of 10, 9.5, 9, 8.5, 8, 7.5, 7, 6.5, 6, 5.5, 5, 4.5, 4, 3.5, 3, or 2.5 and an independently selected lower limit of 2, 2.5, 3, 3.5, 4, 4.5, 5, 5.5, 6, 6.5, 7, 7.5, 8, 8.5, 9, or 9.5, wherein the lower limit is less than the upper limit.

In some embodiments, the growth temperature is in the range of about 30° C. to about 34° C. during the growth phase. In some embodiments, the growth temperature is about 30° C., about 30.5° C., about 31° C., about 31.5° C., about 32° C., about 32.5° C., about 33° C., about 33.5° C., or about 34° C. during the growth phase. In some embodiments, the growth temperature during the growth phase is less than about any of the following temperatures (in ° C.): 34, 33.5, 33, 32.5, 32, 31.5, 31, or 30.5. In some embodiments, the growth temperature during the growth phase is greater than about any of the following temperatures (in ° C.): 30, 30.5, 31, 31.5, 32, 32.5, 33, or 33.5. That is, the growth temperature during the growth phase can be any of a range of temperatures (in ° C.) having an upper limit of 34, 33.5, 33, 32.5, 32, 31.5, 31, or 30.5 and an independently selected lower limit of 30, 30.5, 31, 31.5, 32, 32.5, 33, or 33.5, wherein the lower limit is less than the upper limit.

In some embodiments, the production temperature is in the range of about 25° C. to about 29° C. during the production phase. In some embodiments, the production temperature is about 25° C., about 25.5° C., about 26° C., about 26.5° C., about 27° C., about 27.5° C., about 28° C., about 28.5° C., or about 29° C. during the production phase. In some embodiments, the production temperature during the production phase is less than about any of the following temperatures (in ° C.): 29, 28.5, 28, 27.5, 27, 26.5, 26, or 25.5. In some embodiments, the production temperature during the production phase is greater than about any of the following temperatures (in ° C.): 25, 25.5, 26, 26.5, 27, 27.5, 28, or 28.5. That is, the production temperature during the production phase can be any of a range of temperatures (in ° C.) having an upper limit of 29, 28.5, 28, 27.5, 27, 26.5, 26, or 25.5 and an independently selected lower limit of 25, 25.5, 26, 26.5, 27, 27.5, 28, or 28.5, wherein the lower limit is less than the upper limit.

An agitation rate refers to the rate at which a cell culture is agitated (e.g., by shaking). Growth agitation rate as used herein may refer to the rate at which a culture containing a host cell of the present disclosure is agitated during a growth phase of the host cell. Production agitation rate as used herein may refer to the rate at which a culture containing a host cell of the present disclosure is agitated during a production phase of the host cell. Cell cultures may be agitated to maintain aeration of the cell culture.

In some embodiments, a host cell of the present disclosure is cultured at a growth agitation rate from 50 to 250 rpm above the production agitation rate. In some embodiments, a host cell of the present disclosure is cultured at a growth agitation rate of 50 rpm, 75 rpm, 100 rpm, 125 rpm, 150 rpm, 175 rpm, 200 rpm, 225 rpm, or 250 rpm above the production agitation rate. In some embodiments, the growth agitation rate is above the production agitation rate by less than about any of the following rates (in rpm): 250, 225, 200, 175, 150, 125, 100, or 75. In some embodiments, the growth agitation rate is below the production agitation rate by greater than about any of the following rates (in rpm): 50, 75, 100, 125, 150, 175, 200, or 225. That is, the growth agitation rate is above the production agitation rate by any of a range of rates (in rpm) having an upper limit of 250, 225, 200, 175, 150, 125, 100, or 75 and an independently selected lower limit of 50, 75, 100, 125, 150, 175, 200, or 225, wherein the lower limit is less than the upper limit.

In some embodiments, the growth agitation rate is in the range of about 600 to 800 rpm during the growth phase. In some embodiments, the growth agitation rate is about 600 rpm, about 625 rpm, about 650 rpm, about 675 rpm, about 700 rpm, about 725 rpm, about 750 rpm, about 775 rpm, or about 800 rpm during the growth phase. In some embodiments, the growth agitation rate is less than about any of the following rates (in rpm): 800, 775, 750, 725, 700, 675, 650, or 625. In some embodiments, the growth agitation rate is greater than about any of the following rates (in rpm): 600, 625, 650, 675, 700, 725, 750, or 775 during the growth phase. That is, the growth agitation rate during the growth phase is any of a range of rates (in rpm) having an upper limit of 800, 775, 750, 725, 700, 675, 650, or 625 and an independently selected lower limit of 600, 625, 650, 675, 700, 725, 750, or 775, wherein the lower limit is less than the upper limit.

In some embodiments, the production agitation rate is in the range of about 300 to 500 rpm during the production phase. In some embodiments, the production agitation rate during the production phase is about 300 rpm, about 325 rpm, about 350 rpm, about 375 rpm, about 400 rpm, about 425 rpm, about 450 rpm, about 475 rpm, or about 500 rpm. In some embodiments, the production agitation rate during the production phase is less than about any of the following rates (in rpm): 500, 475, 450, 425, 400, 375, 350, or 325. In some embodiments, the production agitation rate during the production phase is greater than about any of the following rates (in rpm): 300, 325, 350, 375, 400, 425, 450, or 475. That is, the production agitation rate during the production phase is any of a range of rates (in rpm) having an upper limit of 500, 475, 450, 425, 400, 375, 350, or 325 and an independently selected lower limit of 300, 325, 350, 375, 400, 425, 450, or 475, wherein the lower limit is less than the upper limit.

Without wishing to be bound to theory, it is thought that when oxygen concentration is limited, the oxygen transfer rate (OTR) is equal to the oxygen uptake rate (OUR) or metabolic rate of the cells. Manipulation of the OTR may be facilitated by adjusting the agitation rate, thus manipulating the OUR. More detailed description of OUR and its relationship to OTR may be found in Ochoa-Garcia et al., Biotechnol. Adv. 27:153, 2009. Techniques for measuring the OUR of a cell culture are known in the art and include, without limitation, using a mass spectrometer to monitor the composition of the off-gas from the cell culture and calculating the oxygen uptake and carbon dioxide evolution rates of the cell culture.

In some embodiments, a host cell of the present disclosure is cultured at a growth agitation rate sufficient to achieve an oxygen uptake rate in the host cell during the growth phase of from 0.5 to 2.5 mmol/L/min above a peak oxygen uptake rate in the host cell during the production phase. It is a discovery of the present disclosure that decreasing the agitation rate of a cell culture during the production phase to a rate sufficient to achieve an oxygen uptake rate in the host cell less than about 2.5 mmol/L/min as compared to the growth phase greatly enhances the production of a product, such as a two chain polypeptide of the present disclosure.

In some embodiments, a host cell of the present disclosure is cultured at a growth agitation rate sufficient to achieve an oxygen uptake rate in the host cell during the growth phase of 0.5 mmol/L/min, 1.0 mmol/L/min, 1.5 mmol/L/min, 2.0 mmol/L/min, or 2.5 mmol/L/min above a peak oxygen uptake rate in the host cell during the production phase. In some embodiments, a host cell of the present disclosure is cultured at a growth agitation rate sufficient to achieve an oxygen uptake rate in the host cell during the growth phase of less than about any of the following oxygen uptake rates (in mmol/L/min) above a peak oxygen uptake rate in the host cell during the production phase: 2.5, 2.0, 1.5, or 1.0. In some embodiments, a host cell of the present disclosure is cultured at a growth agitation rate sufficient to achieve an oxygen uptake rate in the host cell during the growth phase of greater than about any of the following oxygen uptake rates (in mmol/L/min) above a peak oxygen uptake rate in the host cell during the production phase: 0.5, 1.0, 1.5, 2.0, or 2.5. That is, a host cell of the present disclosure is cultured at a growth agitation rate sufficient to achieve an oxygen uptake rate in the host cell during the growth phase of any of a range of oxygen uptake rates (in in mmol/L/min) having an upper limit of 2.5, 2.0, 1.5, or 1.0 and an independently selected lower limit of 0.5, 1.0, 1.5, 2.0, or 2.5 above a peak oxygen uptake rate in the host cell during the production phase, wherein the lower limit is less than the upper limit.

In some embodiments, the peak oxygen uptake rate of the host cell during the growth phase is in the range of 3.5 mmol/L/min to 4.5 mmol/L/min. In some embodiments, the peak oxygen uptake rate of the host cell during the growth phase is 3.5 mmol/L/min, 3.75 mmol/L/min, 4.0 mmol/L/min, 4.25 mmol/L/min, or 4.5 mmol/L/min. In some embodiments, the oxygen uptake rate of the host cell during the production phase is in the range of 1.0 mmol/L/min to 3.0 mmol/L/min. In some embodiments, the oxygen uptake rate of the host cell during the production phase is 1.0 mmol/L/min, 1.25 mmol/L/min, 1.5 mmol/L/min, 1.75 mmol/L/min, 2.0 mmol/L/min, 2.25 mmol/L/min, 2.5 mmol/L/min, 2.75 mmol/L/min, or 3.0 mmol/L/min.

In some embodiments, a host cell of the present disclosure is cultured at a growth agitation rate from about 10% to about 40% (rpm/rpm) higher than the production agitation rate. In some embodiments, the host cell is cultured at a growth agitation rate that has a lower limit of at least 10%, 15%, 20%, 25%, 30%, or 35% (rpm/rpm) and an independently selected upper limit of no more than 40%, 35%, 30%, 25%, 20%, or 15% (rpm/rpm) of a production agitation rate. In a preferred embodiment, a host cell of the present disclosure is cultured in a 10 L fermentor at 1 bar back pressure and an aeration rate of 20 L/min.

Host cells of the present disclosure may be cultured in a variety of media. "Culture medium" as used herein refers to any composition or broth that supports the growth of the bacteria of the present disclosure. Suitable culture media may be liquid or solid and contain any nutrients, salts, buffers, elements, and other compounds that support the growth and viability of cells. Common nutrients of a culture medium may include sources of nitrogen, carbon, amino acids, carbohydrates, trace elements, vitamins, and minerals. These nutrients may be added as individual components (as in a defined culture medium) or as constituents of a complex extract (for example, yeast extract). A culture medium may be nutrient-rich to support rapid growth or minimal to support slower growth. A culture medium may also contain any agent used to inhibit the growth of or kill contaminating organisms (e.g., an antibiotic). A culture medium may also contain any compound used to control the activity of an inducible promoter or enzyme (as one example, IPTG may be included to induce expression of any polynucleotides controlled by a lac operon or functionally similar promoter). Many examples of suitable culture media are well known in the art and include without limitation M9 medium, Lysogeny Broth (LB), Terrific Broth (TB), NZY broth, SOB medium, and YT broth.

Any of these media may be supplemented as necessary with salts (such as sodium chloride, calcium, magnesium, and phosphate), buffers (such as HEPES), nucleotides (such as adenosine and thymidine), antibiotics, antimycotics, trace elements (defined as inorganic compounds usually present at final concentrations in the micromolar range), glucose, and/or an appropriate energy source. Typical ingredients found in a prokaryotic cell culture medium include yeast extract, salts (e.g, NaCl), tryptone, buffers (e.g., phosphate buffer), glycerol, and so forth. Any other necessary supplements may also be included at appropriate concentrations that would be known to those skilled in the art. The culture conditions, such as temperature, pH, and the like, are those previously used with the prokaryotic host cell selected for expression, and will be apparent to the ordinarily skilled artisan.

(i) Purification of Biologically Active Polypeptide

Certain aspects of the present disclosure relate to recovering a biologically active polypeptide from a host cell. Typically recovering (the terms "purifying" or "purification" may be used interchangeably herein) a biologically active polypeptide of the present disclosure involves isolating the polypeptide from the host cell (or cell culture medium if the polypeptide is excreted into the medium) and purifying the polypeptide from other associated macromolecules, e.g., cellular debris and other polypeptides. Numerous techniques for purifying a variety of proteins from a variety of host cell compartments are known in the art (see, e.g., Evans, Jr., TC and Xu M Q (eds.) Heterologous Gene Expression in *E. coli* (2011) Methods in Molecular Biology Vol 705, Humana Press). Exemplary techniques are described below, but these are included for illustrative purposes only to supplement the understanding of the skilled artisan and are in no way meant to be limiting.

When using recombinant techniques, two chain proteins such as secretory proteins can be produced intracellularly, in the periplasmic space, or directly secreted into the medium. If the secretory protein is produced intracellularly, as a first step, the particulate debris, either host cells or lysed fragments, are removed, for example, by centrifugation or ultrafiltration.

In some embodiments, the secretory protein is recovered from the periplasm of the host cell. Carter et al., *Bio/Technology* 10:163-167 (1992) describe a procedure for isolating secretory proteins which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the secretory protein is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The secretory protein composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps. With regard to antibodies, the suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered. One of skill in the art will recognize that many of these techniques useful for antibody recovery may readily be applied to recover other two chain proteins, such as secretory proteins.

In general, various methodologies for preparing antibodies for use in research, testing, and clinical are well-established in the art, consistent with the above-described methodologies and/or as deemed appropriate by one skilled in the art for a particular antibody of interest.

EXAMPLES

The disclosure will be more fully understood by reference to the following examples. They should not, however, be construed as limiting the scope of the disclosure. It is understood that the examples and embodiments described herein are for illustrative purposes only and that various modifications or changes in light thereof will be suggested to persons skilled in the art and are to be included within the spirit and purview of this application and scope of the appended claims.

Abbreviations: Ab (antibody), hAb (half antibody), HC (heavy chain), ImmTAC (immune mobilizing monoclonal T-cell receptor against cancer), IPTG (isopropyl β-D-1-thiogalactopyranoside), LC (light chain), OD (optical density), ORF (open reading frame), OTR (oxygen transfer rate), OUR (oxygen uptake rate), Tg (growth temperature), Tp (production temperature), TIR (translation initiation region), xIL4 (anti-interleukin-4), xIL13 (anti-interleukin-13), xIL17 (anti-interleukin-17), and xIL33 (anti-interleukin-33).

Example 1: Effect of Chaperone and Oxidoreductase Levels on Half-Antibody Production Titer The production of heterologous secreted proteins using recombinant techniques is important for many therapeutic molecules. Multispecific antibodies (e.g., bispecific antibodies) are one non-limiting example of heterologous secreted proteins with many important therapeutic uses, such as immunotherapy in cancer and other applications. Producing multispecific antibodies for therapeutic use requires the ability to produce the building blocks of these antibodies, such as half-antibodies (hAbs), on an industrial scale. To meet this demand, described herein are optimized expression vectors and process steps that yield significant increases in production over standard methods. Importantly, it was found that a single plasmid or a compatible plasmid system for co-expressing the heavy chain (HC) and light chain (LC) of the hAb in combination with chaperone proteins FkpA, DsbA, and DsbC significantly enhances production of the assembled hAb. This system was tested and found to improve the production of multiple hAbs, demonstrating its wide utility for the production of many secreted proteins. Subsequent optimization of process steps (including, e.g., agitation rate, pH, FkpA promoter, and culture temperature at different phases of culturing) resulted in even further significant increases in product yield.

Materials and Methods

Half-Antibody (hAb) Vector Construction

Vectors were constructed in a similar fashion to those described in EP1356052. In particular, various expression vectors were made for the expression of hAbs. For each vector, an expression cassette was cloned into the framework of the E. coli plasmid pBR322 at the EcoRI site (Sutcliffe, Cold Spring Harbor Symp. Quant. Biol. 43:77-90, 1978). Each expression cassette contained at least the following components: (1) a phoA promoter for the control of transcription (Kikuchi et al., Nucleic Acids Res. 9:5671-5678, 1981); (2) a Shine-Dalgarno sequence from the E. coli trp, the heat stable enterotoxin II (STII) signal sequence, or a combination of both for translation initiation (Chang et al., Gene 55:189-196, 1987); and (3) a λt0 terminator to end transcription (Scholtissek and Grosse, Nucleic Acids Res. 15:3185, 1987). Additionally, the STII signal sequence or silent codon variants of that signal sequence preceded the coding sequence for the light or heavy chain. This sequence directs the secretion of the polypeptide into the periplasm (Picken et al., Infect. Immun. 42:269-275, 1983; and Simmons and Yansura, Nature Biotechnology 14:629-634, 1996).

Vectors with separate cistrons were designed to provide independent expression of the immunoglobulin light and heavy chain genes. In such vectors, the cistron unit for each chain is under the control of its own PhoA promoter and is followed by a λt0 terminator. Furthermore, each cistron incorporated the TIR (translation initiation region) to modulate expression of both light and heavy chains (Simmons et al., J. Immunol. Meth., 263:133-147, 2002). In an exemplary embodiment, the expression cassette contains, from 5' to 3', a first PhoA promoter followed by the cistron for light chain (TIR-L+Light Chain) and the first λt0 terminator, and a second PhoA promoter followed by the cistron for heavy chain (TIR-H+Heavy Chain) and the second λt0 terminator. Alternatively, the expression cassette contains, from 5' to 3', a first PhoA promoter followed by the cistron for heavy chain (TIR-H+Heavy Chain) and the first λt0 terminator, and a second PhoA promoter followed by the cistron for light chain (TIR-L+Light Chain) and the second λt0 terminator. Both TIR-L and TIR-H are contained within an STII signal sequence or a variant thereof.

For the xIL13 and xIL4 IgG4 hAb expression vectors a TIR combination of 1,1 and 2,2 was evaluated. For the xIL17 and xIL33 IgG4 hAb expression vectors a TIR2,2 was evaluated. The first number represents the TIR strength of the light chain and the second represents the TIR strength of the heavy chain. In addition to the xIL13, xIL4, xIL17 and xIL33 IgG4 hAbs, other IgG1 isotype hAb vectors were constructed and tested.

Chaperone Expression Plasmid Construction

To determine the chaperone expression to be combined with the vectors described above to yield the highest titers of the xIL13, xIL4, xIL17 and xIL33 hAbs, plasmids were provided for co-expression. A number of known chaperones were tested including FkpA protein, a peptidylprolyl cis-trans isomerase with chaperone activity. To do so, compatible plasmids (pACYC, Novagen, Madison, Wis.) were constructed containing the ORF for FkpA, as described in EP1356 052 (see, e.g., Examples 9-10, in particular paragraph [0207]).

Expanding upon this work for the current process, a set of FkpA compatible vectors were similarly generated to modulate the levels of FkpA co-expression. The modulation of FkpA levels was accomplished through optimization of the signal peptide as previously described (Simmons and Yansura, supra, 1996). Briefly, the 5' end of the FkpA ORF contained either a FkpA signal peptide (native or variant), or an STII signal peptide. All FkpA variant gene constructs were under the control of a tacII promoter.

These plasmids were then co-transformed with the hAb expression plasmids described above into strain 66F8. The genotype of the host strain 66F8 is W3110 ΔfhuA ΔphoA ilvG2096 (Val$^r$) Δprc spr43H1 ΔdegP ΔmanA lacI$^Q$ ΔompT ΔmenE.

For the xIL13 hAb, TIR1,1 and TIR2,2 plasmids encoding the LC and HC of the half antibody and FkpA were constructed and used to transform 66F8. In these plasmid constructs, the expression of FkpA was controlled by a phoA promoter upstream of the ORF for the LC. The pBR322 plasmid is typically maintained at approximately 30 copies/cell (Bolivar et al., Gene, 2:95-113, 1977) and the pACYC plasmid is typically maintained at approximately 15 copies/cell (Chang and Cohen, J. Bacteriol., 134:1141-1156, 1978). Without wishing to be bound to theory, it is thought that an increase in copy number when FkpA is moved onto the Ab expression plasmid may result in an increase in the amount of FkpA made.

Oxidoreductase Plasmid Construction

Similar to the compatible plasmid system described for the co-expression of FkpA, compatible plasmids were utilized to screen various known oxidoreductases in combination with the hAb expression plasmid that incorporated one of the FkpA TIR variants previously described. This work was performed with the TIR2,2 plasmid identified as pxIL13.2.2.FkpAc13. In addition compatible plasmids were utilized to screen FkpA and oxidoreductases in combination with xIL4 and other IgG1 hAbs.

The construction of the original oxidoreductases compatible plasmids was as described in EP 1356052 (see, e.g., Example 9). The screening of the oxidoreductases included expression from the compatible plasmid JJ247 with hAb expression plasmid xIL13.2.2.FkpAc13. In the xIL13 hAb example, oxidoreductase expression was either induced with 1 mM IPTG or left uninduced to modulate oxidoreductase levels.

Single plasmids encoding the LC and HC of the hAb and the chaperones FkpA, DsbA and DsbC were also constructed and used to transform 66F8. In the xIL13 hAb example, two TIR2,2 single plasmids were constructed differing in the promoter used to drive the expression of FkpA. The single plasmid MD157 contained a phoA promoter for FkpA expression and the plasmid KA01 contained a tacII promoter. The utilization of different promoters allowed further modulation of FkpA expression. In the xIL17 hAb example, a TIR2,2 single plasmid was constructed (MD341), which utilized a phoA promoter for FkpA expression. In all single plasmid conditions, expression of DsbA and DsbC were under the control of a tacII promoter in a polycistronic fashion. In the xIL4 hAb example, a TIR2,2 single plasmid was constructed that incorporated the ORFs of the compatible chaperone plasmid AH8145, described below, and identified as CB1.

In addition to the single plasmid system described above, a triple chaperone compatible plasmid system was also evaluated with a number of hAbs of both IgG1 and IgG4 isotype. In the compatible plasmid system one of the FkpA TIR variants described previously was cloned into the polycistronic DsbA and DsbC compatible plasmid (JJ247) and is identified as AH8145.

Fermentation Process

Large scale production was essentially as described in EP1356052 (see, e.g., Example 4 and paragraphs [0159]-[160]). For each 10-liter fermentation, 0.5 mL of frozen stock culture (containing 10-15% DMSO) was thawed and used to inoculate a 2 L shake flask containing 500 ml of Soy LB medium supplemented with either 0.5 ml of tetracycline solution (5 mg/ml) and/or 2 mL of kanamycin solution (5 mg/mL) and 2.5 ml 1M sodium phosphate solution. This seed culture was grown for approximately 16 hours at 30° C. with shaking and was then used to inoculate the 10-liter fermentor.

The fermentor initially contained approximately 7.0 liters of medium containing 1.1 g of glucose, 100 ml of 1M magnesium sulfate, 10 ml of a trace element solution (100 ml hydrochloric acid, 27 g ferric chloride hexahydrate, 8 g zinc sulfate heptahydrate, 7 g cobalt chloride hexahydrate, 7 g sodium molybdate dihydrate, 8 g cupric sulfate pentahydrate, 2 g boric acid, 5 g manganese sulfate monohydrate, in a final volume of 1 liter), either 20 ml of a tetracycline solution (5 mg/ml in ethanol) or 250 mL of an ampicillin solution (2 mg/mL), 1 bag of HCD salts, (37.5 g ammonium sulfate, 19.5 g potassium phosphate dibasic, 9.75 g sodium phosphate monobasic dihydrate, 7.5 g sodium citrate dihydrate, 11.3 g potassium phosphate monobasic), 200 g of BL4 Soy (a soy protein hydrolysate), and 100 grams of Yeast Extract. Fermentations were initially performed at 30° C. with 20 standard liters per minute (slpm) of air flow and were controlled at a pH of 7.0±0.2 (although occasional excursions beyond this range occurred in some cases). The back pressure of the fermentor was maintained at 1 bar gauge and the agitation rate was initially set to 650 rpm. As discussed in detail in Example 2 below, the agitation rate can also be varied to manipulate the oxygen transfer rate in the fermentor, and, consequently, control the cellular respiration rate. In addition as discussed in detail in Example 3 below, the temperature during the growth and production phases can be adjusted to maximize product yield.

Following inoculation of the fermentor with the cell-containing medium from the shake flask, the culture was grown in the fermentor to high cell densities using a computer-based algorithm to feed a concentrated glucose solution to the fermentor. Ammonium hydroxide (58% solution) and sulfuric acid (24% solution) were also fed to the fermentor as needed to control pH. L-61 antifoam was also added in some cases to control foaming.

When the culture reached a cell density of approximately 40 $OD_{550}$, an additional 100 ml of 1M magnesium sulfate was added to the fermentor. Additionally, a concentrated salt feed (12.5 g ammonium sulfate, 32.5 g potassium phosphate dibasic, 16.25 g sodium phosphate monobasic dihydrate, 2.5 g sodium citrate dihydrate, 18.75 g potassium phosphate monobasic, 10 ml of 2.7% ferric chloride and 10 ml of trace elements in a final volume of 1250 ml) was added to the fermentor and started at a rate of 2.5 ml/min when the culture reached approximately 20 $OD_{550}$ and continued until approximately 1250 ml were added to the fermentation. Fermentations were typically continued for 70-80 hours.

Sample Preparation for Electrophoresis, Immunoblot, and HPLC Analysis

Non-reduced soluble sample prep is similar to what is described in EP1356052 (see, e.g., Example 4, in particular paragraph [0162]). In particular, non-reduced soluble samples were prepared as follows: frozen, 1 mL whole broth samples taken during the course of the fermentation were thawed at room temperature. 100 μL of the thawed whole broth was added to 500 μL of extraction buffer. (Extraction buffer: 10 mM Tris, pH 6.8, 5 mM EDTA, freshly added 0.2 mg/mL of hen egg lysozyme, and freshly prepared iodoacetic acid to a final concentration of 5-10 mM.) The whole broth samples plus extraction buffer were incubated on ice for 5-10 minutes, then sonicated 2×10 pulses, then centrifuged at 4° C. and 14,000 rpm for 15-20 minutes. The supernatant was removed as the soluble fraction. For analysis by SDS-PAGE and immunoblots, the soluble fraction was diluted 1:10 into 2× Novex Tricine sample buffer without reducing agent. 10 μL of this prep was loaded onto a 10 well Novex 10% Bis-Tris NuPage gel and electrophoresed at 150 V with MES buffer. The gel was then used for either an immunoblot or stained with Coomassie Blue.

Samples of the soluble fractions were submitted for analysis by a LC-Kappa/RP assay. This assay is a 2-dimensional HPLC assay where the first column is an affinity column that captures kappa-light-chain containing IgG components and the second column is a reversed-phase column. An integral HPLC workstation was configured in the dual column mode. The solvent reservoirs were: Solvent 1A, affinity loading buffer; Solvent 1B, affinity elution buffer, 0.2% TFA in water; Solvent 2A, reversed-phase aqueous buffer, 0.1% TFA in water; Solvent 2B, reversed-phase organic elution buffer, 0.1% TFA in 80% acetonitrile. The first column was POROS® CaptureSelect™ LC Kappa affinity column (2.1×30 mm) purchased from Life Technologies (Carlsbad, Calif.). All procedures involving the affinity column were performed at ambient temperature.

The second column was POROS® R2 20 μm reversed-phase column (2.1×30 mm) purchased from Life Technologies (Carlsbad, Calif.). The reversed-phase column temperature was maintained at 80° C.

The affinity column was equilibrated in loading buffer, and a sample was loaded at a flow rate of 2 ml/min. The flow-through was directed to waste. After the sample was loaded, the affinity column was washed with loading buffer (3 ml) to reduce non-specifically bound components. Then, by valve switching, the affinity column was connected to the reversed-phase column and eluted with elution buffer (5 ml) at a flow rate of 2 ml/min to transfer the affinity captured components to the reversed-phase column. During this transfer step, the Integral UV detector was located after the affinity column and before the reversed-phase column, hence monitoring the elution of the affinity column, which became the load to the reversed-phase column. After elution and disconnection from the reversed-phased column, the affinity column was washed by water (2 ml) and subsequently re-equilibrated with loading buffer (4 ml).

The loaded reversed-phase column was washed with aqueous 0.1% TFA (1.1 ml). The flow rate was set to 2 ml/min and a rapid gradient (0.25 min) was run to 35% solvent 2B (0.1% TFA/80% acetonitrile) followed by a shallow gradient to 50% solvent 2B over 3 min. Elution was completed by a gradient to 100% solvent 2B in 0.5 min and held for 1.5 min. The reversed phase column was then returned to initial conditions in 0.05 min and held for 2 min to re-equilibrate. The column eluate was monitored at 280 and 214 nm. Quantitation was performed by comparison of the integrated peak areas with those of standards of known concentrations based on separation from the reversed-phase column.

The soluble and total amounts of LC and HC produced during the fermentation process were also quantitated. To perform the total RP-HPLC quantification fermentation broth samples were diluted 10 fold with 100 mM DL-Dithiothreitol (Sigma cat. #43816) in 6 M Guanidine HCL, 360 mM TRIS, 2 mM EDTA pH 8.6) with 200 mM. Samples were vortexed, incubated at 60° C. for 20 mins and centrifuged at 13,000 RPM for 15 min at 4° C. The soluble fraction was filtered using a 0.22 um filter prior to injection on the HPLC. The HPLC system used was an Agilent Technologies 1290 Infinity system. Samples were injected onto a Zorbax 300SB-C3 Rapid Resolution (4.6×150 mm 3.5 micron) analytical column (cat. #863973-909). Mobile phase A consisted of 0.1% Trifluoroacetic acid (Thermo cat. #28901) in SQH2O and mobile phase B 0.08% Trifluoroacetic acid in HPLC-grade acetonitrile (Honeywell cat. # AH015-4).

To perform the total soluble RP-HPLC quantification fermentation broth samples were both homogenized (10,000 RPM) and sonicated (88% amplitude) for 10 sec four times with a Pro-Scientific DPS-20. Samples were then centrifuged at 4° C. and 14,000 rpm for 15-20 minutes. The supernatant was removed as the soluble fraction and denatured and processed on the RP-HPLC as described above.

Results

Effect of FkpA Expression on hAb Titer

As shown in FIG. 1A, production of light and heavy chain subunits from the xIL13 hAb TIR1,1 vector resulted in total amounts of light and heavy chains production of 2.9 g/L and 1.2 g/L, respectively. For the TIR2,2 the total amount of light and heavy chains produced was 6.4 g/L and 4.1 g/L, respectively.

Figure 1B:
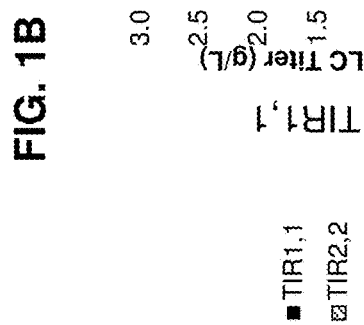
Figure 1C:
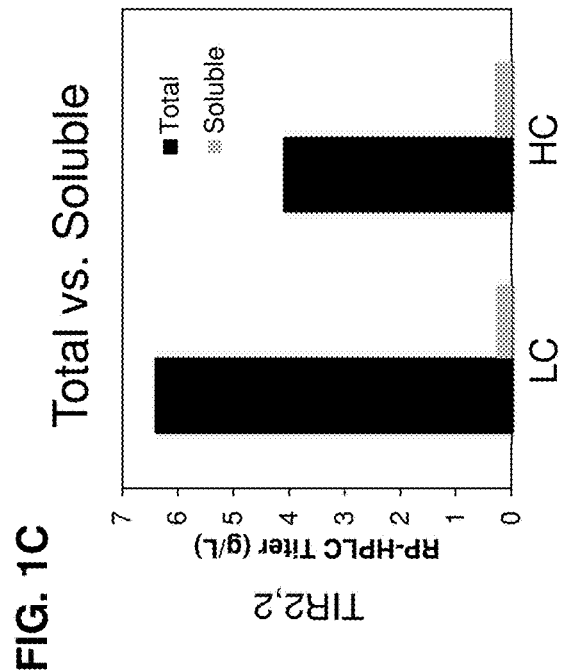
Figure 2:
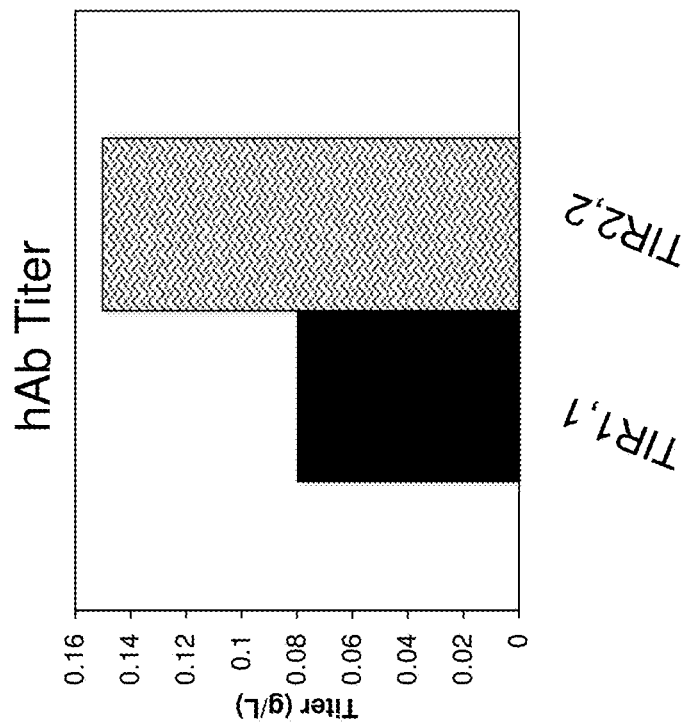
FIG. 2 shows the titer of the xIL13 hAb using TIR1,1 (black bar) or TIR2,2 (striped bar) hAb production vectors as measured by dual column RP-HPLC.

However, the amount of total subunit production did not result in significant soluble subunit accumulation. Using the xIL13 TIR1,1 hAb plasmid, the total soluble amount of light and heavy chains produced was 0.2 g/L and less than 0.1 g/L, respectively (FIG. 1B). For the TIR2,2 hAb the total soluble amounts of light and heavy chains produced was 0.3 g/L and 0.3 g/L, respectively (FIG. 1C). The titer of assembled xIL13 hAb produced for the TIR1,1 fermentation was only 0.1 g/L, and for the TIR2,2 fermentation the titer was less than 0.2 g/L (FIG. 2). These results suggest the presence of significant inefficiencies in the folding and/or assembly of the hAb product. Therefore, further work was performed evaluating the effect on titer of using the TIR1,1 and TIR2,2 plasmids with the co-expression of chaperones.

Figures 3A, 3B:
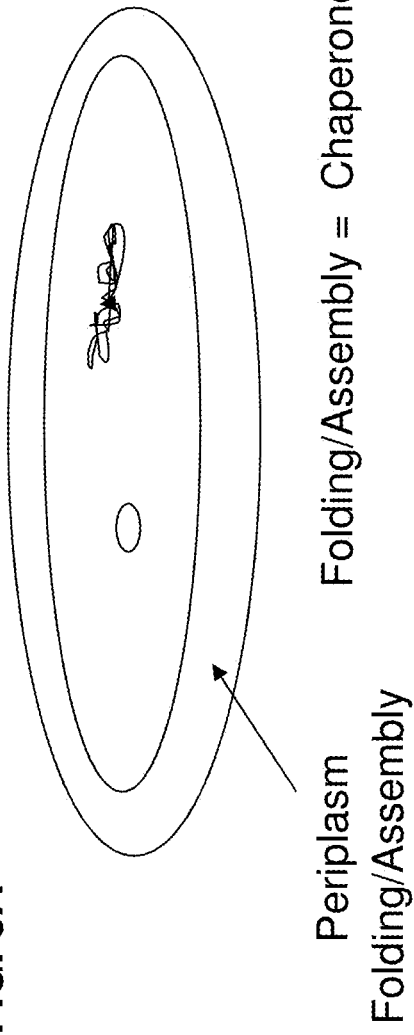
FIG. 3A-B illustrates the folding and assembly of proteins in bacterial host cells.

Several classes of chaperone proteins are known to promote protein folding and assembly (FIG. 3A-B). Particular chaperones of interest include FkpA, which is known to function as a peptidyl-prolyl cis-trans isomerase and a chaperone, and DsbA and DsbC, which are known to function as oxidoreductases. Experiments were undertaken to test whether expression of FkpA, DsbA, and DsbC affected hAb production.

Figures 4A, 4B:
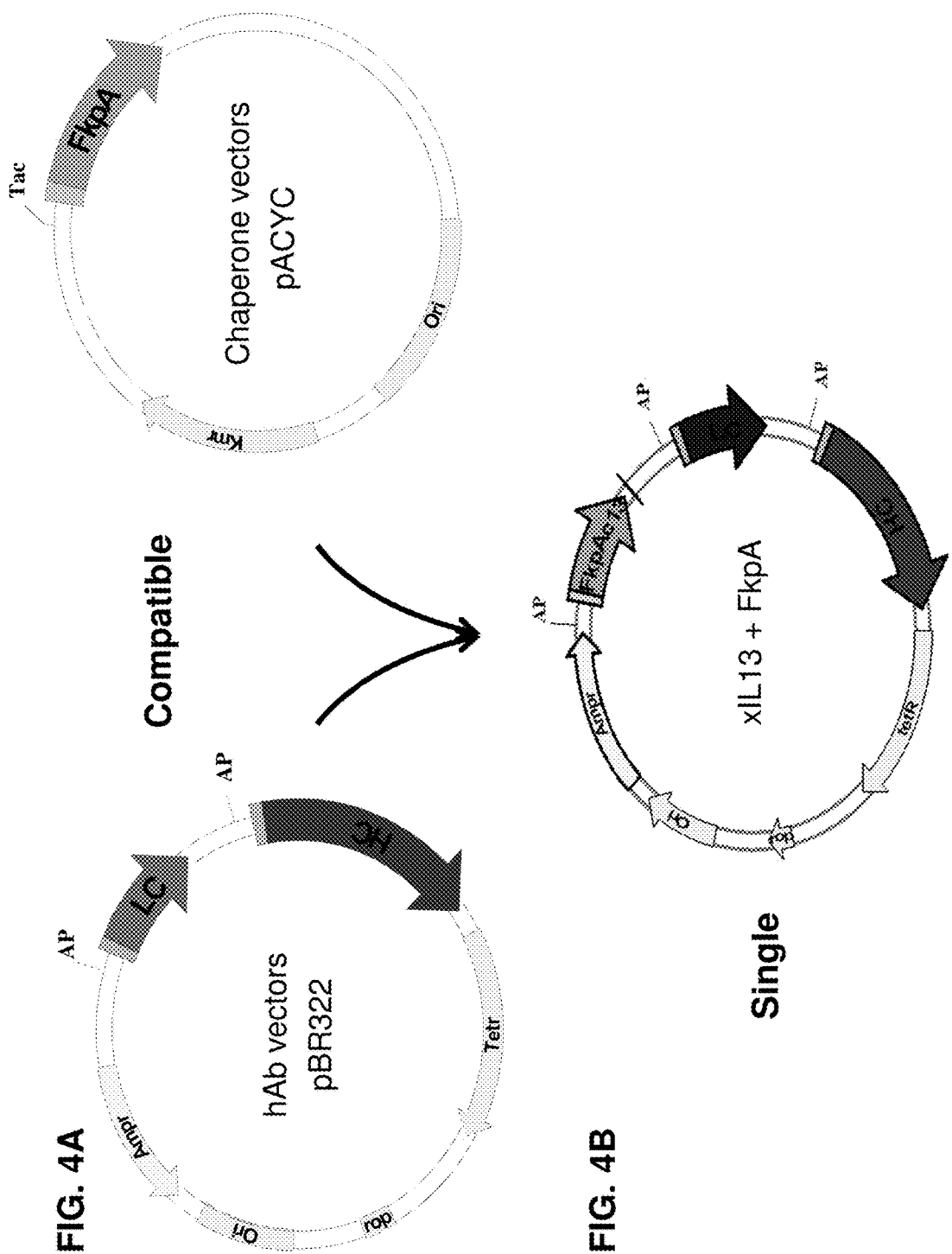
FIG. 4A shows the compatible system used to screen FkpA variants.
FIG. 4B shows the generation of a single xIL13 plasmid (pxIL13.2.2.FkpAc13) encoding an antibody LC, HC, and FkpA.

In particular, the effect of expressing FkpA using a separate plasmid (compatible plasmid system) or the same plasmid (single plasmid system) encoding the hAb HC and LC ORFs was examined (FIG. 4A-B). Use of a single expression plasmid eliminates the need to use multiple antibiotics or other means of selective pressure to ensure plasmid retention. In the single plasmid system used for xIL13 hAb, the promoter driving FkpA expression was changed from an IPTG-inducible tacII promoter to a phoA promoter. Therefore, phosphate depletion in the culture leads to expression of the HC, LC, and FkpA.

Figure 5B:
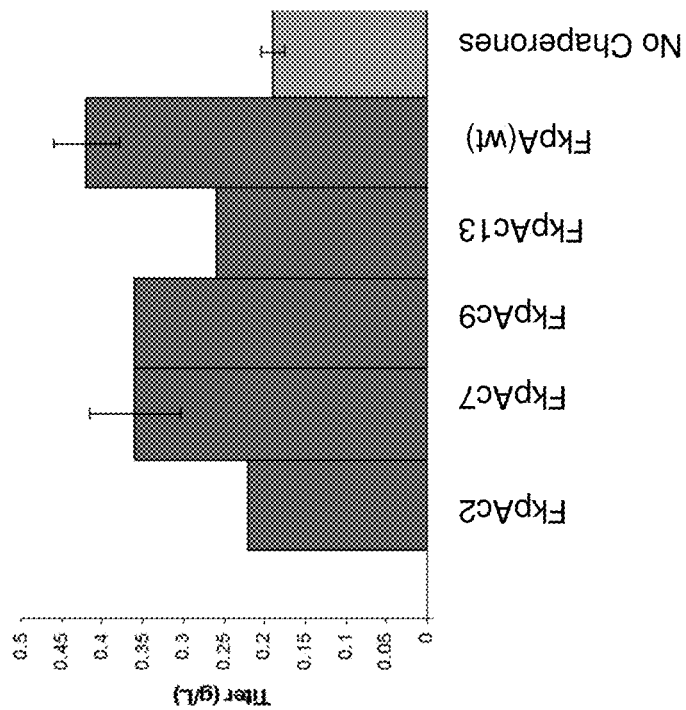
FIG. 5A-B shows the production of the xVEGF IgG1 hAb upon titration of FkpA expression.
Figure 5A:
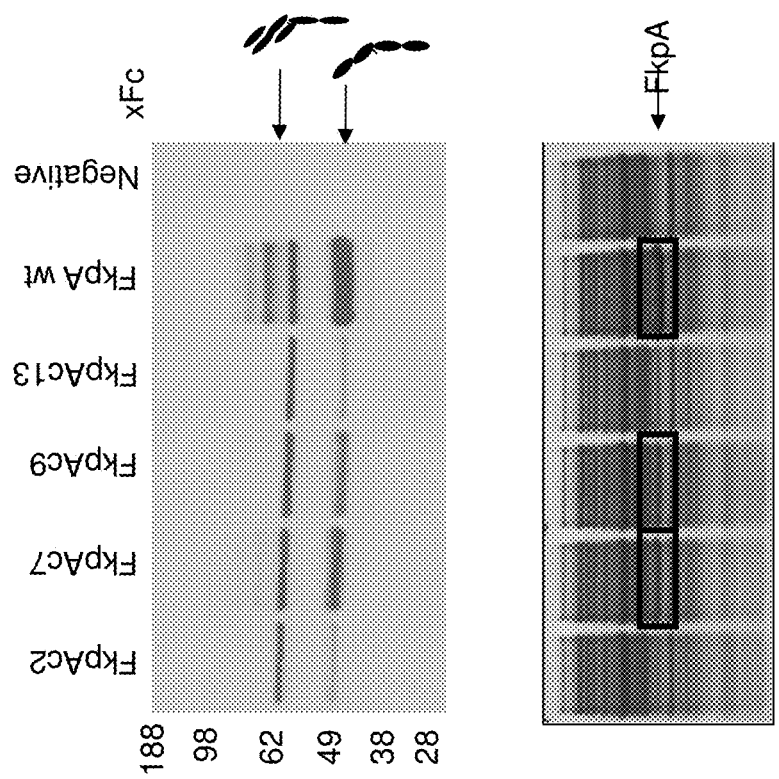

Increased levels of FkpA chaperone co-expression correlated with increased amounts of soluble monomeric heavy chain accumulation in addition to increased assembled hAb for an IgG1 isotype hAb (xVEGF) (FIG. 5A). In this experiment a set of FkpA expression variants, as described previously, was screened with 1 mM IPTG induction. Without FkpA co-expression, the titer of the xVEGF hAb was 0.2 g/L and in the condition with the highest level of FkpA co-expression (FkpA(wt)) the hAb titer was approximately 0.4 g/L (FIG. 5B).

For the production of xIL13 hAb, a compatible plasmid system (expression of xIL13 HC and LC from one plasmid and FkpA from another, as shown in FIG. 4A) using a TIR1,1 or TIR2,2 antibody expression vector was tested. For the compatible plasmid systems induced with 1 mM IPTG to drive co-expression of FkpA, the titer for the TIR1,1 plasmid was 0.2 g/L and 0.4 g/L for the TIR2,2 plasmid (FIG. 6A, lanes 3 and 4). This resulted in an approximate two-fold increase in titer compared with TIR1,1 and TIR2,2 conditions with endogenous levels of FkpA (FIG. 6A, lanes 1 and 2). FIG. 6B shows the amount of FkpA expression induced in the compatible system, as compared to endogenous expression, as measured by ultra performance liquid chromatography (UPLC) in milliabsorption units (mAu) and Western blot.

The single plasmid system for FkpA expression and hAb production shown in FIG. 4B was also tested. For the xIL13 hAb, the titers for the single plasmid TIR1,1 and TIR2,2 were 0.4 g/L and 0.7 g/L, respectively (FIG. 6A). This represented an approximately two-fold increase in titer over the compatible plasmid system. The expression level of FkpA in the single plasmid system was also approximately two-fold higher than in the induced compatible plasmid system (FIG. 6B). Increased levels of FkpA expression correlated with increased amounts of soluble monomeric heavy chain accumulation in both TIR conditions.

Figure 7A:
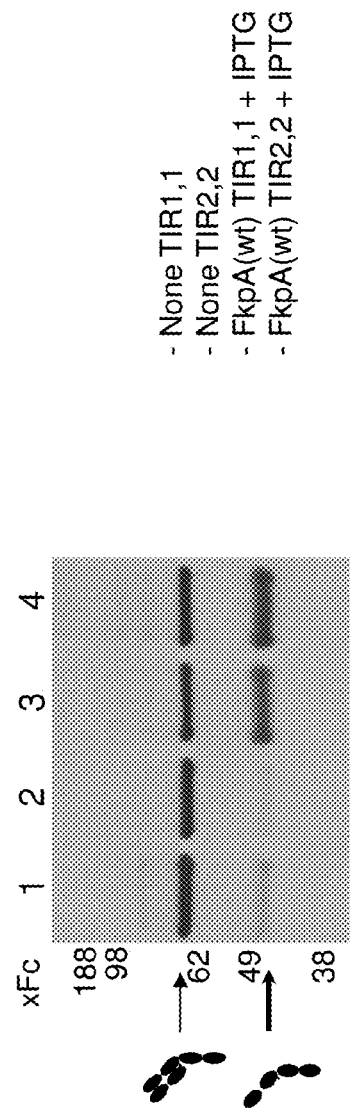
FIG. 7A-B shows the production of the xIL4 IgG4 hAb upon inducible expression of FkpA.
Figure 7B:
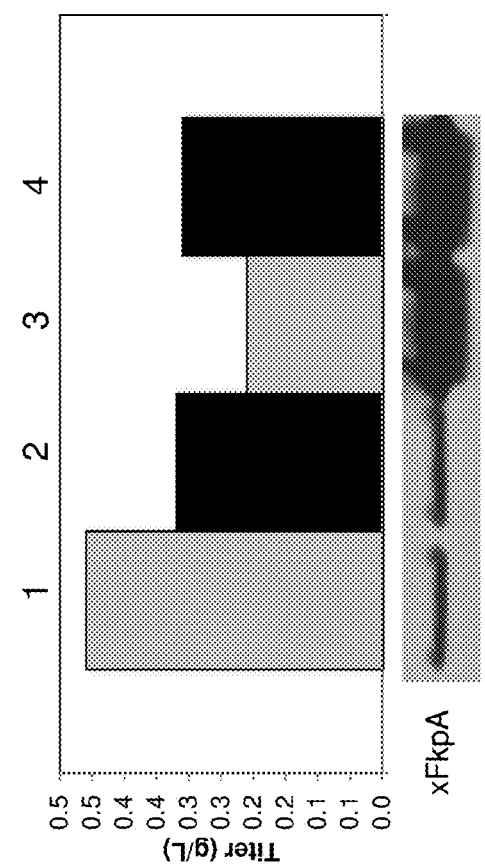

A third hAb (xIL4 IgG4) was tested with both TIR1,1 and TIR2,2 conditions with induced FkpA co-expression from a compatible plasmid system. In this experiment FkpA(wt) co-expression increased the amount of soluble monomeric heavy chain in both TIR conditions (FIG. 7A), but did not result in an increase in the titer of hAb produced (FIG. 7B).

Figure 8A:
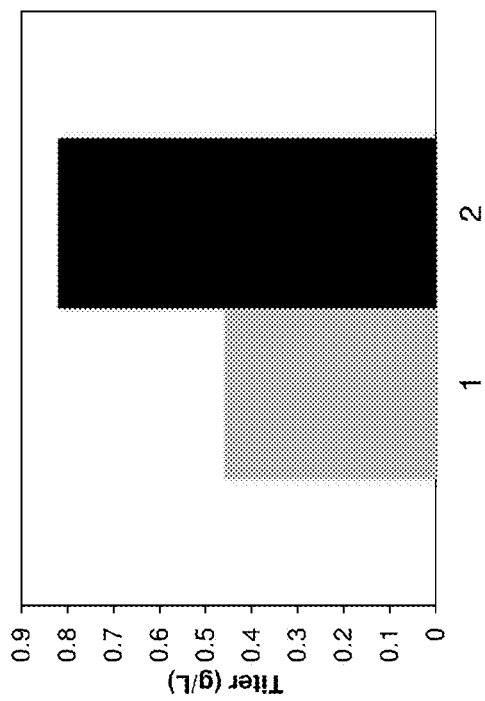
FIG. 8A-C shows the production of the xVEGFC IgG1 hAb upon expression of FkpA.
Figure 8C:
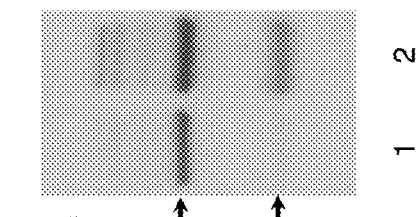
Figure 8B:
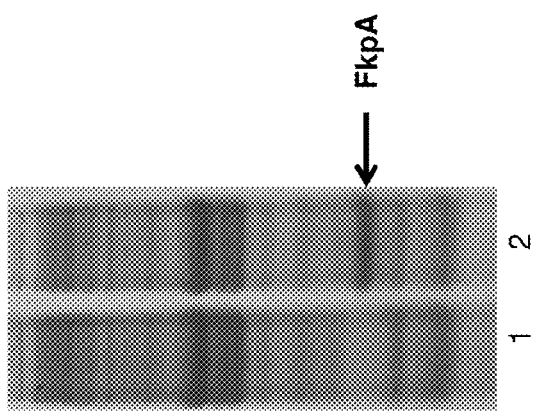

A fourth hAb (xVEGFC IgG1) was tested with induced FkpA co-expression from a compatible plasmid system. In this experiment FkpA(wt) co-expression increased the amount of soluble monomeric heavy chain and increased the titer from 0.5 g/L to 0.8 g/L (FIG. 8A). The increased FkpA expression as determined by Coomassie stain (FIG. 8B) correlated to an increase in soluble monomeric HC chain accumulation (FIG. 8C). In sum, these results suggest that FkpA expression enhances the accumulation of soluble monomeric heavy chain, but that the effect on assembled hAb titer is variable. This indicates that further optimization is desirable.

Figure 9:
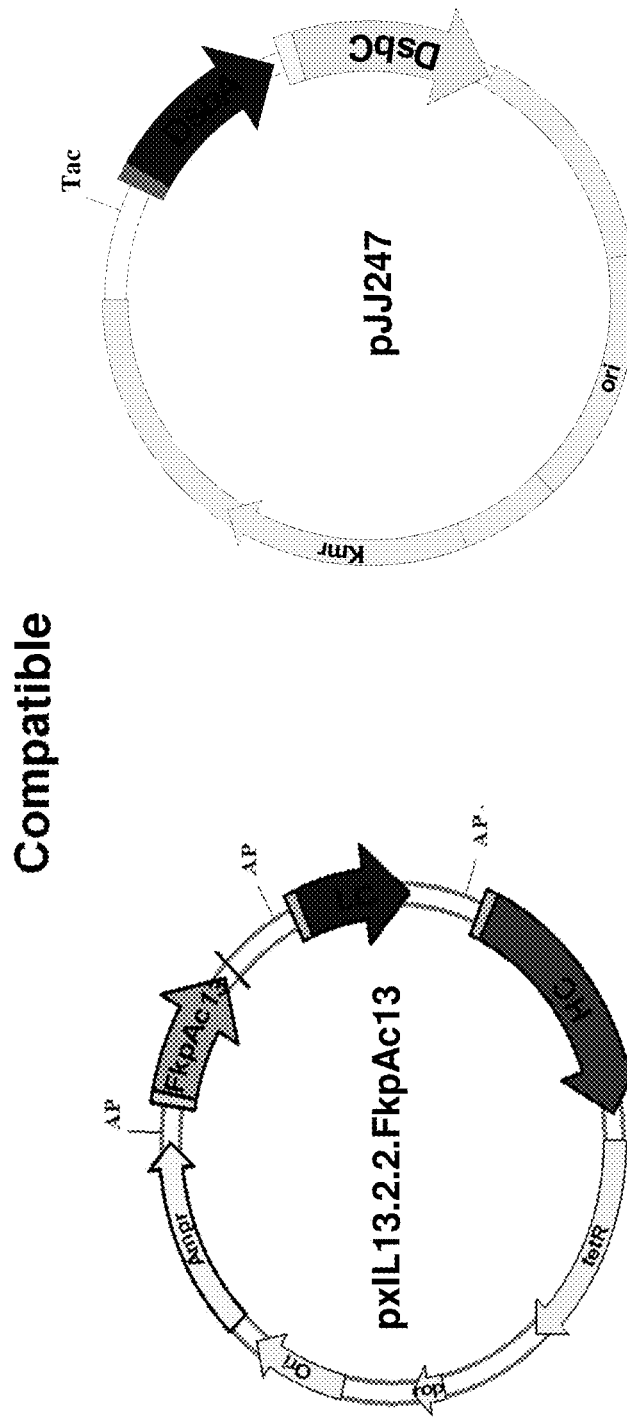
FIG. 9 shows the compatible plasmid system employing the a first plasmid for expression of the xIL13 hAb (pxIL13.2.2.FkpAc13) and a second plasmid for expression of DsbA and DsbC (pJJ247).
Figure 10:
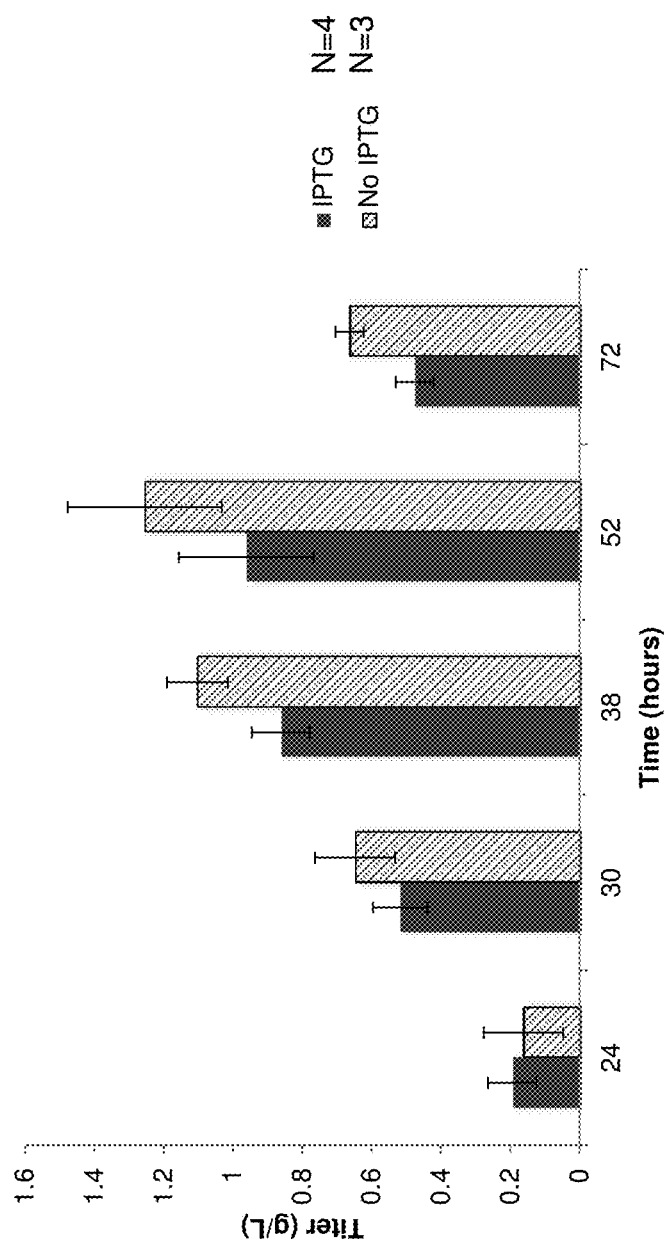
FIG. 10 provides a graph showing the production of the xIL13 hAb over time using the xIL13.2.2.FkpAc13 production plasmid and a compatible plasmid for expression of DsbA and DsbC, with and without IPTG induction.

Effect of DsbA and DsbC Expression on hAb Titer xIL13 hAb production was further optimized by combining the pxIL13.2.2.FkpAc13 (single plasmid) described above with a compatible plasmid for the expression of the oxidoreductases DsbA and DsbC (FIG. 9). A plasmid expressing both DsbA and DsbC (JJ247) with pxIL13.2.2.FkpAc13 increased hAb titers. FIG. 10 shows the titer of the xIL13 hAb produced over time, in the presence and absence of IPTG induction of DsbA and DsbC. The highest titer for the pxIL13.2.2.FkpAc13 with JJ247 was achieved at 52 hours into the fermentation. At this time point, in the condition without IPTG (non-induced condition) the xIL13 titer was 1.2±0.2 g/L and in the condition with IPTG (induced condition) the xIL13 titer was 1.0±0.2 g/L (FIG. 10). The drop in titer from 52 to 72 hours for both conditions tested was significant and was attributed to a drop in oxygen uptake rate (OUR) and rise in osmolality during the fermentation process as described in Example 2.

Figures 11A, 11B:
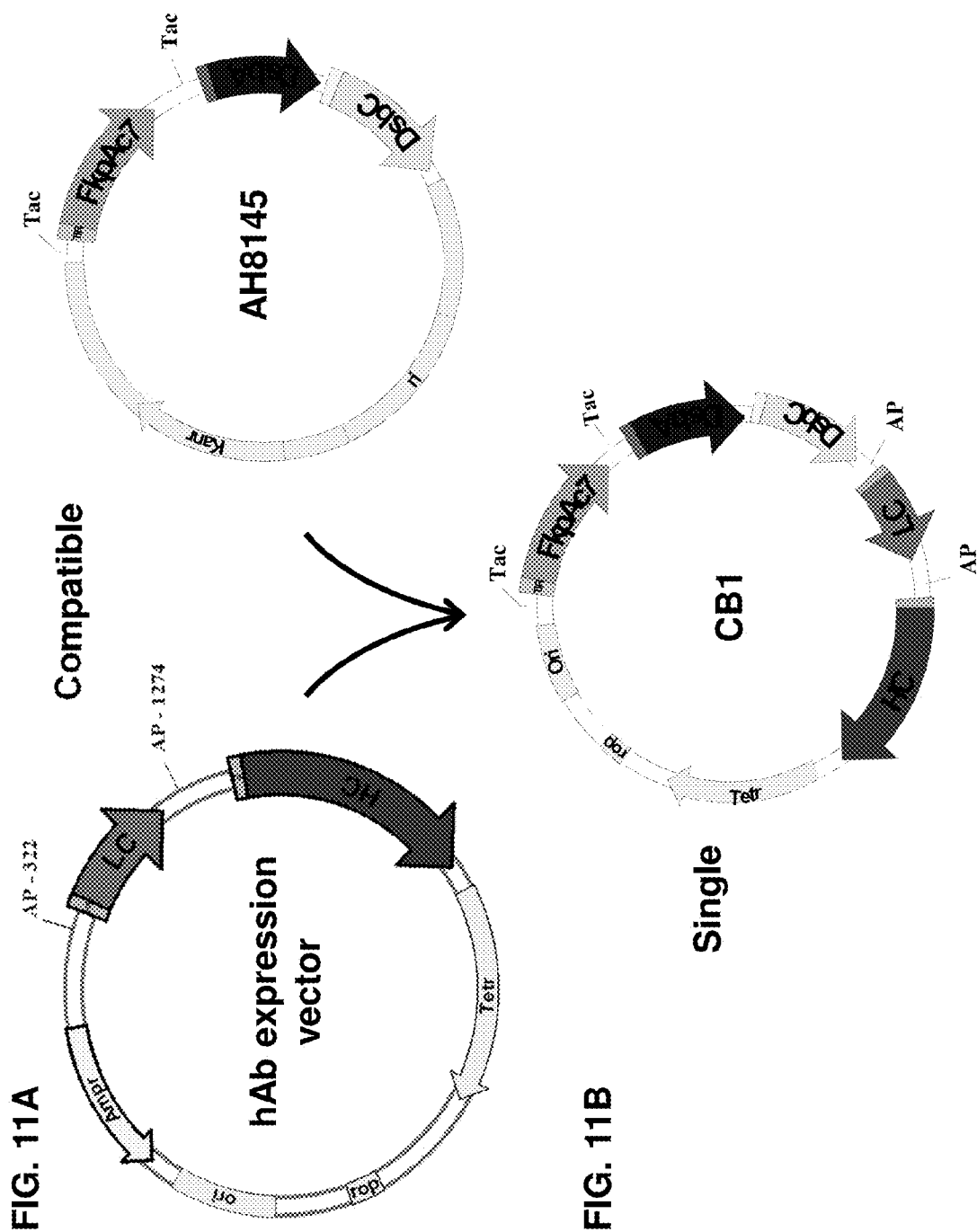
FIG. 11A shows the xIL14 hAb compatible plasmid system.
FIG. 11B shows the generation of a single plasmid encoding the xIL14 hAb LC and HC, FkpA, DsbA, and DsbC.
Figures 12A, 12B:
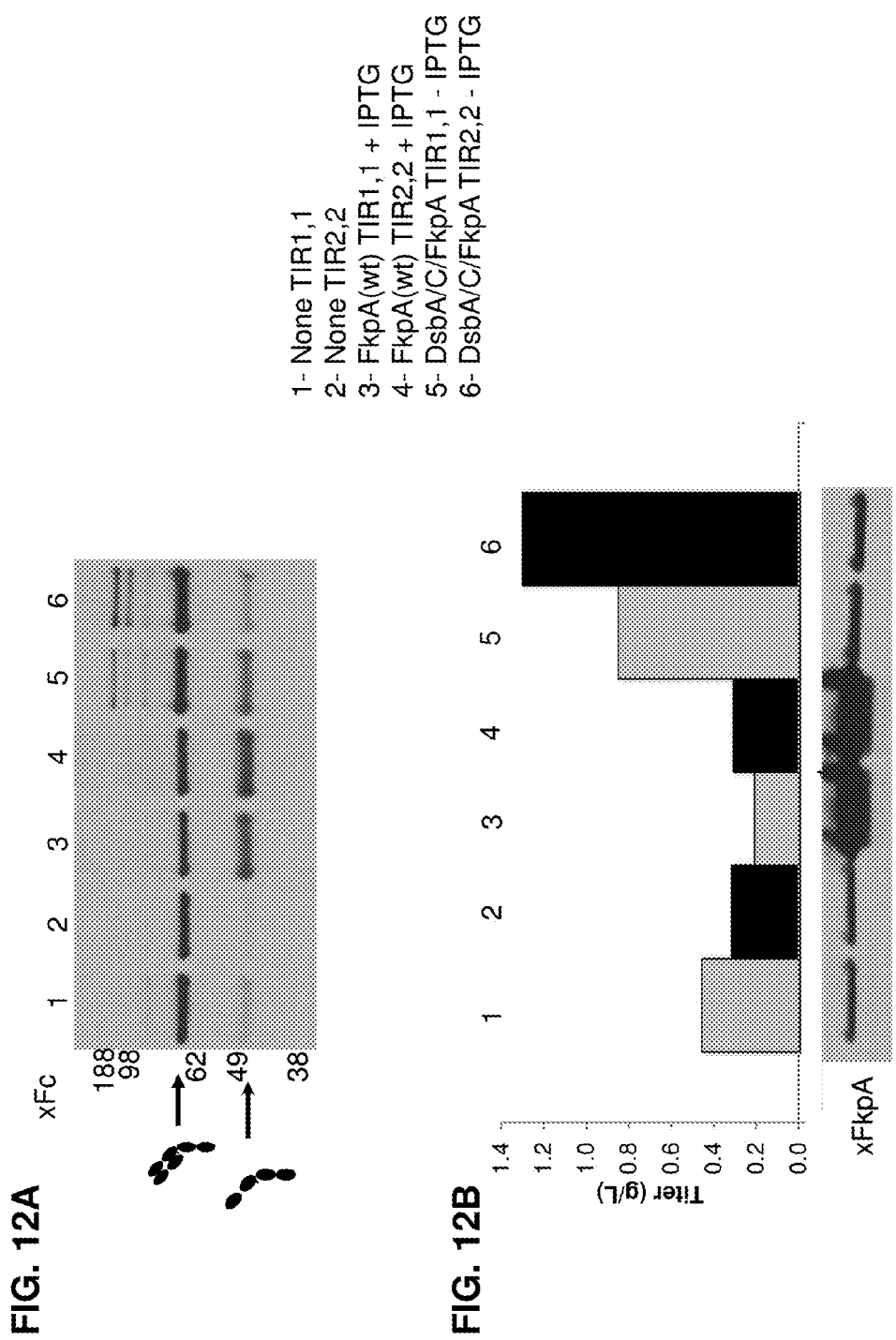
FIG. 12A-B shows the production of the xIL4 hAb with the TIR1,1 or TIR2,2 vector in the absence of FkpA, DsbA, and DsbC expression (1 and 2, as labeled); in the presence of IPTG-induced FkpA expression (3 and 4, as labeled); and in the presence of a plasmid with FkpA, DsbA, and DsbC in the absence of IPTG (5 and 6, as labeled).

A compatible system for expressing DsbA, DsbC, and FkpA (AH8145) was also evaluated with the xIL4 TIR1,1 and TIR2,2 Ab expression plasmids (FIG. 11A). The non-induced co-expression of all three chaperones resulted in a TIR1,1 and TIR2,2 titer of 0.8 g/L and 1.2 g/L, respectively (FIG. 12 lanes 5 and 6). This represented an approximately six-fold increase in titer for the TIR2,2 condition as compared to the previously described FkpA compatible TIR2,2 condition (FIG. 12 lanes 3 and 4).

Figure 13:
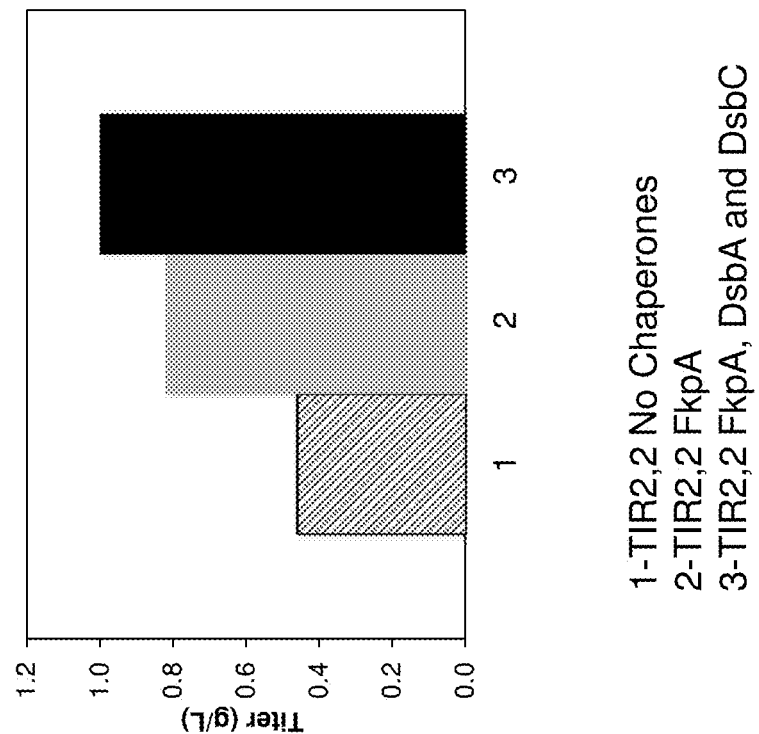
FIG. 13 shows the production of the xVEGFC hAb with a TIR2,2 vector in the absence of FkpA, DsbA, and DsbC expression (column 1); in the presence of IPTG-induced FkpA expression (column 2); and in the presence of a plasmid with FkpA, DsbA, and DsbC in the absence of IPTG (column 3).
Figure 14:
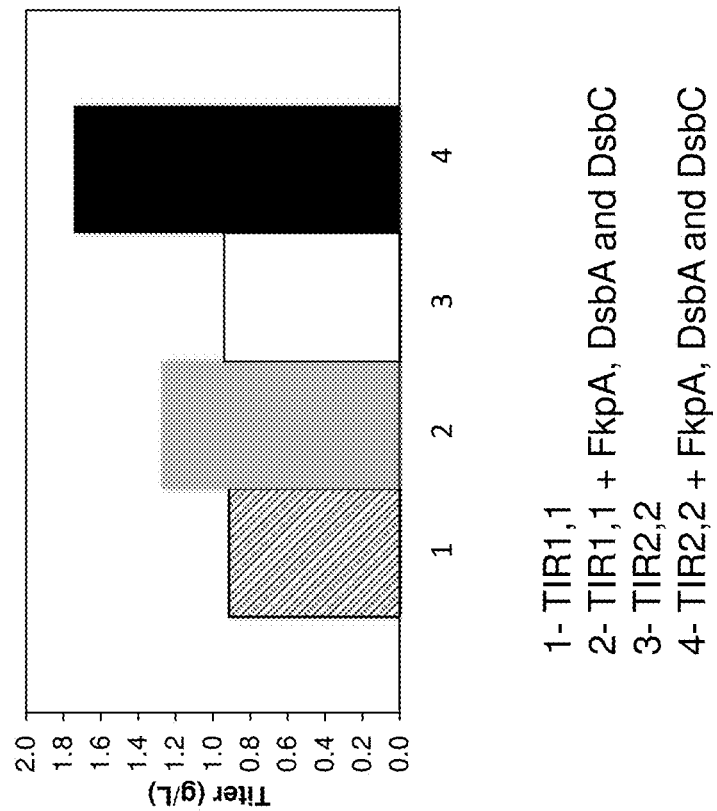
FIG. 14 shows the production of the xVEGFA IgG1 hAb with a TIR1,1 or TIR2,2 vector in the absence of FkpA, DsbA, and DsbC expression (1 and 3, as labeled); and in the presence of a plasmid with FkpA, DsbA, and DsbC in the absence of IPTG (2 and 4, as labeled).

The compatible non-induced AH8145 plasmid system was further evaluated with another hAb. Using a TIR2,2-based vector to produce the xVEGFC IgG1 hAb, the non-induced compatible AH8145 condition increased the titer to 1.0 g/L from 0.8 g/L, as compared to FkpA co-expression only (FIG. 13). A fifth hAb (xVEGFA IgG1) with both TIR1,1 and TIR2,2 conditions was tested with the AH8145 compatible plasmid. Without chaperone co-expression the titers for both the TIR1,1 and TIR2,2 conditions were similar, about 0.9 g/L (FIG. 14 lanes 1 and 3). With the compatible plasmid in the non-induced AH8145 condition, the titer for the TIR1,1 and TIR2,2 plasmids was 1.2 g/L and 1.7 g/L, respectively (FIG. 14 lanes 2 and 4).

Figure 15:
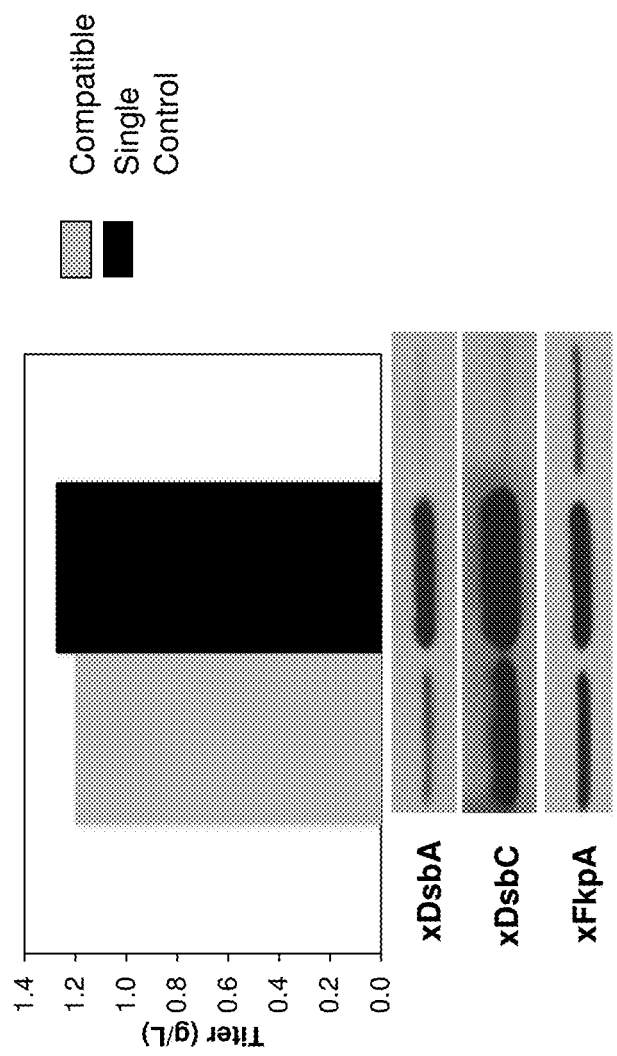
FIG. 15 shows the production of the xIL4 hAb with a TIR2,2 vector when FkpA, DsbA, and DsbC are expressed from the same vector ("Single") and when FkpA, DsbA and DsbC are expressed from a second compatible vector ("Compatible"), along with a negative control without the antibody expression vector and without DsbA, DsbC, and FkpA overexpression ("Control"). A Western blot shows expression of DsbA, DsbC, and FkpA.

The creation of a xIL4 TIR2,2 single plasmid that incorporated the chaperone ORFs of AH8145 was generated (CB1) and is illustrated in FIG. 11B. The CB1 plasmid without the addition of IPTG produced slightly higher titers than observed with the compatible plasmid system (FIG. 15). It should be noted that the hAb titers reported in this comparison were generated from fermentations that utilized an optimized agitation strategy as described in Example 2. By western blot, the levels of all three chaperones was slightly higher with CB1 (FIG. 15). Without wishing to be bound to theory, the single plasmid system may allow for higher plasmid copy number, which may result in higher yields.

Figures 16A, 16B:
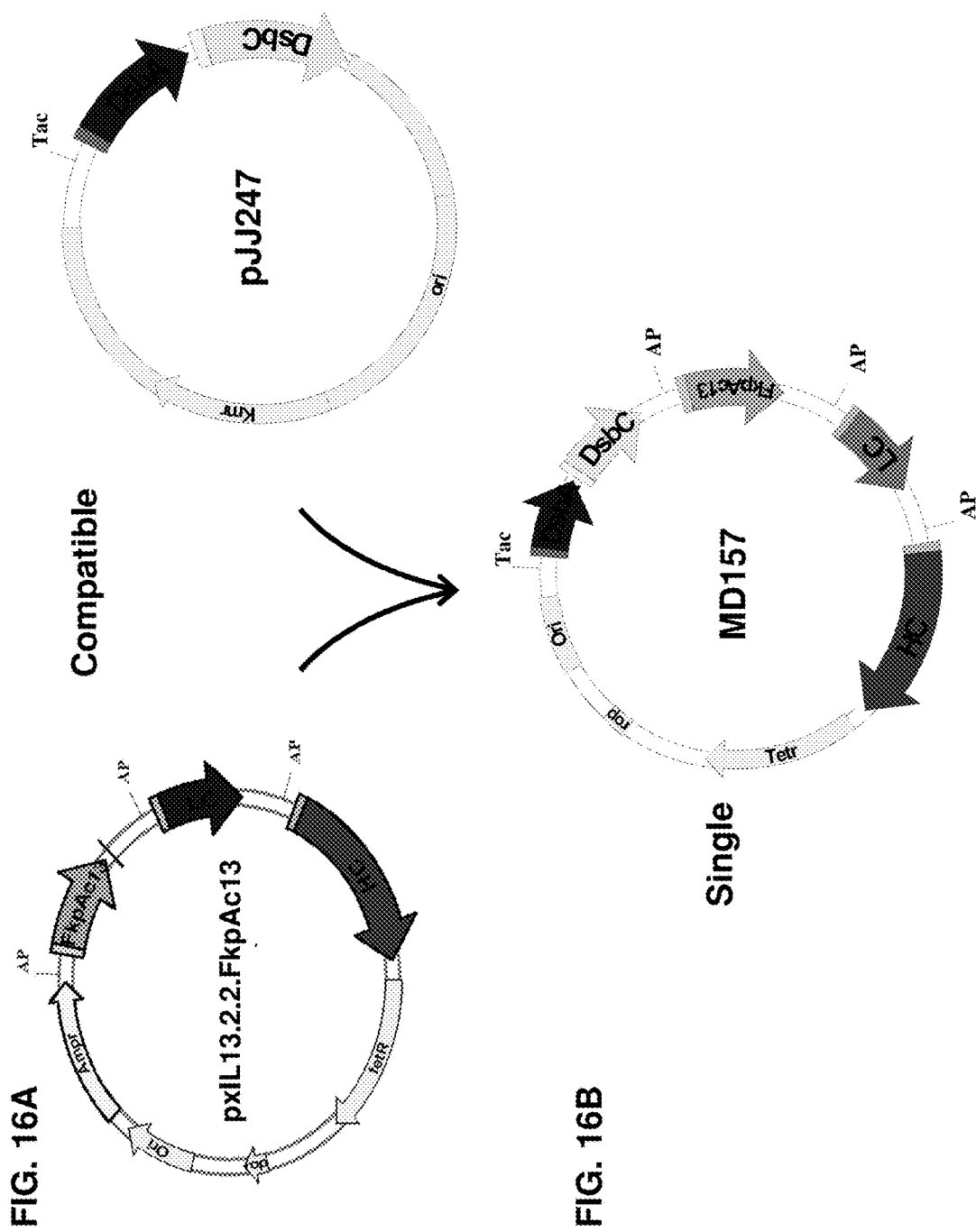
FIG. 16A shows the xIL13 compatible plasmid system utilizing the previously described pxIL13.2.2.FkpAc13 production plasmid and compatible oxidoreductase plasmid (pJJ247).
FIG. 16B shows the generation of a single plasmid (MD157) incorporating the open reading frames (ORFs) from pxIL13.2.2.FkpAc13 and pJJ247.
Figure 17:
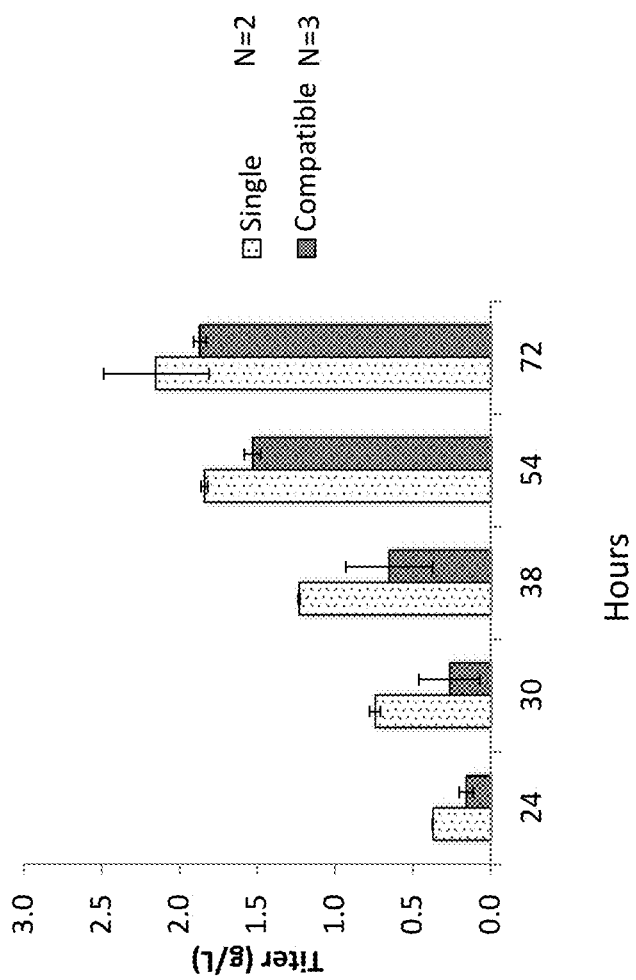
FIG. 17 shows the production over time of the xIL13 hAb with the TIR2,2 vector when FkpA, DsbA, and DsbC are expressed from the same vector ("Single") and when DsbA and DsbC are expressed from a compatible vector and FkpA is expressed from the xIL13.2.2.FkpAc13 vector ("Compatible"). These vectors use a phoA promoter to drive FkpA expression.

The xIL13 single plasmid system MD157 was compared to the uninduced compatible pxIL13.2.2.FkpAc13 and JJ247 compatible plasmid system (FIG. 16). The MD157 single plasmid condition produced titers of 2.1±0.3 g/L compared to 1.9±0.04 g/L in the compatible system (FIG. 17). It should be noted that the titers reported in this comparison were generated from fermentations that utilized an optimized agitation strategy as described in Example 2.

Taken together, these results demonstrate that co-expression of FkpA along with DsbA and DsbC increases the production of assembled hAb, using multiple hAb constructs to confirm these effects.

Example 2: Effect of Oxygen Uptake on Half-Antibody Production

The above results demonstrate an improvement in hAb production achieved by the co-expression of FkpA, DsbA, and DsbC along with the hAb HC and LC. However, even with this enhanced production, titers were found to plateau or even diminish at time points after 52 hours of production. Therefore, additional experiments were undertaken to further optimize hAb production.

As described previously, fermentations were initially performed at 30° C. with 20 standard liters per minute (slpm) of air flow and were controlled at a pH of 7.0±0.2. The back pressure of the fermentor was maintained at 1 bar gauge and the agitation rate was initially set to 650 rpm. The additional bar gauge of backpressure resulted in an initial dissolved oxygen concentration ($dO_2$) of 200%. The concentrated glucose solution was fed after the $dO_2$ signal dropped below 2% of the starting level, typically about two hours into the production culture, and was fed continuously over the course of the fermentation such that glucose was a non-limiting nutrient.

At 12 hours the cell density in the culture was sufficient to maintain the $dO_2$ concentration at or near zero percent. Without wishing to be bound to theory, it is thought that when oxygen concentration is limited, the oxygen transfer rate (OTR) is equal to the oxygen uptake rate (OUR) or metabolic rate of the cells. Manipulation of the OTR was facilitated by adjusting the agitation rate and had a direct effect on the culture OUR. A mass spectrometer was used to monitor the composition of the off-gas from the fermentations and enabled the calculation of the oxygen uptake and carbon dioxide evolution rates in the fermentations.

Figure 18:
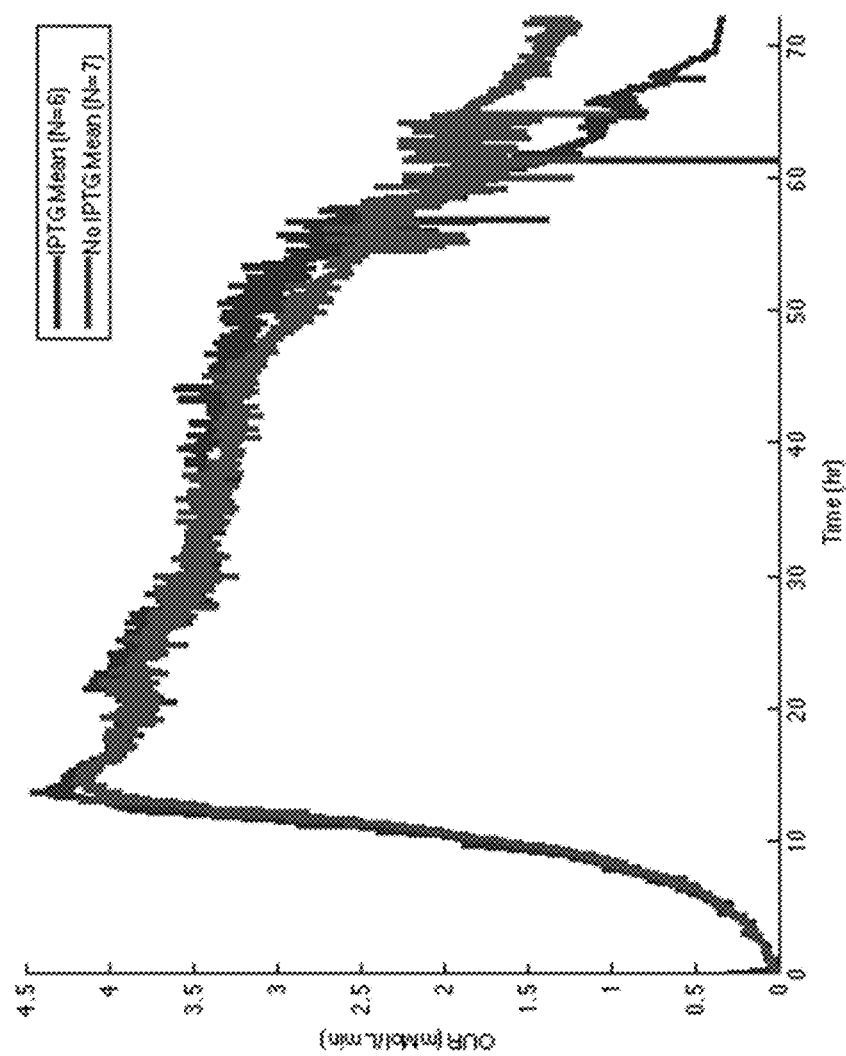
FIG. 18 shows the average oxygen uptake rate (OUR) over time in cultures grown under fixed agitation rate of cells bearing two vectors: a TIR2,2 vector expressing the xIL13 hAb and FkpA, and a vector expressing DsbA and DsbC under an IPTG-inducible promoter. OUR is shown for cultures grown in the presence or absence of IPTG. Number of samples used for each condition is provided ("N").
Figure 19:
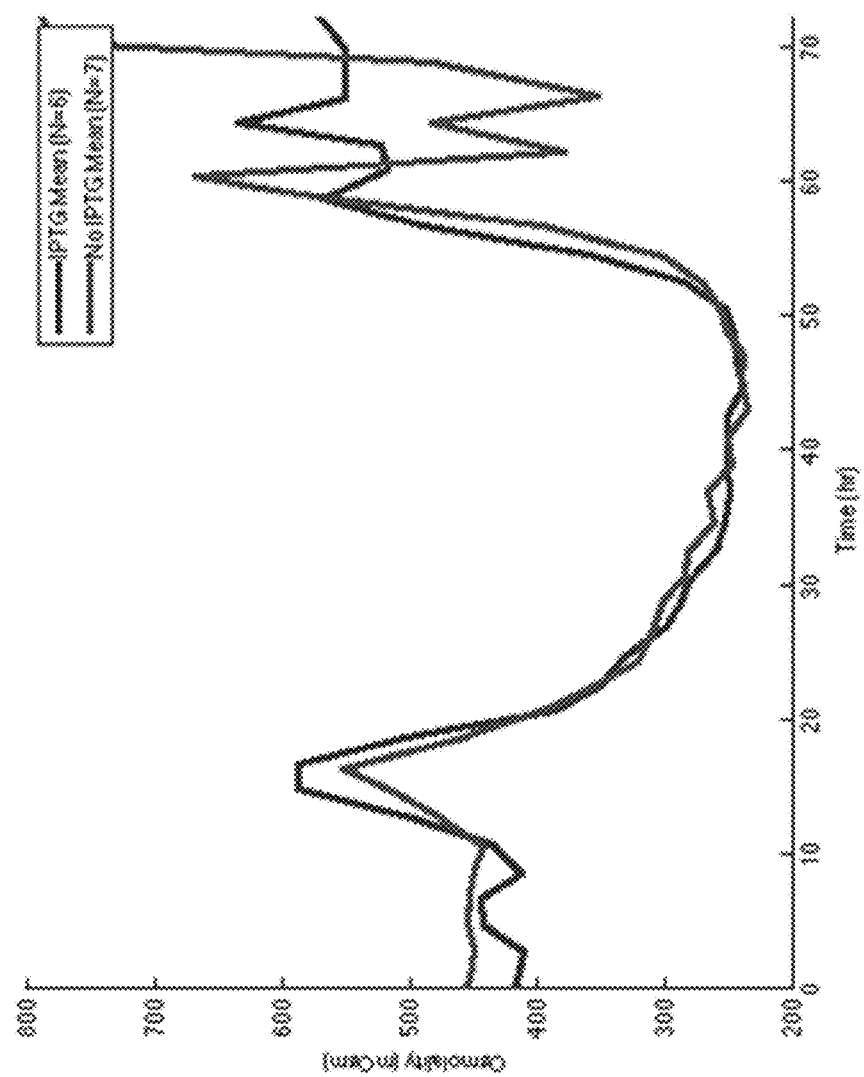
FIG. 19 shows the average osmolality in cultures grown under fixed agitation rate of cells bearing two vectors: a TIR2,2 vector expressing the xIL13 hAb and FkpA, and a vector expressing DsbA and DsbC under an IPTG-inducible promoter. Osmolality is shown for cultures grown in the presence or absence of IPTG. Number of samples used for each condition is provided ("N").

As shown in FIG. 18, in the pxIL13.2.2.FkpAc13 with JJ247 plasmid system described above, both the induced and non-induced TIR2,2 cultures had a peak OUR of 4.25 mmol/L/min at hour 12, after which point the $dO_2$ became limited. These cultures were grown under agitation at a constant rate of 650 rpm. FIG. 19 shows the osmolality of these cultures over time. Taken together, FIGS. 18-19 show that after 50 hours, cell culture OUR declined sharply and osmolality rose.

Figure 20:
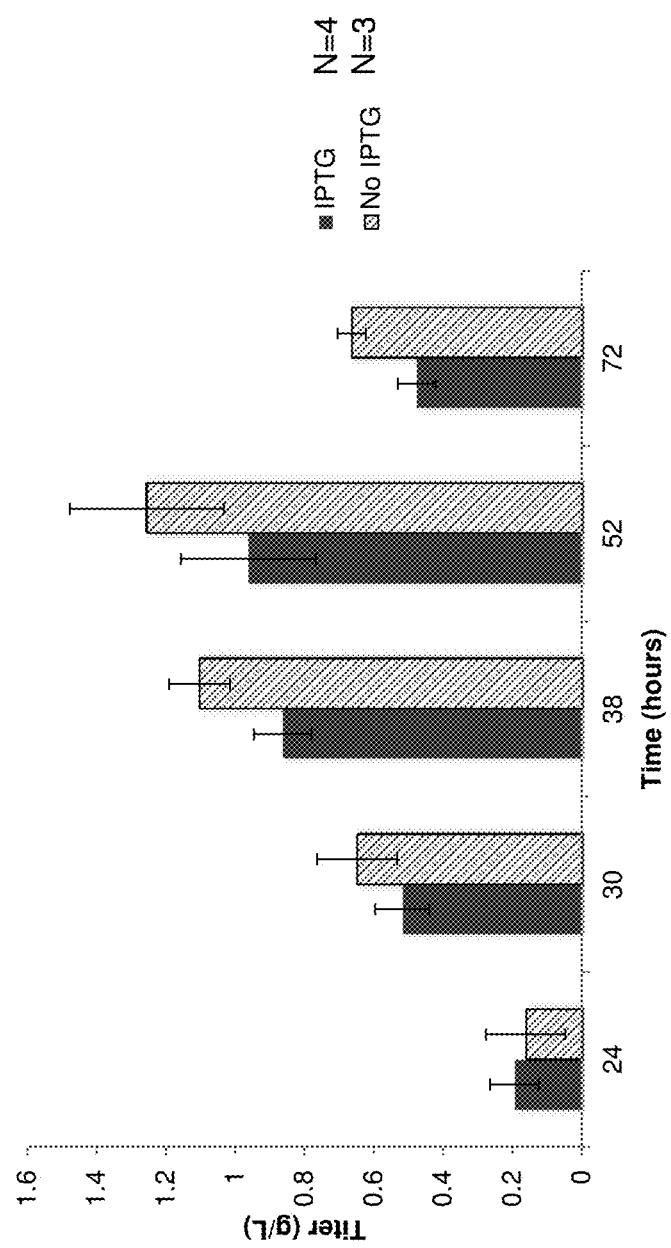
FIG. 20 shows the average titer of the xIL13 hAb produced over time from cells bearing two vectors: a TIR2,2 vector expressing the xIL13 hAb and FkpA, and a vector expressing DsbA and DsbC under an IPTG-inducible promoter. Titer of antibody produced is shown for cultures grown in the presence or absence of IPTG. Number of samples used for each condition is provided ("N").

FIG. 20 shows the xIL13 hAb titer produced over time in these cultures. A drop in titer from 1.2 g/L±0.2 g/L at 52 hours to 0.7±0.04 g/L at 72 hours was observed. Similarly, in the induced condition, a drop from 1.0±0.2 g/L at 52 hours to 0.5±0.05 g/L at 72 hours was observed. Intriguingly, this drop in production occurred at the same time OUR dropped and osmolality rose in these cultures.

Figure 21:
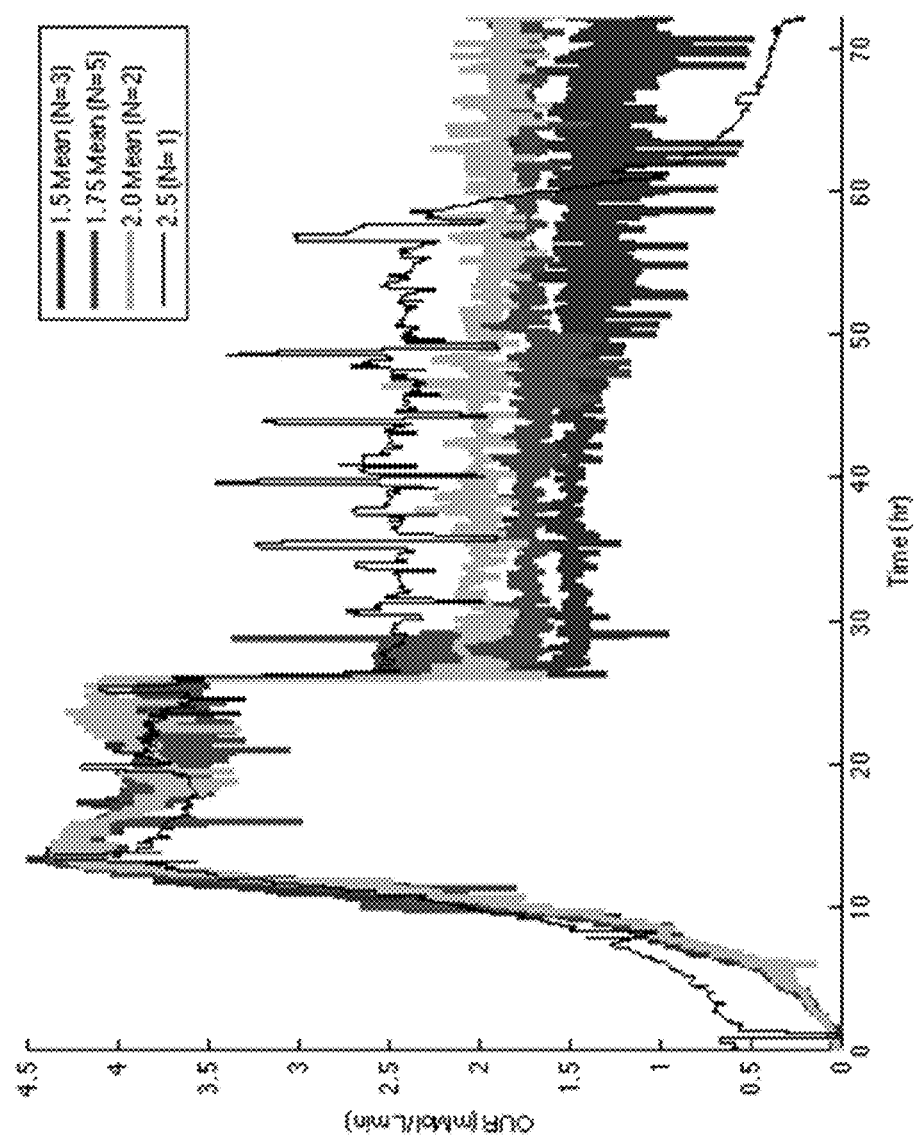
FIG. 21 shows the average OUR over time in cultures grown under agitation at 650 rpm for 26 hours, then shifted to a lower agitation rate sufficient to achieve the labeled OUR set point. Cells bore two vectors: a TIR2,2 vector expressing the xIL13 hAb and FkpA, and a vector expressing DsbA and DsbC in the absence of IPTG. Number of samples used for each condition is provided ("N").
Figure 22:
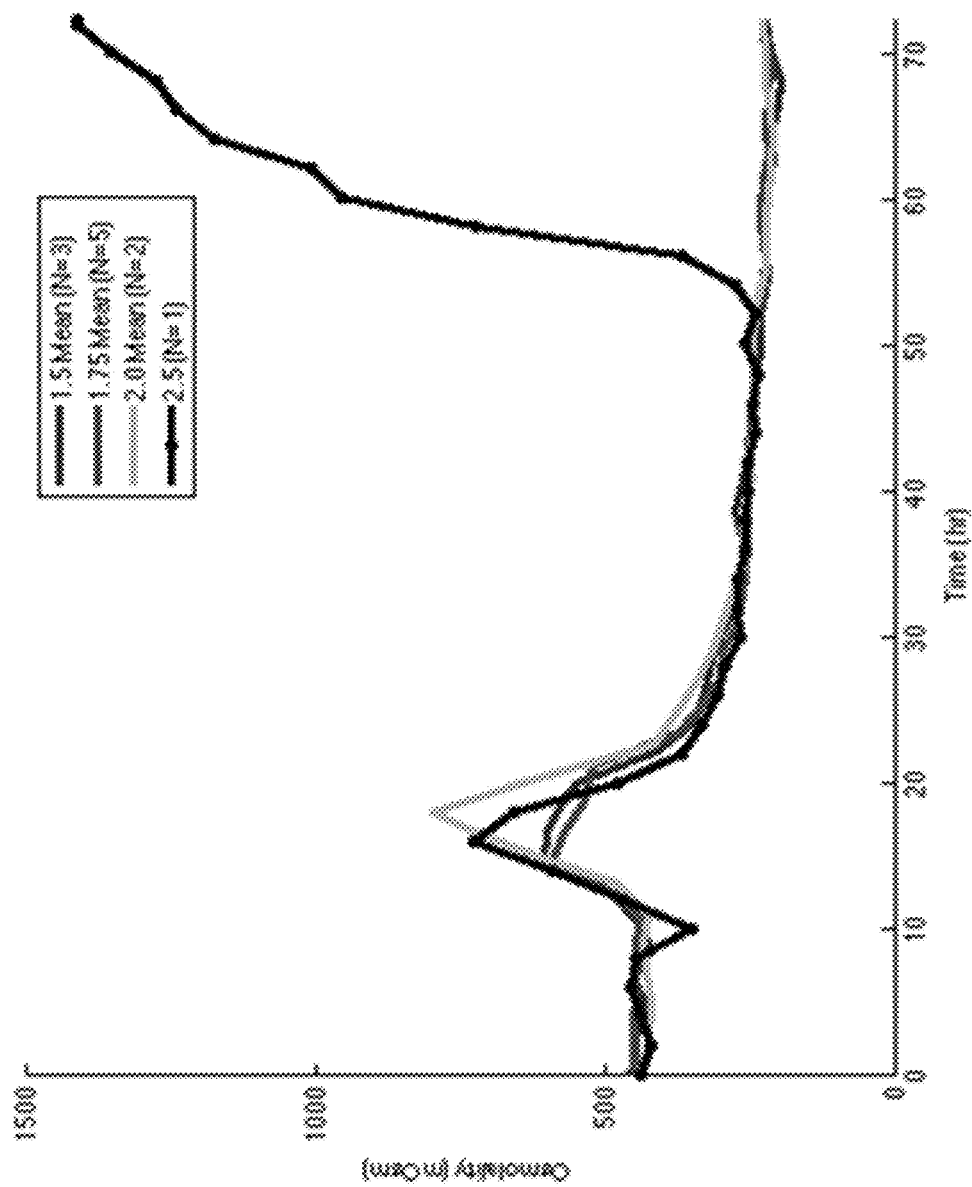
FIG. 22 shows the average osmolality over time in cultures grown under agitation at 650 rpm for 26 hours, then shifted to a lower agitation rate sufficient to achieve the labeled OUR set point. Cells bore two vectors: a TIR2,2 vector expressing the xIL13 hAb and FkpA, and a vector expressing in the absence of IPTG. Number of samples used for each condition is provided ("N").

To mitigate the drop in titer and eliminate the rise in osmolality, an agitation shift at 26 hours was evaluated with the non-induced TIR2,2 condition. The agitation rate was shifted from 650 rpm to a level that achieved a target OUR set point. Four different OUR target set points were tested: approximately 1.5, 1.75, 2.0 and 2.5 mmol/L/min. Agitation shifts with OUR set points between approximately 1.5 and 2.0 mmol/L/min eliminated the drop in OUR (FIG. 21) and the rise in osmolality (FIG. 22).

Figure 23:
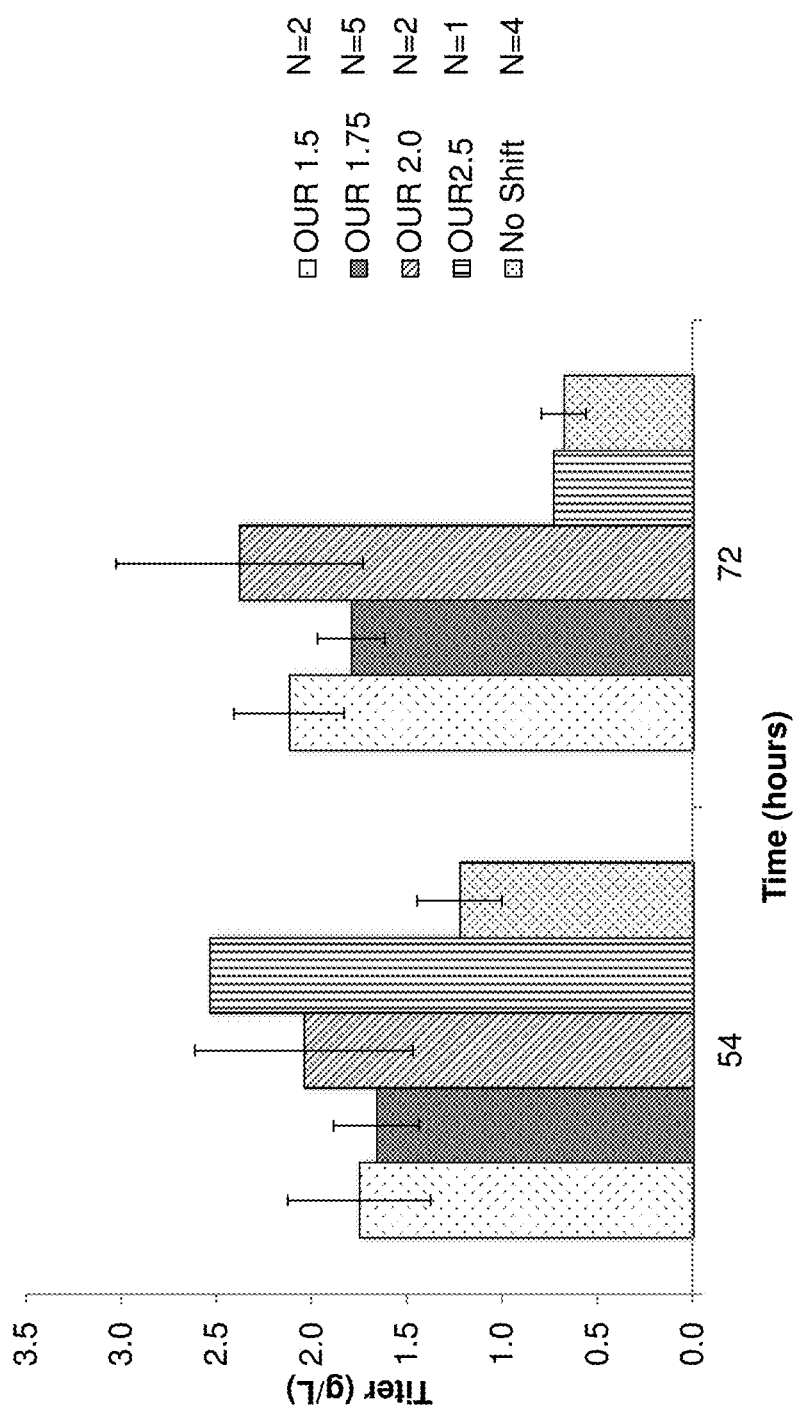
FIG. 23 shows the average titer of the xIL13 hAb production at two time points (54 and 72 hours) in cultures grown under agitation at 650 rpm for 26 hours, then shifted to a lower agitation rate sufficient to achieve the labeled OUR set point. Cells bore two vectors: a TIR2,2 vector expressing the xIL13 hAb and FkpA, and a vector expressing DsbA and DsbC in the absence of IPTG. Number of samples used for each condition is provided ("N").

Importantly, in all of the agitation shift conditions, the titer was higher than in the non-shifted condition at 54 hours (FIG. 23). In the approximate 2.5 mmol/L/min condition the OUR dropped at ~60 hours (FIG. 21) and the osmolality rose to a peak of 1200 mOsm at 72 hours (FIG. 22). At 72 hours, the approximate 2.5 mmol/L/min condition titer (0.7 g/L) dropped to similar levels as the non-shifted condition (0.6±0.1 g/L). The average titer for the approximate 2.0 mmol/L/min condition was the highest (2.4±0.6 g/L) of the four conditions tested; however, there was some variability in the titers and there appeared to be a slight decline in the OUR profile. The approximate 1.5 mmol/L/min condition had both reproduced average titers of 2.1±0.3 g/L, but again there appeared to be some variability in the OUR profile late in the fermentation. The approximate 1.75 mmol/L/min condition had both reproducible titers (1.8±0.2 g/L), as well as consistent OUR trends so it was chosen as the preferred set point.

These results demonstrate that shifting the agitation rate of cultures mitigates the observed decline in OUR and rise in osmolality. Importantly, these agitation shifts also allow enhanced hAb production titer, particularly at later production time points.

Example 3: Effect of Temperature on Half-Antibody Production

While the previous Examples demonstrate significant gains in hAb production, additional tests were undertaken to still further optimize the production process. Therefore, for xIL13 hAb production, the high performing single plasmid system described in Example 1 and the OUR set point of approximately 1.75 mmol/L/min described in Example 2 were used as starting points. The process was still further optimized to yield significantly greater production yields, as described below.

The fermentation process of a preferred embodiment of the present disclosure may be divided into two different segments: the growth phase and the production phase. In the growth phase, most nutrients are in excess, and the culture density increases rapidly. In the production phase, phosphate becomes limited, growth stops, and expression of the product of interest begins. The effect of temperature on hAb production was tested for each of these phases.

In combination with the temperature experiments a second host was evaluated. In these experiments the MD157 plasmid was transformed into the 67A6 production host. The genotype of the 67A6 strain is W3110 ΔfhuA ΔphoA ilvG+ Δprc spr43H1 ΔdegP ΔmanA lacIQ ΔompT ΔmenE742 degPS210A.

The 67A6 strain contains a knockin of a protease deficient allele of the degP gene (also known as htrA and ptd), which encodes DegP. DegP (also known as Protease Do) is a periplasmic serine protease required for survival at high temperatures. Additionally, DegP acts as a molecular chaperone. The substitution of a alanine for serine eliminates the proteolytic activity of DegP but does not affect its chaperone function (Spiess et al., Cell, 97:339-347, 1999).

Figure 24:
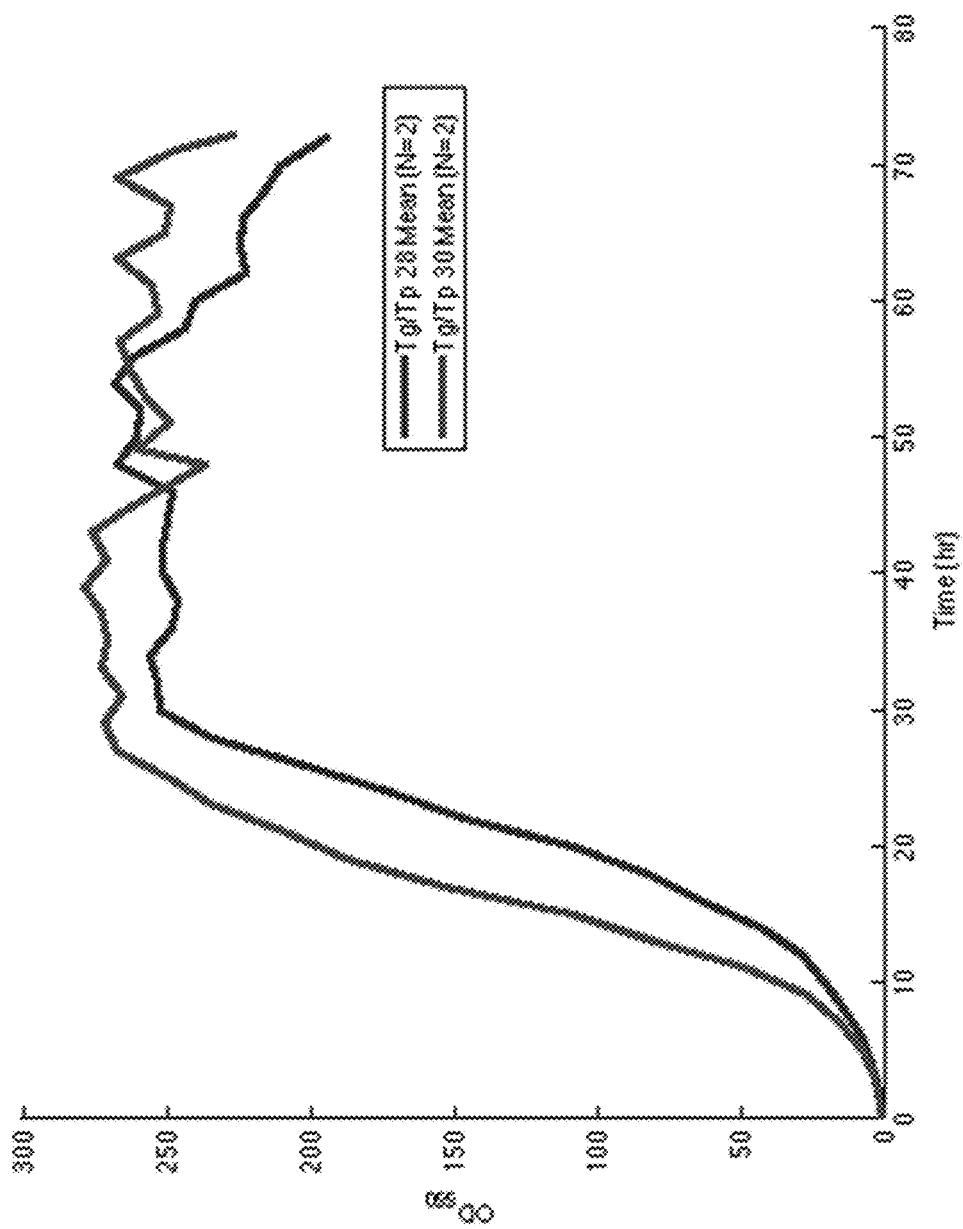
FIG. 24 shows the average cell density ($OD_{550\ nm}$) over time of cultures producing the xIL13 hAb from a TIR2,2 vector that also encoded FkpA driven by a phoA promoter and DsbA and DsbC driven by a tacII promoter in the absence of IPTG. Cultures were grown at a constant temperature for both growth and production (Tg/Tp) phases of either 28° C. or 30° C. An agitation shift was performed 26 hours into the fermentation. Number of samples used for each condition is provided ("N").
Figure 25:
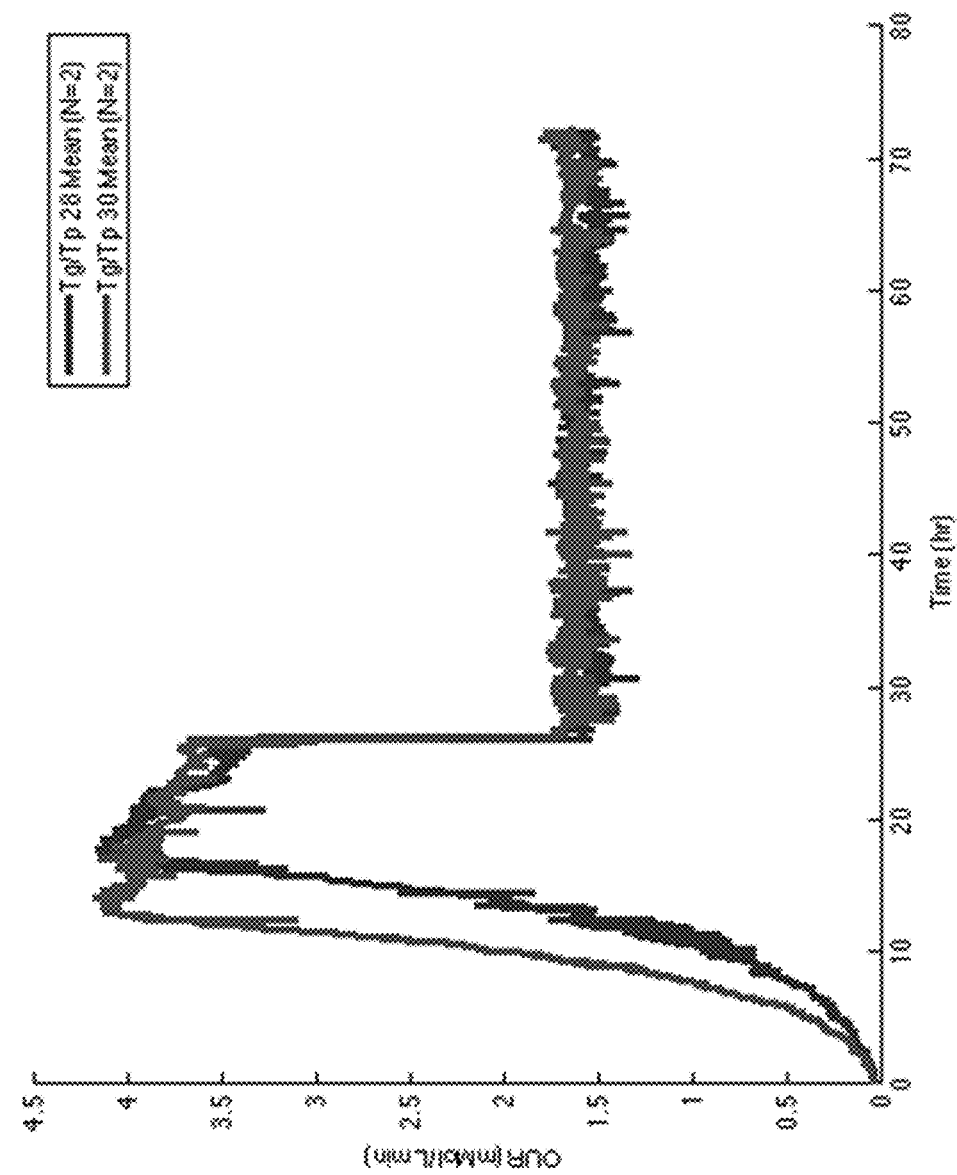
FIG. 25 shows the average OUR over time of cultures of cells producing the xIL13 hAb from a TIR2,2 vector that also encoded FkpA driven by a phoA promoter and DsbA and DsbC driven by a tacII promoter in the absence of IPTG. Cultures were grown at a constant temperature for both growth and production (Tg/Tp) phases of either 28° C. or 30° C. Number of samples used for each condition is provided ("N").

Temperature optimization was performed for both the growth phase (Tg) and production phase (Tp) for the xIL13 TIR2,2 single plasmid system. FIG. 24 shows the growth of cultures grown with a constant Tg/Tp of 30° C. or 28° C. A constant Tg/Tp of 28° C. resulted in a lag in growth rate as compared to the constant Tg/Tp of 30° C. FIG. 25 shows the OUR of cultures grown at these temperatures. Similar to growth rate, OUR is delayed when cultures are grown at a constant Tg/Tp of 28° C., as compared to 30° C.

Figure 26:
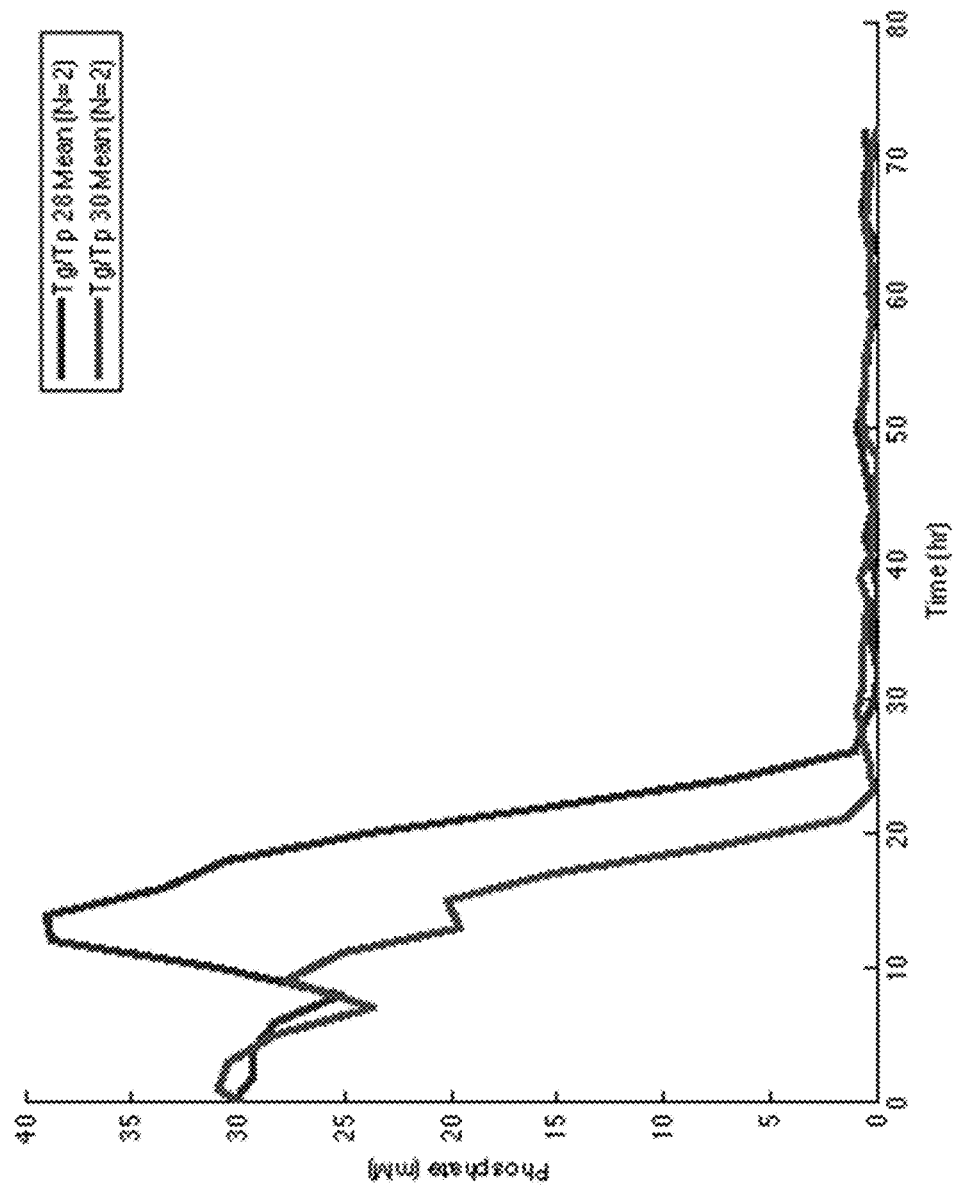
FIG. 26 shows the average phosphate concentration over time in cultures of cells producing the xIL13 hAb from a TIR2,2 vector that also encoded FkpA driven by a phoA promoter and DsbA and DsbC driven by a tacII promoter in the absence of IPTG. Cultures were grown at a constant temperature for both growth and production (Tg/Tp) phases of either 28° C. or 30° C. Number of samples used for each condition is provided ("N").

As shown in FIG. 26, phosphate was depleted at 22±2 hours using a constant Tg/Tp of 30° C. When the Tg/Tp was shifted down to 28° C., the growth rate of the culture was retarded as described above, and phosphate depletion was shifted to 26±2 hours.

Figure 27:
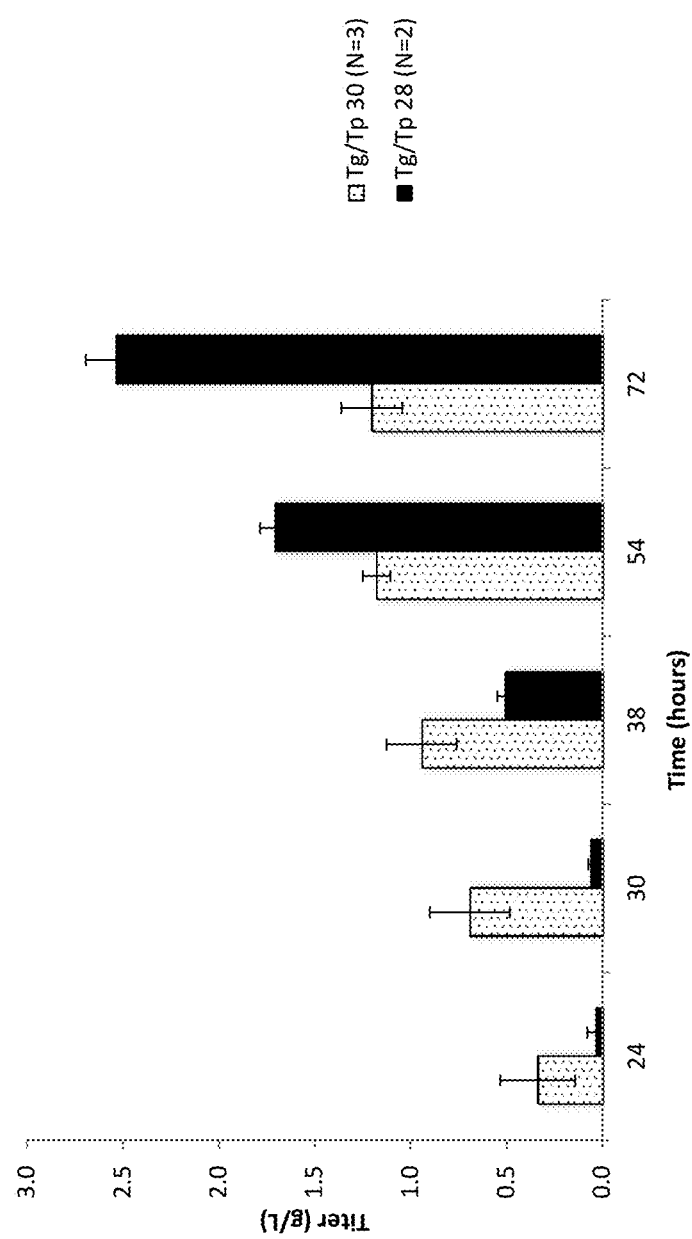
FIG. 27 shows the average titer of the xIL13 hAb produced in cultures of cells from a TIR2,2 vector that also encoded FkpA driven by a phoA promoter and DsbA and DsbC driven by a tacII promoter in the absence of IPTG. Cultures were grown at a constant temperature for both growth and production (Tg/Tp) phases of either 28° C. or 30° C.

FIG. 27 shows the xIL13 hAb production of these cultures. For each condition, product expression began at the time when phosphate depletion occurred. The constant 28° C. Tg/Tp condition achieved a final titer of 2.5±0.2 g/L, as compared to 1.3±0.2 g/L for the constant 30° C. Tg/Tp condition.

Figure 28:
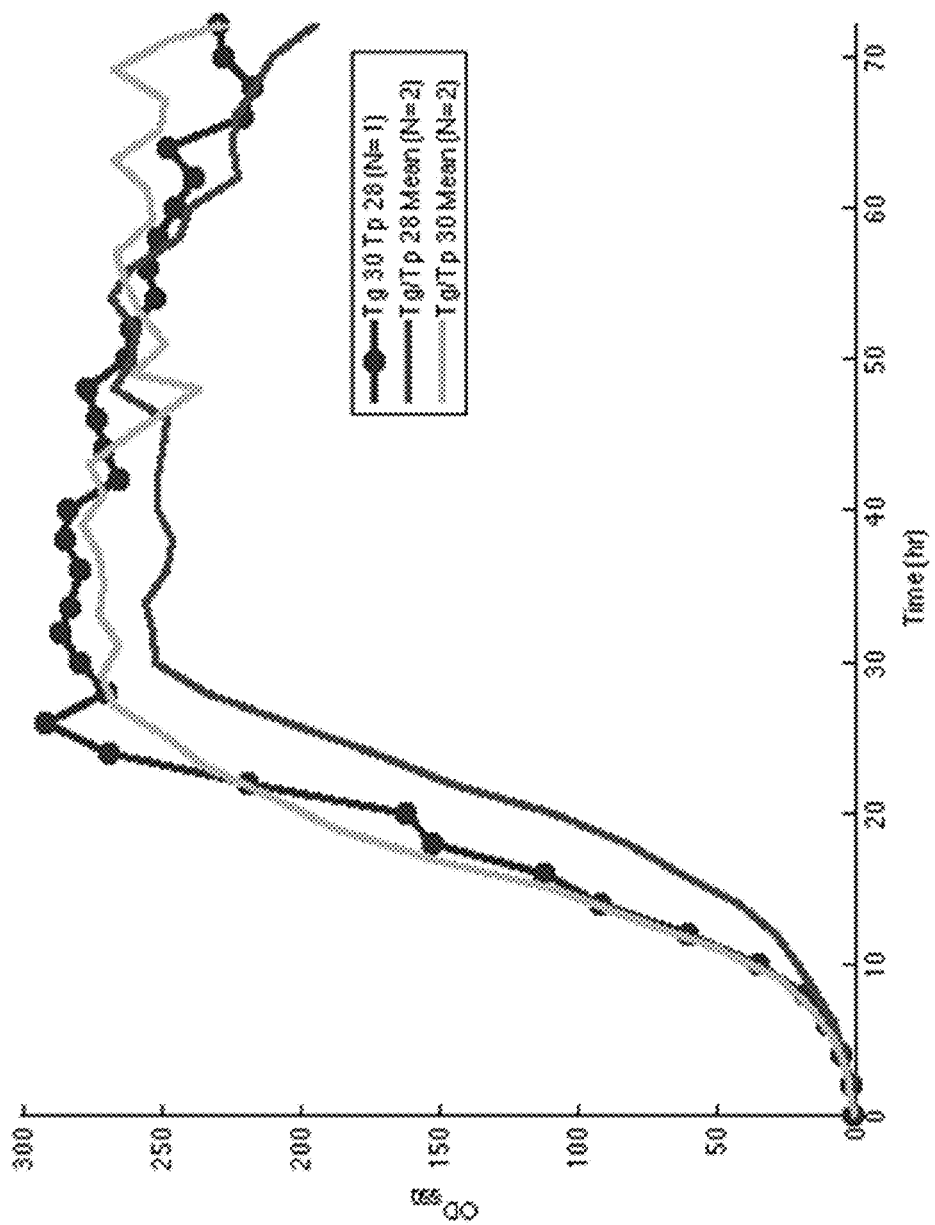
FIG. 28 shows the average cell density ($OD_{550\ nm}$) over time of cultures producing the xIL13 hAb from a TIR2,2 vector that also encoded FkpA driven by a phoA promoter and DsbA and DsbC driven by a tacII promoter in the absence of IPTG. Cultures were grown at a constant temperature of 28° C. or 30° C. (Tg/Tp 28° C. or Tg/Tp 30° C., respectively), or grown at 30° C. during the growth phase, then shifted to 28° C. for the production phase (Tg 30 Tp 28). Number of samples used for each condition is provided ("N").
Figure 29:
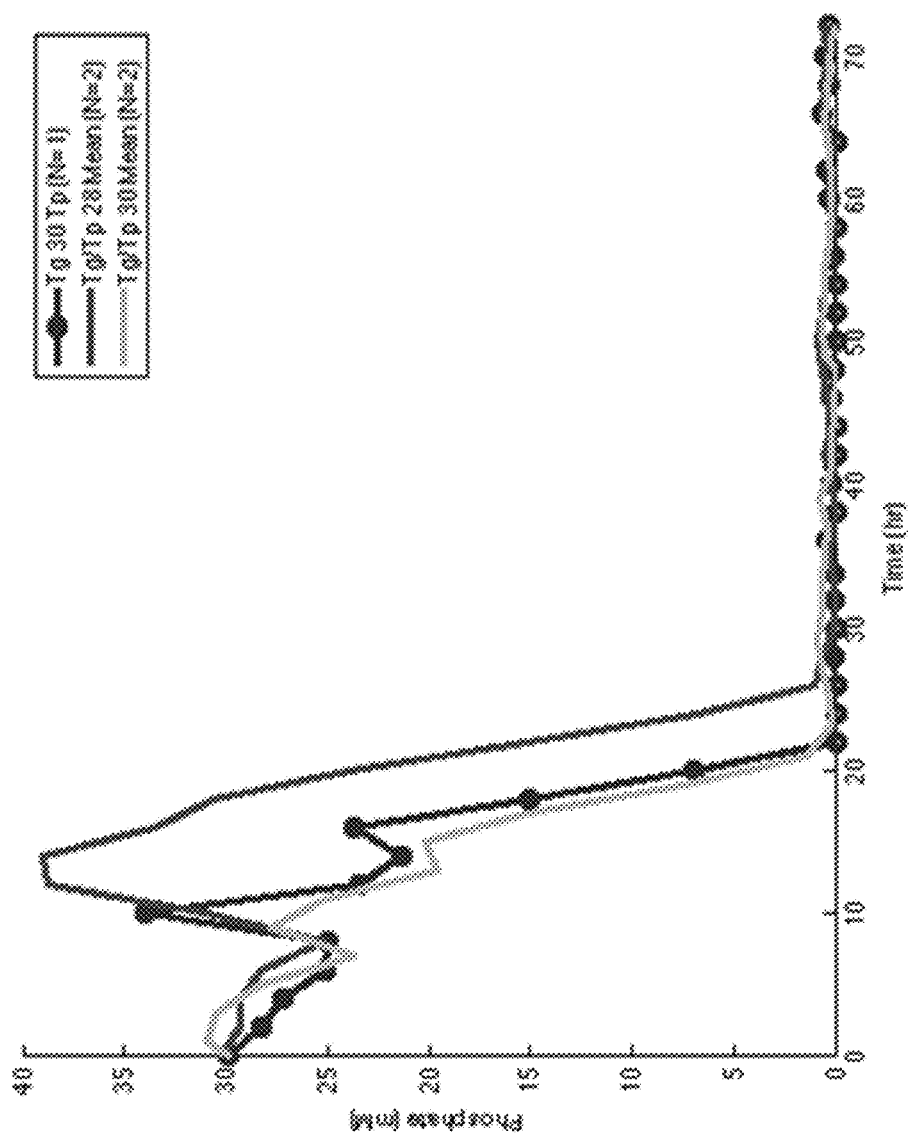
FIG. 29 shows the average phosphate concentration over time in cultures of cells producing the xIL13 hAb from a TIR2,2 vector that also encoded FkpA driven by a phoA promoter and DsbA and DsbC driven by a tacII promoter in the absence of IPTG. Cultures were grown at a constant temperature of 28° C. or 30° C. (Tg/Tp 28° C. or Tg/Tp 30° C., respectively), or grown at 30° C. during the growth phase, then shifted to 28° C. for the production phase (Tg 30 Tp). Number of samples used for each condition is provided ("N").
Figure 30:
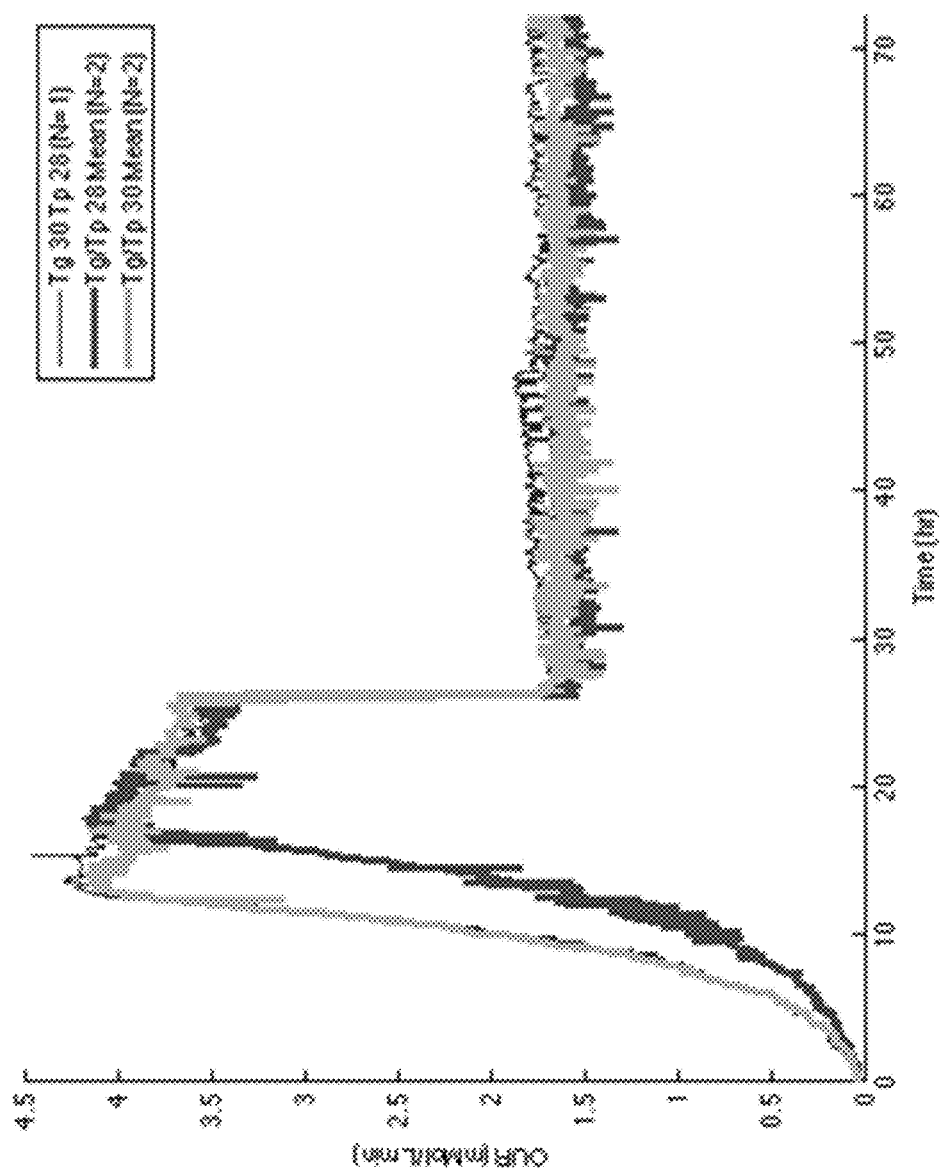
FIG. 30 shows the OUR over time of cultures of cells producing the xIL13 hAb from a TIR2,2 vector that also encoded FkpA driven by a phoA promoter and DsbA and DsbC driven by a tacII promoter in the absence of IPTG. Cultures were grown at a constant temperature of 28° C. or 30° C. (Tg/Tp 28° C. or Tg/Tp 30° C., respectively), or grown at 30° C. during the growth phase, then shifted to 28° C. for the production phase (Tg 30 Tp 28). Number of samples used for each condition is provided ("N").

In an effort to increase the amount of time in the production phase, a temperature shift strategy was tested. In this experiment the growth phase temperature was set at 30° C. and at 20 hours the temperature was shifted to 28° C. The growth (FIG. 28), phosphate (FIG. 29), and OUR (FIG. 30) profiles between 0 and 20 hours were similar for the Tg30/Tp28° C. shift and constant Tg/Tp 30° C. conditions.

Figure 31:
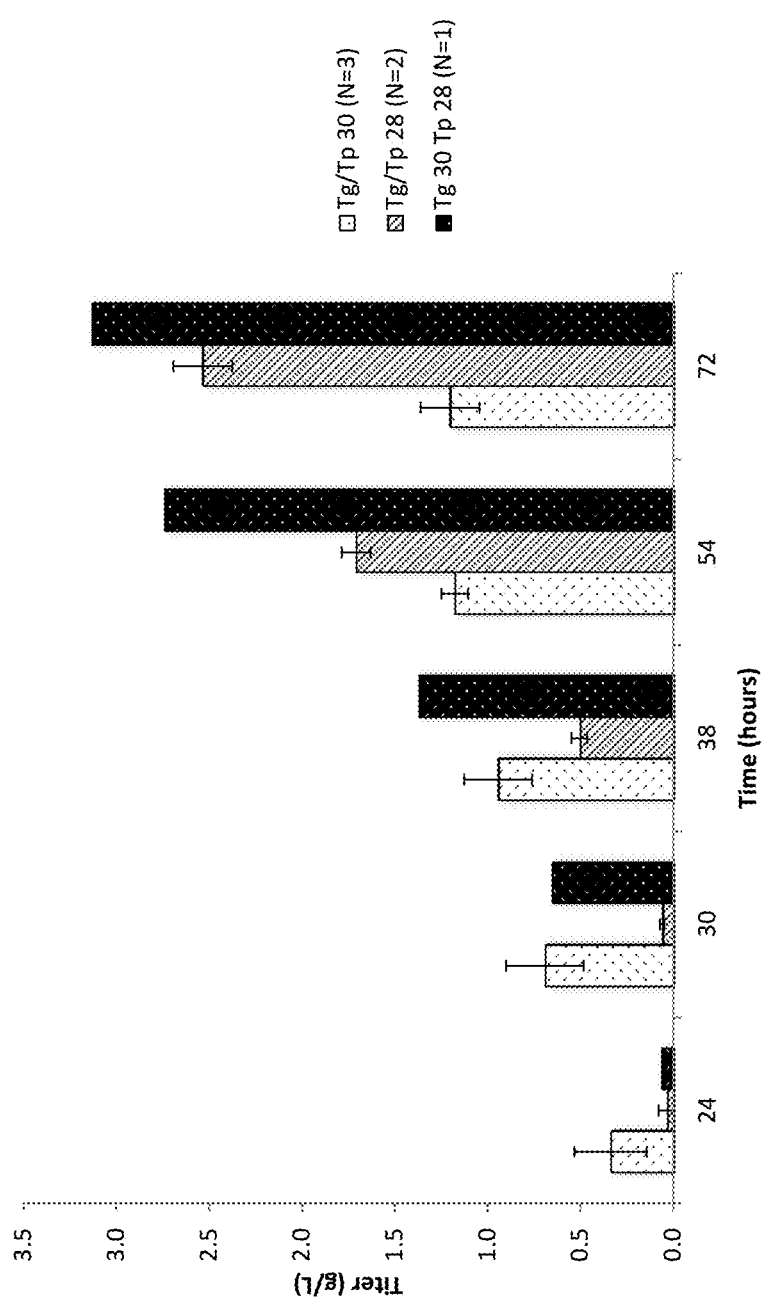
FIG. 31 shows the average titer of xIL13 hAb produced over time from a TIR2,2 vector that also encoded FkpA driven by a phoA promoter and DsbA and DsbC driven by a tacII promoter in the absence of IPTG. Cultures were grown at a constant temperature of 28° C. or 30° C., as labeled (Tg/Tp 28° C. or Tg/Tp 30° C., respectively), or grown at 30° C. during the growth phase, then shifted to 28° C. for the production phase (Tg 30 Tp 28).

As shown in FIG. 31, the use of a temperature shift to 28° C. at the time of product induction provided a further 0.6 g/L increase in titer, comparing a final titer of 3.1 g/L produced under the Tg30/Tp28° C. conditions to a final titer of 2.5 g/L produced under the constant Tg/Tp 28° C. condition. These results demonstrate that growing the culture at a higher temperature, then decreasing the culture temperature at the time of production can result in a significant increase in product formation.

A partial factorial design of experiment (DoE) was performed to determine the optimal operating conditions for the xIL13 hAb utilizing the 67A6 host strain. The DoE focused on three operating parameters and the level of FkpA.

TABLE 3-1 xIL13 hAb Parameters

| Pattern | Growth Temp. (Tg) | Production Temp. (Tp) | pH | FkpA promoter | Titer (g/L) |
|---------|-------------------|-----------------------|------|---------------|-------------|
| -+-+    | 30                | 28                    | 6.7  | phoA          | 2.8         |
| 0001    | 32                | 26.5                  | 6.85 | phoA          | 1.9         |
| ----    | 30                | 25                    | 6.7  | tac           | 1.4         |
| +-+-    | 34                | 25                    | 7    | tac           | 2.9         |
| +--+    | 34                | 25                    | 6.7  | phoA          | 4.6         |
| --++    | 30                | 25                    | 7    | phoA          | 1.8         |
| -++-    | 30                | 28                    | 7    | tac           | 1.6         |
| ++++    | 34                | 28                    | 7    | phoA          | 2.8         |
| ++--    | 34                | 28                    | 6.7  | tac           | 1.6         |
| 0002    | 32                | 26.5                  | 6.85 | phoA          | 3.3         |

As shown in Table 3-1, the operating parameters included Tg and Tp as well as pH. The pattern refers to the operating range for a specific parameter; (−) refers to a low value parameter, (+) refers to a high value parameter, and 0001 and 0002 refer to a center point parameter. The Tg ranged from 30 to 34° C., the Tp ranged from 25 to 28° C., and the pH ranged between 6.7 and 7.0. The amount of FkpA produced was modulated by the promoter used. High levels of FkpA were generated from the phoA promoter on MD157 and low levels of FkpA were generated from the non-induced tac promoter on KA01. Partial factorial analysis was performed by running 10 experiments.

Figure 32:
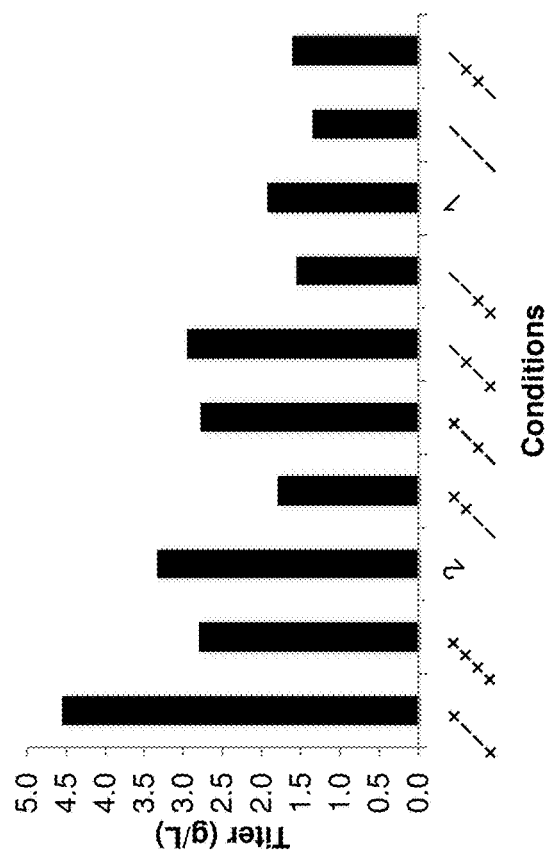
FIG. 32 shows the results of a partial factorial design of experiment (DoE) analysis of the xIL13 hAb titer with a single plasmid (MD157) under different process conditions identified by the pattern in the accompanying table.

As shown in FIG. 32, these factors had significant effects on the titer of xIL13 hAb produced. The titer of hAb produced by the conditions used for the DoE experiments described in Table 3-1 ranged from approximately 1.5 to approximately 4.5 g/L.

Figure 33:
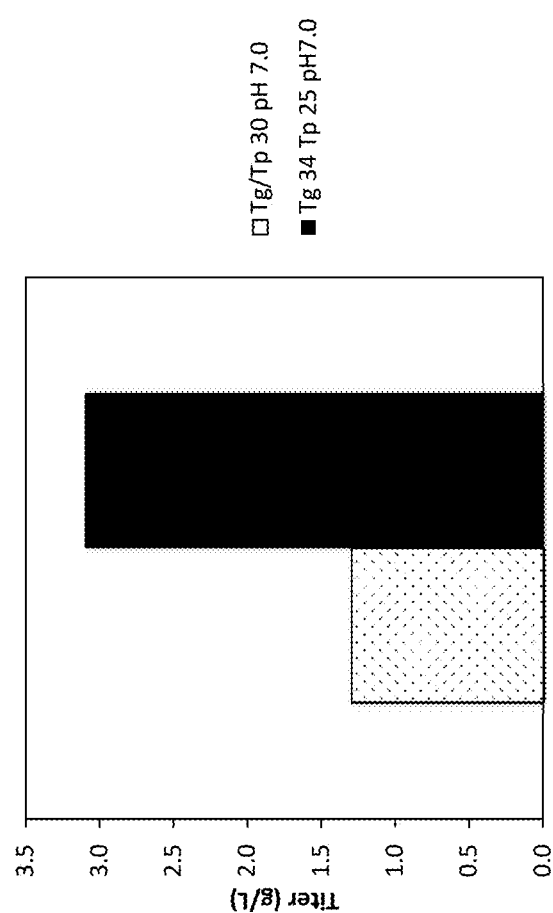
FIG. 33 shows the titer of xIL4 hAb produced from a TIR2,2 vector that also encoded FkpA, DsbA and DsbC driven by a tacII promoter in the absence of IPTG. Cultures were grown at a constant temperature of 30° C. (Tg/Tp 30° C.), or grown at 34° C. during the growth phase, then shifted to 25° C. for the production phase (Tg 34 Tp 25).

The xIL4 single plasmid (CB1) was tested with the optimal fermentation conditions identified from the xIL13 DoE (Tg 34° C., Tp 28° C., pH 7.0). However in the CB1 condition a tacII promoter without IPTG induction was used to drive FkpA expression. The xIL14 hAb titer was compared to a fermentation condition in which the Tg/Tp was held constant at 30° C. and the pH was maintained at 7.0. The xIL4 hAb titer increased from 1.3 g/L to 3.1 g/L with the new process conditions without the addition of IPTG (FIG. 33).

A partial factorial DoE was performed to determine the optimal operating conditions for the xIL17 hAb. The MD341 single plasmid was constructed by replacing the ORFs for the xIL13 hAb single plasmid (MD157) LC and HC with the ORF of the xIL17 LC and HC. The promoters used for the expression of the antibody fragments and chaperones were identical to the xIL13 (MD157) plasmid. The DoE focused on three operating parameters.

TABLE 3-2 xIL17 hAb Parameters

| Pattern | Growth Temp. (Tg) | Production Temp. (Tp) | pH | Titer (g/L) |
| --- | --- | --- | --- | --- |
| −+− | 30 | 30 | 6.7 | 0.38 |
| 0001 | 32 | 27.5 | 7.0 | 2.0 |
| −−− | 30 | 25 | 6.7 | 2.5 |
| −−+ | 30 | 25 | 7.3 | 2.6 |
| +−+ | 34 | 25 | 7.3 | 2.6 |
| 0002 | 32 | 27.5 | 7.0 | 1.9 |
| ++− | 34 | 30 | 6.7 | 0.34 |
| +−− | 34 | 25 | 6.7 | 2.0 |
| −++ | 30 | 30 | 7.3 | 0.2 |
| +++ | 34 | 30 | 7.3 | 0.12 |

Figure 34:
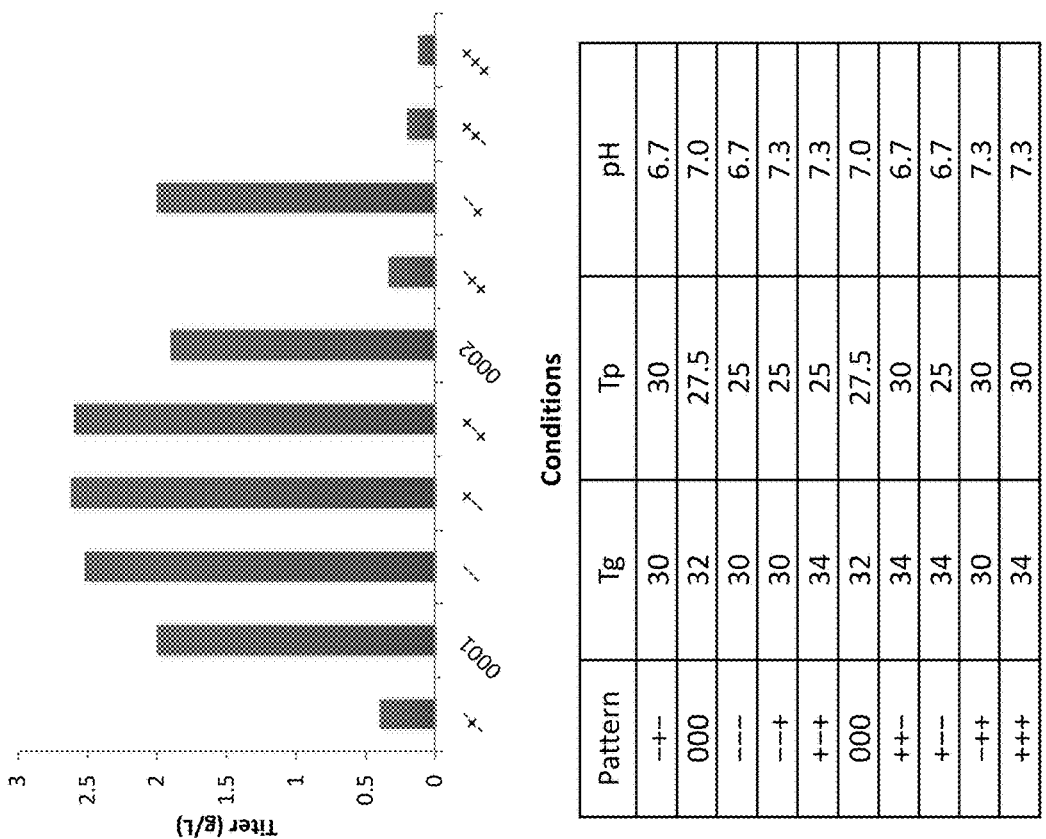
FIG. 34 shows the results of a partial factorial design of experiment (DoE) analysis of the xIL17 hAb titer with a single plasmid (MD341) under different process conditions identified by the pattern in the accompanying table.

As shown in Table 3-2 the operating parameters included Tg and Tp, as well as pH. The Tg ranged from 30 to 34° C., the Tp ranged from 25 to 30° C., and the pH ranged between 6.7 and 7.3. FIG. 34 shows that the most significant titer accumulation was achieved in conditions with a Tp of 25° C.

Figure 35:
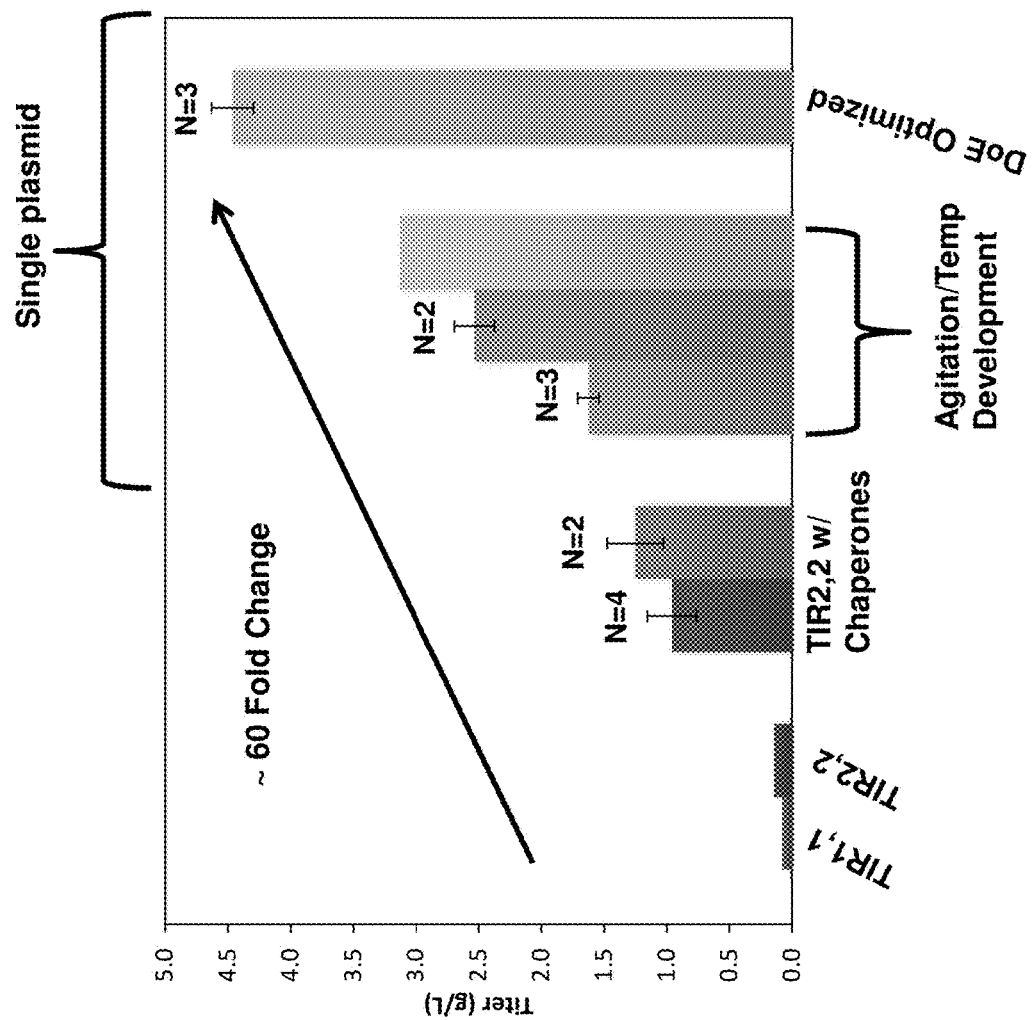
FIG. 35 shows the the effects of first optimizing chaperone protein co-expression and then optimizing the process steps (e.g., agitation rate, Tg, and Tp) on xIL13 hAb titer.

FIG. 35 shows the effects of first optimizing chaperone protein co-expression and then optimizing the process steps (e.g., agitation rate, Tg, and Tp) on production of xIL13 hAb titer. In an exemplary embodiment, molecular optimization (e.g., chaperone protein expression and vector characteristics) provided an approximately 16-fold increase in titer. This level of production was further enhanced by approximately 3.5-fold through process development (e.g., agitation rate, Tg, and Tp). Taken together, these results demonstrate that significant gains in production and robustness can be achieved through optimizing variables including chaperone expression, vector systems, agitation rate, pH, and growth/production temperatures. Ultimately, it was determined that the conditions with a Tg at 34° C., Tp at 25° C., a pH of 6.7, and the level of FkpA produced by the phoA promoter resulted in the highest xIL13 hAb titer.

Example 4: Effect of Host Strain on Half-Antibody Production

While the previous Examples demonstrate significant gains in hAb production, additional tests were undertaken to characterize the potential differences in hAb production between the host strains 66F8 and 67A6. Therefore, for hAb production, the high performing single plasmid system described in Example 1, the OUR shift described in Example 2, and the temperature shift described in Example 3 were evaluated in the two E. coli host strains: 66F8 and 67A6. The genotype of the 66F8 strain is W3110 ΔfhuA ΔphoA ilvG+ Δprc spr43H1 ΔdegP ΔmanA lacIQ ΔompT ΔmenE742. The genotype of the 67A6 strain is W3110 ΔfhuA ΔphoA ilvG+ Δprc spr43H1 ΔdegP ΔmanA lacIQ ΔompT ΔmenE742 degPS210A.

Figures 36A, 36B:
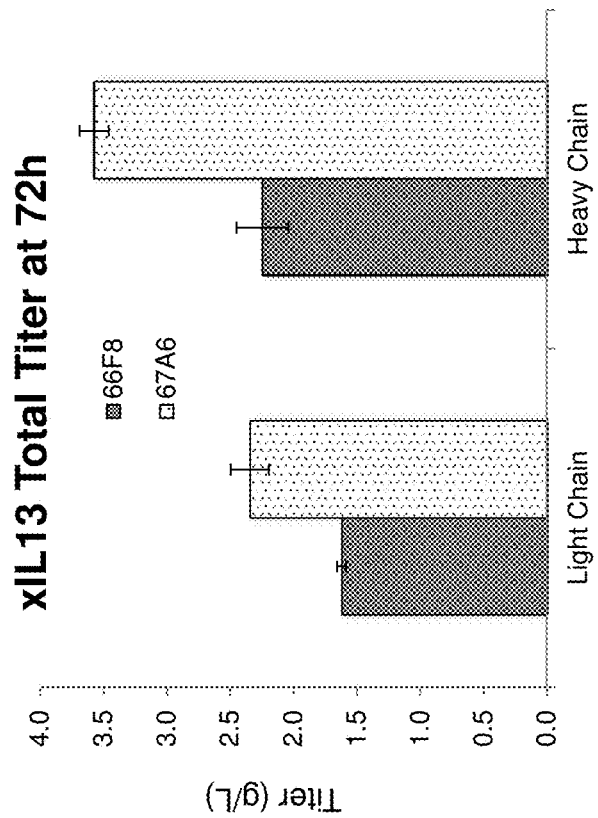
FIG. 36A shows the soluble xIL13 hAb titer from fermentations performed in the 66F8 and 67A6 host strains.
FIG. 36B shows the total xIL13 light chain and heavy chain concentrations at 72 hours in both the 66F8 and 67A6 host strains. N=2 for both conditions.

The xIL13 hAb was expressed in both the 66F8 and 67A6 host strains. Fermentations were performed under conditions employing temperature and agitation rate shifts as described above. The use of the 67A6 strain resulted in an increase in soluble xIL13 hAb titer (FIG. 36A) and in total subunit accumulation of both LC and HC as compared to the 66F8 strain (FIG. 36B).

Figure 37B:
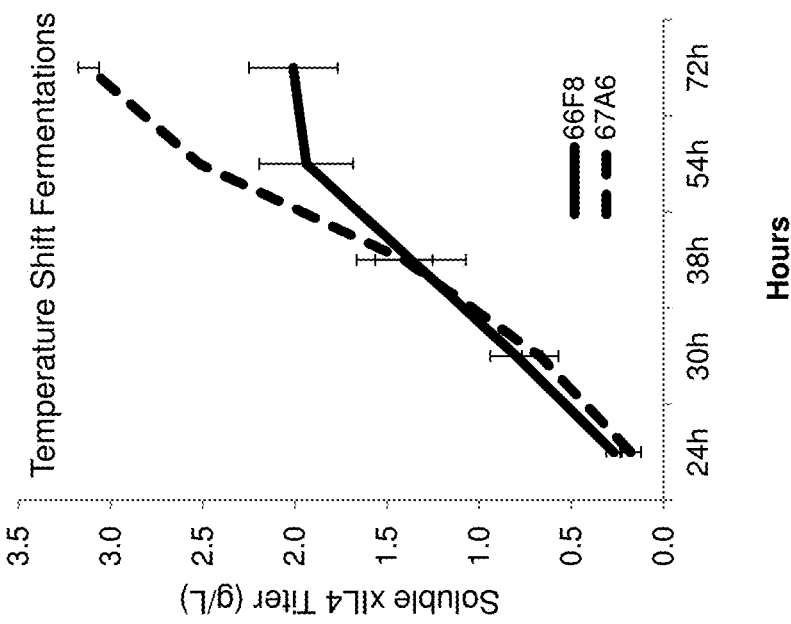
FIG. 37B shows the total soluble xIL4 hAb titer from fermentations performed in the 66F8 and 67A6 host strains under fermentation conditions employing a temperature shift. N=2 for both conditions.
Figure 37A:
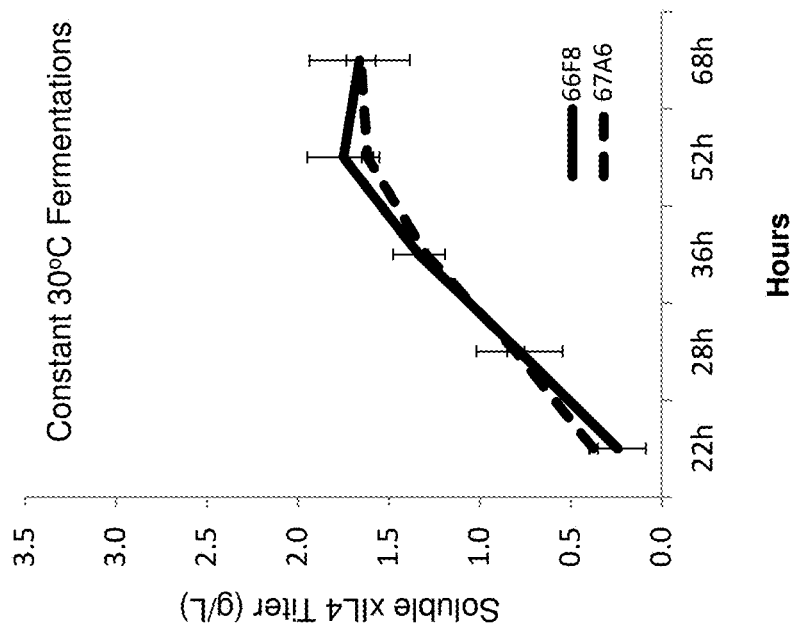
FIG. 37A shows the soluble xIL4 hAb titer from fermentations performed in the 66F8 and 67A6 host strains at a constant fermentation temperature.
Figure 38B:
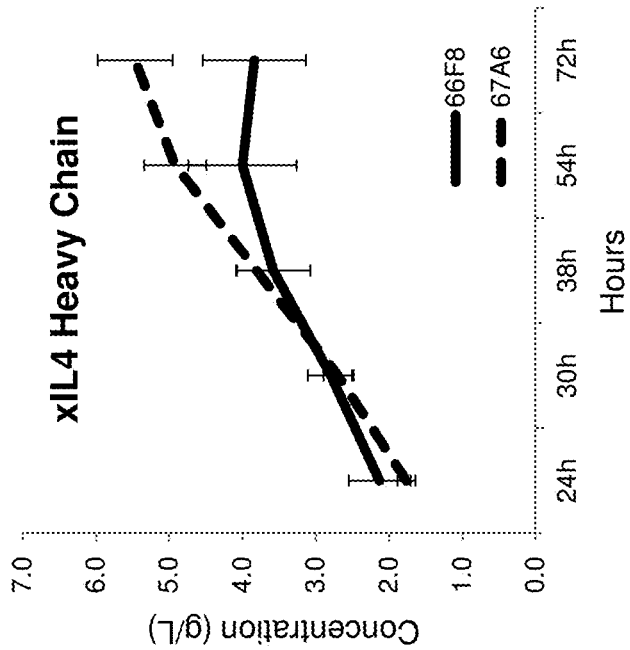
FIG. 38A shows the xIL4 light chain titer and FIG. 38B shows the xIL4 heavy chain titer from fermentations performed in the 66F8 and 67A6 host strains under fermentation conditions employing a temperature shift. N=2 for both conditions.
Figure 38A:
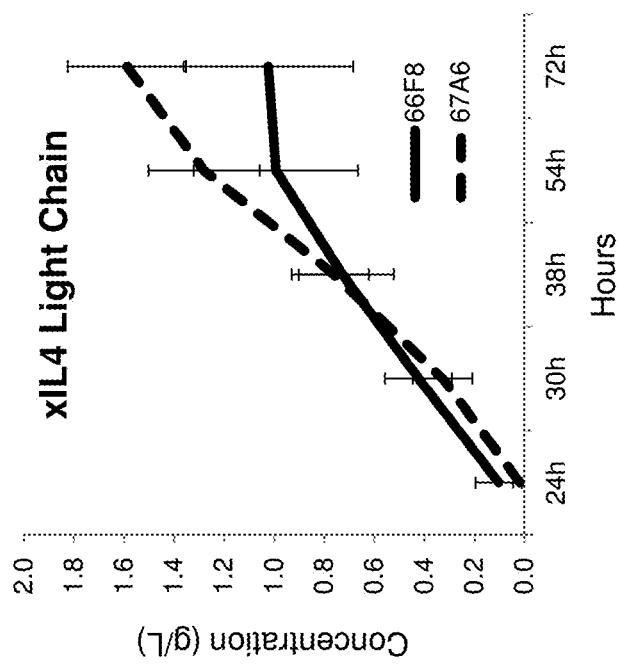

The xIL4 hAb was also expressed in both the 66F8 and 67A6 host strains. When the xIL4 hAb fermentations were performed at a constant temperature of 30° C., similar titers of about 1.5 g/L were obtained from both strains (FIG. 37A). However, under fermentation conditions in which the Tg was reduced from 34° C. to a Tp of 25° C. the 67A6 strain produced an average of 3.0 g/L and the 66F8 strain produced an average of 2.0 g/L (FIG. 37B). In addition, the total subunit accumulation of both LC and HC in the 67A6 fermentations was greater than in the 66F8 fermentations under conditions employing a temperature shift (FIG. 38A and FIG. 38B).

Thus, both xIL13 hAb and xIL4 hAb are two examples of a titer benefit provided by the 67A6 host strain and a decreased production temperature relative to the growth temperature. Without being bound by theory, recombinant protein accumulation appeared to plateau in host strains devoid of DegP, while in the host strain with the mutant DegPS210A, recombinant protein appeared to accumulate until the fermentation ended.

Figure 39:
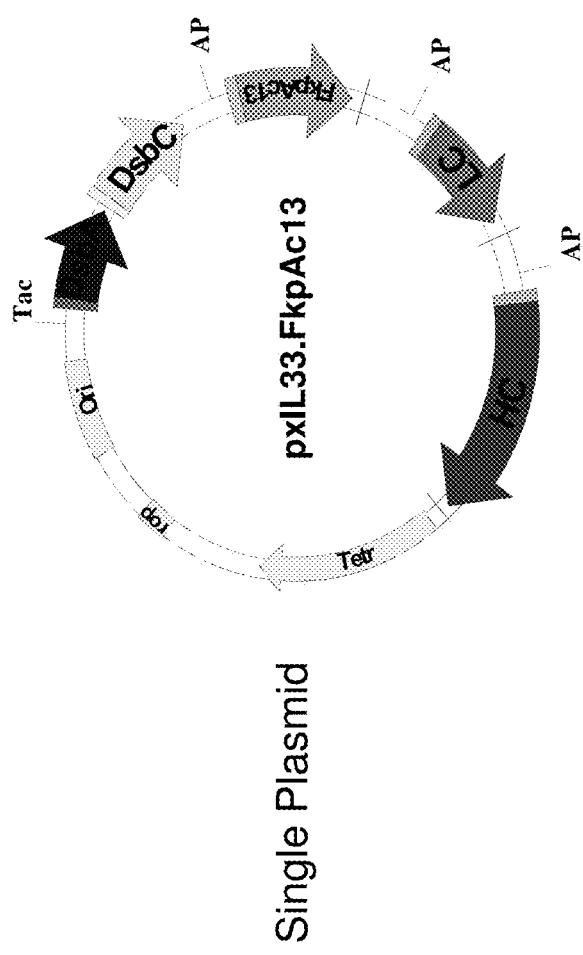
FIG. 39 provides a map of the xIL33 hAb secretion plasmid. LC and HC open reading frames were independently placed in operable combination with TIR2.

Example 5: Production of xIL33 hAb Using an Optimized Expression Vector and Optimized Culture Conditions The xIL33 hAb (MD501 plasmid) was constructed by replacing the ORFs for the xIL13 hAb single plasmid (MD157) LC and HC with the ORF of the xIL33 LC and HC. The promoters used for the expression of the antibody fragments and chaperones were identical to the xIL13 (MD157) plasmid (FIG. 39). A single fermentation was performed with an xIL33 hAb expression vector that contained only the ORFs for the xIL33 LC and HC (MD481). The MD481 plasmid did not contain ORFs for the molecular chaperones DsbA, DsbC or FkpA. The fermentation was performed at a constant temperature of 30° C., pH of 7.0, and an agitation rate of 650 RPM (base case of FIG. 40). Next, a single fermentation was performed with an xIL33 hAb expression vector that contained ORFs for the xIL33 LC and HC, as well as ORFs for the molecular chaperones DsbA, DsbC or FkpA (MD501). The same operating conditions were used for the MD501 fermentation as for the MD481 fermentation. The use of the single plasmid (MD501) resulted in an approximate 10-fold increase in xIL-33 hAb titer as compared to the base case.

A partial factorial DoE was performed to determine the optimal culture conditions for the xIL33 hAb MD501 single plasmid. The DoE focused on four parameters in a fractional factorial with 10 experiments including two center point replicates in the 67A6 host (Table 5-1). Agitation rate and temperature shifts were done at $OD_{550}$ of 150.

TABLE 5-1 xIL33 hAb Parameters

| Pattern | Growth Temp. (Tg) | Production Temp. (Tp) | pH | Target OUR | Titer (g/L) |
| --- | --- | --- | --- | --- | --- |
| −++− | 34 | 30 | 6.7 | 1.9 | 2.7 |
| −−++ | 30 | 30 | 6.7 | 2.8 | 1.7 |
| +−+− | 30 | 30 | 7.3 | 1.9 | 3.2 |
| 0000 | 32 | 27.5 | 7.0 | 2.3 | 4.1 |
| −+−+ | 34 | 25 | 6.7 | 2.8 | 3.0 |
| +−−+ | 30 | 25 | 7.3 | 2.8 | 3.3 |
| ++−− | 34 | 25 | 7.3 | 1.9 | 3.2 |
| 0000 | 32 | 27.5 | 7.0 | 2.3 | 4.0 |
| ++++ | 34 | 30 | 7.3 | 2.8 | 2.6 |
| −−−− | 30 | 25 | 6.7 | 1.9 | 2.5 |

Figure 40:
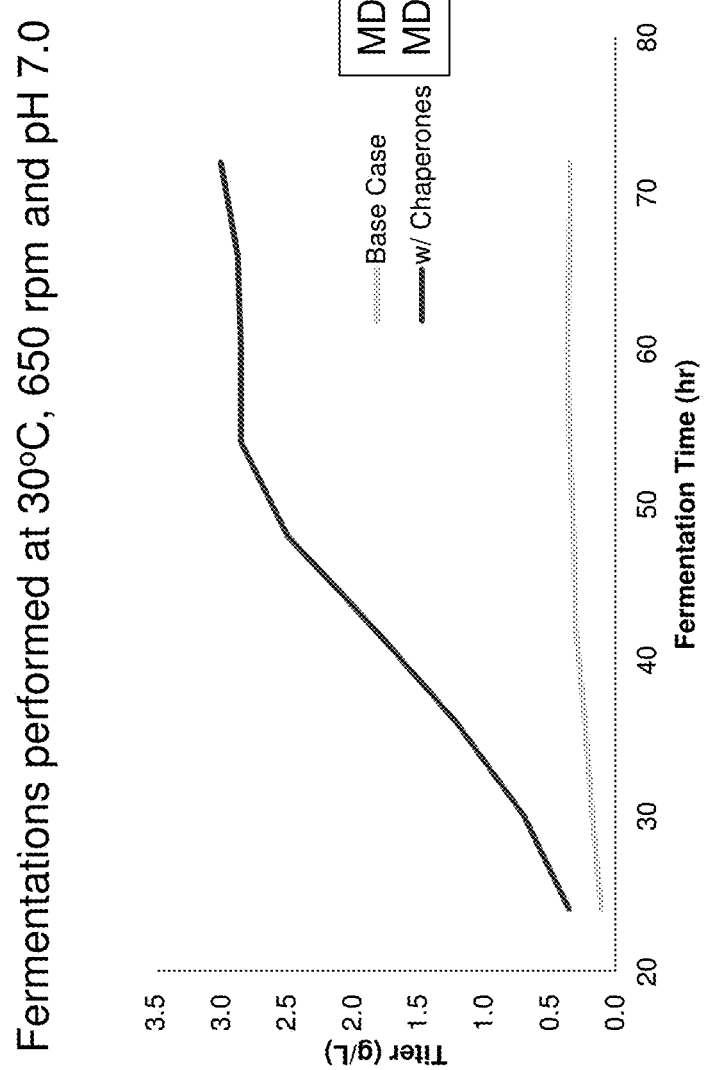
FIG. 40 illustrates accumulation of xIL33 hAb in fermentations performed in the absence of co-expression of the chaperones DsbA, DsbC, FkpA at a constant temperature of 30° C. (base case), and in fermentations performed in the presence of the chaperones DsbA, DsbC and FkpA co-expression under the same process conditions (w/ Chaperones).
Figure 41:
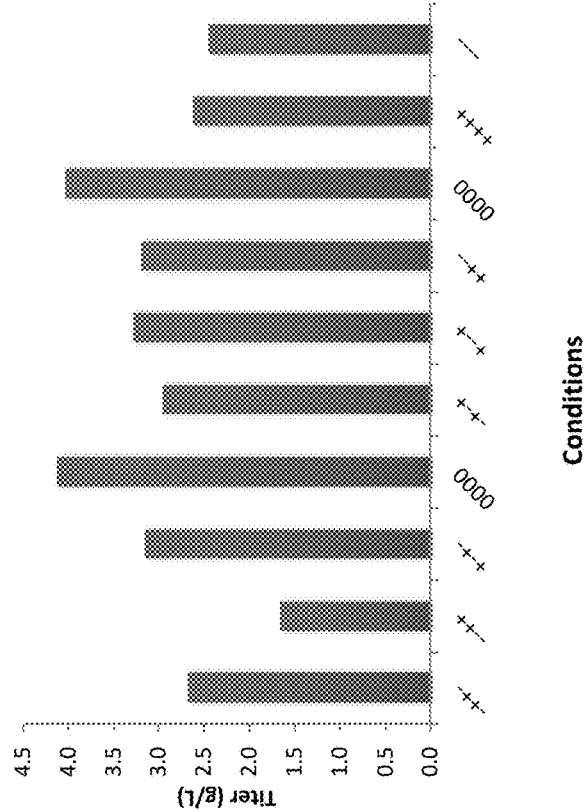
FIG. 41 shows the aIL33 hAb titer differences from the Design of Experiment (DoE) performed with the xIL33 hAb single plasmid containing the chaperones FkpA, DsbA, DsbC. DoE factors included pH, growth temperature (Tg), production temperature (Tp), and production phase target oxygen uptake rate (OUR).

As shown in Table 5-1, the Tg ranged from 30 to 34° C., the Tp ranged from 25 to 30° C., the pH ranged between 6.7 and 7.3, and the OUR set point ranged from 1.9 to 2.8 mmol $O_2$/L/min. FIG. 41 shows that the center point conditions provided the most significant benefit to titer with the highest titer achieved being 4.0±0.05 g/L, which amounts to a further increase in hAb titer as compared to the base case operating conditions (FIG. 40). The best culture conditions included a pH of 7.0, a Tg of 32° C., a Tp of 27.5° C. (2 hr ramp), and a target OUR of approximately 2.3 mmol/Lmin (2 hr agitation rate ramp).

Example 6: FkpA Optimization

Figure 42:
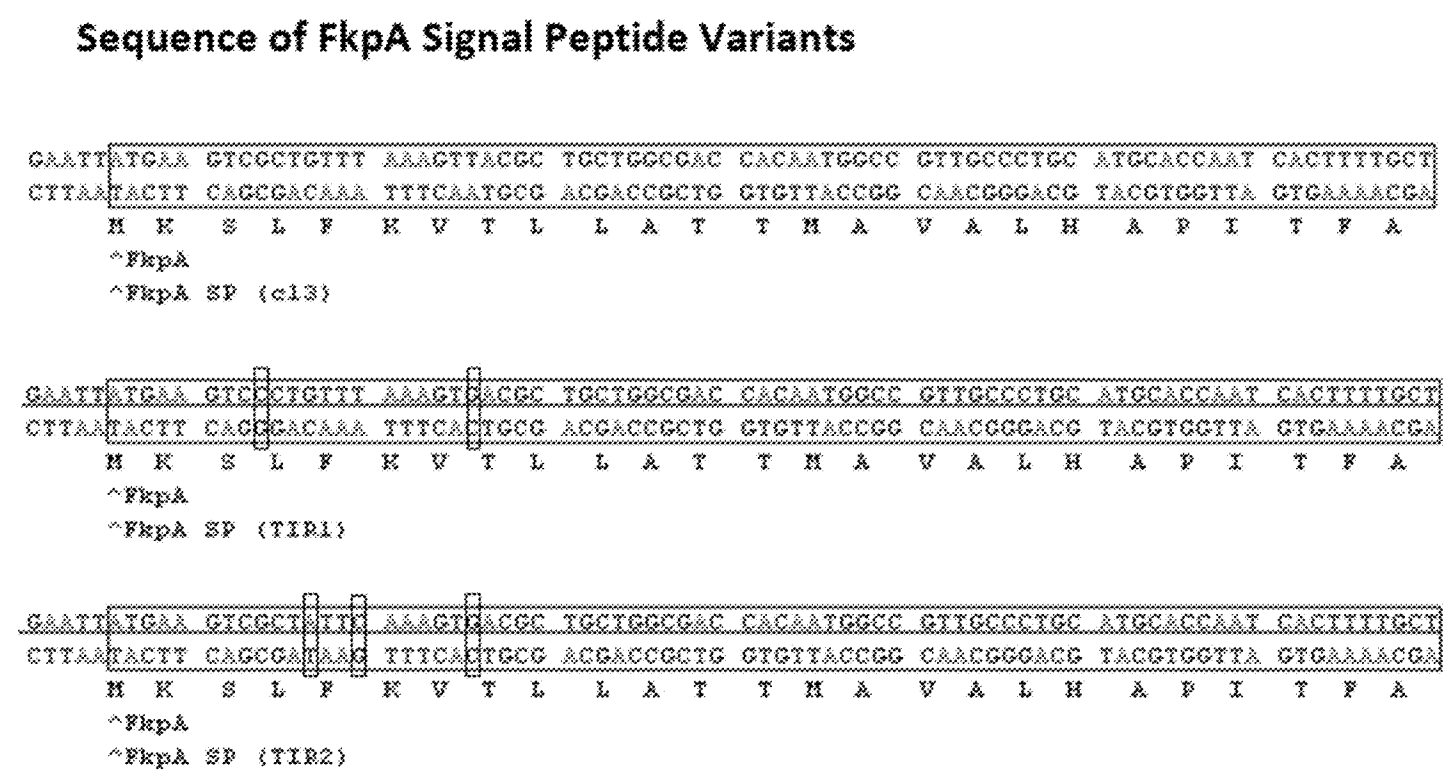
Figure 43:
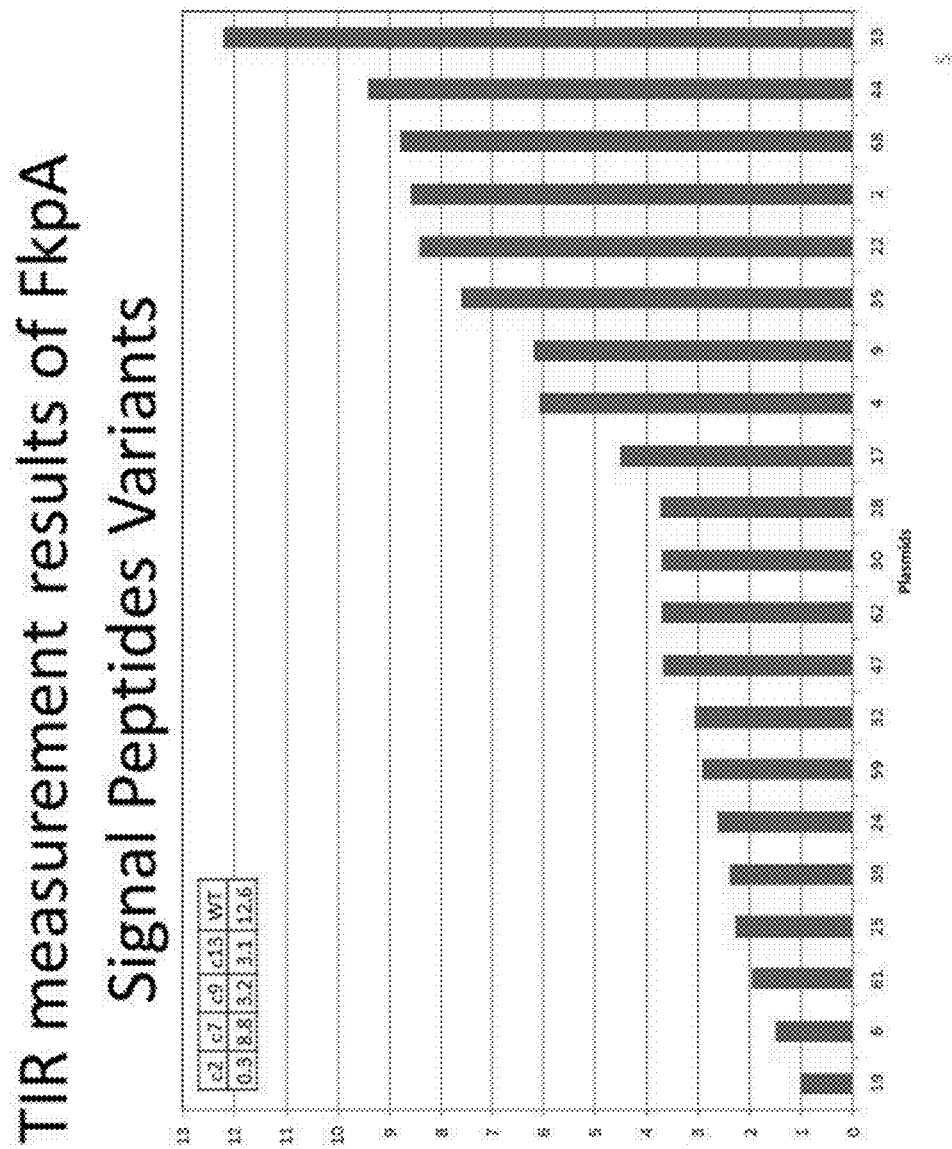
FIG. 43 shows the quantitative strength of the FkpA TIR variants relative to the TIR1 FkpA variant (plasmid 19).

In an effort to optimize the expression levels of FkpA, two additional FkpA TIR variants were tested in the single plasmids for xIL13, xIL17 and xIL33 hAbs (MD157, MD341 and MD501 plasmids). FkpA TIR variants were characterized as described in comparison to the endogenous FkpA signal sequence (FIG. 42). The MD157, MD341 and MD501 plasmids incorporated the ORF for FkpAc13, which was correlated with a TIR strength of three (FIG. 43). In the MD157, MD341 and MD501 single plasmids the FkpAc13 ORF was replaced with the FkpA TIR1 or TIR2 ORF and tested in the previously identified optimized fermentation conditions for each hAb.

Figure 44:
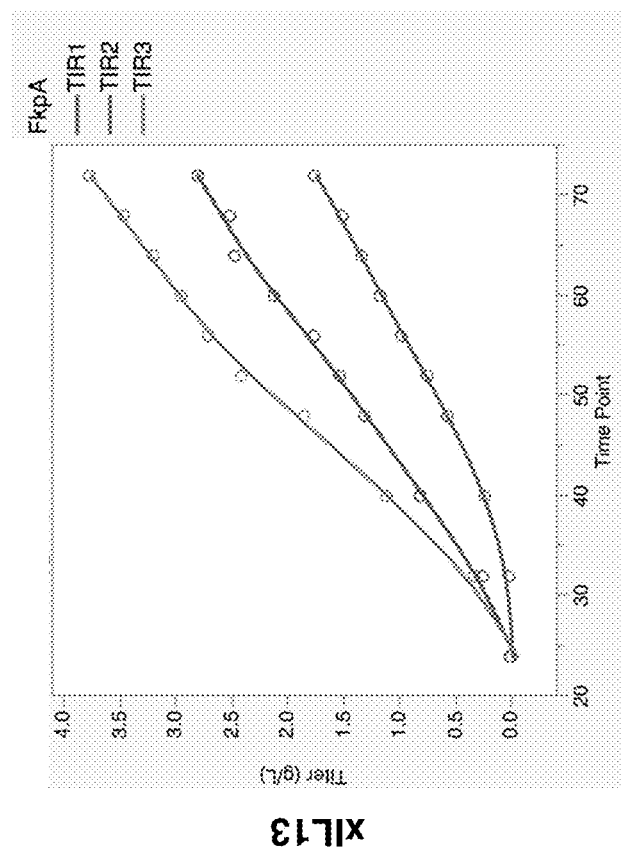
FIG. 44 shows the accumulation of the xIL13 hAb in fermentations performed with the TIR1, TIR2 and TIR3 FkpA TIR variants. The titer produced in each condition was 1.5, 2.5 and 4.0 g/L for the TIR1, TIR2 and TIR3 variants, respectively.

Increased levels of FkpA expression correlated with increased xIL13 hAb accumulation (FIG. 44). The FkpA TIR1 and TIR2 conditions resulted in final FkpA amounts of 0.5 and 2.5 g/L and xIL13 hAb titers of 1.5 and 2.5 g/L, respectively. The TIR 3 condition produced 4 g/L of FkpA and 3.8 g/L of hAb. Levels of FkpA expression also had an impact on the production phase OUR profiles. Overall the titration of FkpA increased the amount of hAb produced by about 3 fold.

Figure 45:
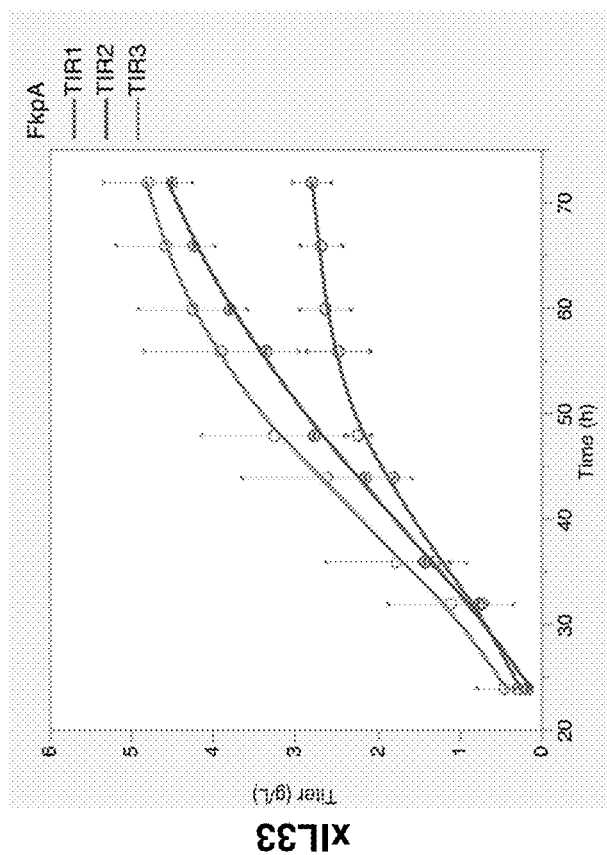
FIG. 45 shows the accumulation of the xIL33 hAb in fermentations performed with the TIR1, TIR2 and TIR3 FkpA TIR variants.

In the xIL33 hAb fermentations, the lowest titer accumulation profile correlated with the FkpA TIR1 condition with an end of run titer of 2.4 g/L (FIG. 45). The xIL33 TIR2 and TIR3 conditions resulted in an approximate 2 fold increase in xIL33 hAb titer (FIG. 45) when compared to the TIR1 condition. The data suggest that increased levels of FkpA are beneficial to hAb production.

Figure 46:
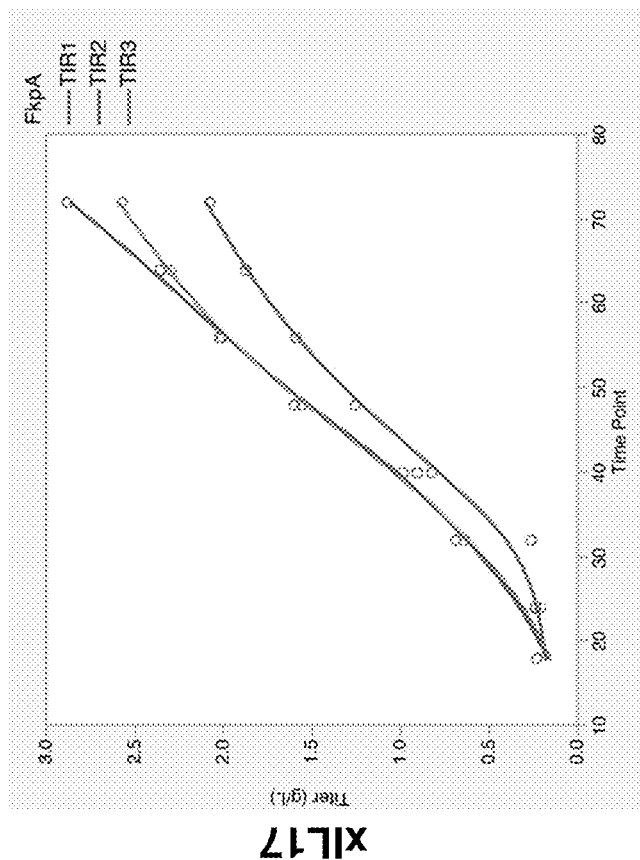
FIG. 46 shows a plot of the accumulation of the xIL17 hAb in fermentations performed with the TIR1, TIR2 and TIR3 FkpA variants.

In the xIL17 hAb fermentations, the lowest titer accumulation profile correlated with the FkpA TIR1 condition with an end of run titer of 2.0 g/L (FIG. 46).

Figures 47A, 47B:
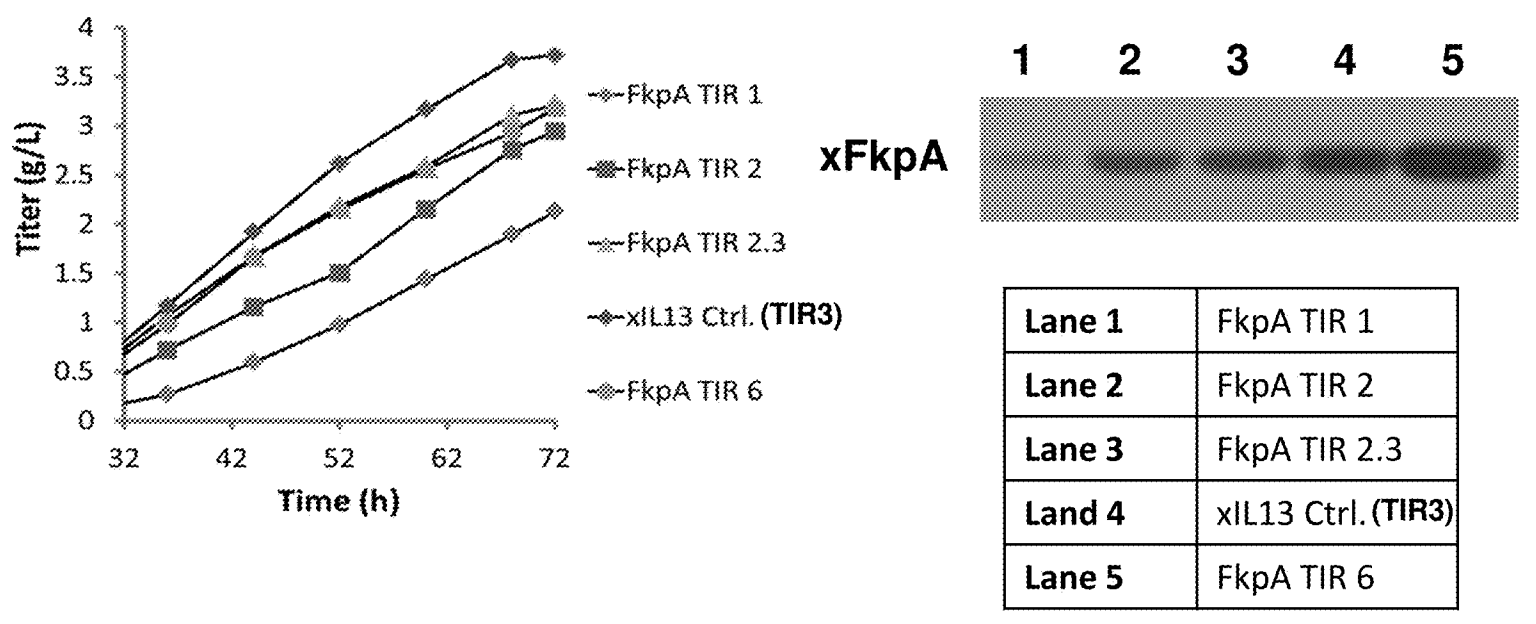

Two additional FkpA TIR variants were tested (TIR2.3 and TIR6) using the previously described best conditions for the xIL13 hAb. The TIR2.3 titer profile trended higher than the previously tested TIR2 condition, but was still lower than the control TIR3 condition (FIG. 47A). The TIR6 condition resulted in a titer accumulation profile similar to the TIR 2.3 condition, but again lower than the TIR3 control. FkpA accumulation as determined by western blot analysis showed the titration of FkpA across the TIR variants (FIG. 47B). The data suggests there is an optimal amount of FkpA expression that correlates with hAb production, which in the case of the xIL13 hAb (MD157 single plasmid) is TIR3.

Example 7: Effect of Oxygen Transfer Rate (OTR) Conditions

The xIL13 hAb best conditions identified in Example 3, were also tested with a second OTR strategy. In the experiments (N=3) the vessel backpressure (BP) and sparge rates were decreased from 1.0 to 0.3 bar and 20 to 13 SLPM, respectively. In an effort to recover the loss in OTR due to the decreases in back pressure and sparge rate, the growth and production phase agitation rates were increased from 650 to 880 RPM and 475 to 650 RPM. Different combinations of vessel backpressure, sparge rates, and agitation rates can be used to achive similar OTR conditions as those cited in previous examples.

Figure 48A:
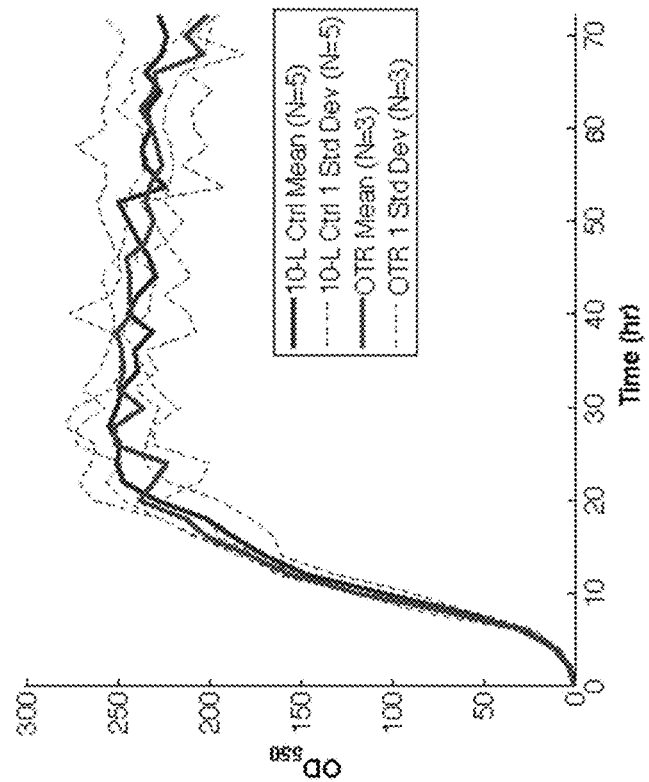
FIG. 48A shows the oxygen uptake rates (OUR) for the altered oxygen transfer rate (OTR) and control fermentation conditions. The altered OTR and control fermentations achieved a similar peak OUR of about 5 mmol/L/min and similar post agitation shift target OUR of 2.75 mmol/L/min.
Figure 48B:
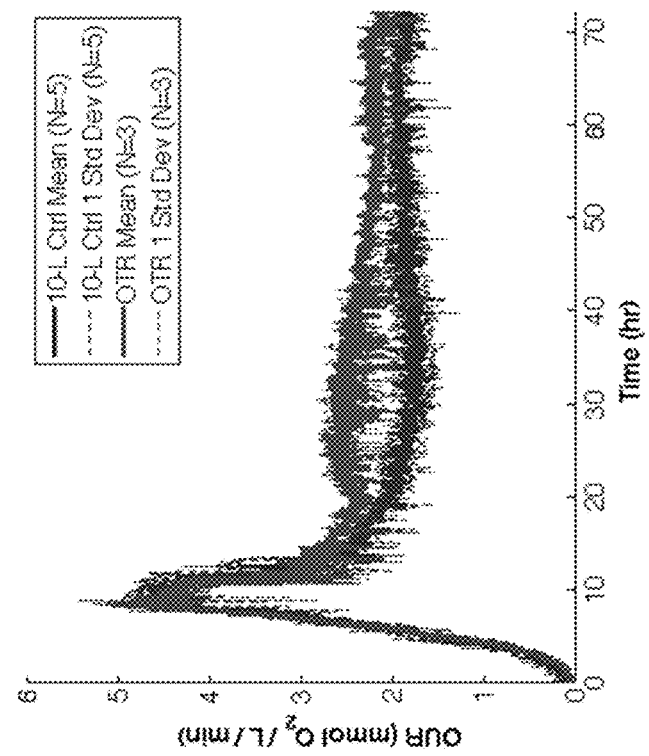
FIG. 48B shows the growth profiles for the altered OTR and control fermentation conditions. The altered OTR and control fermentations had similar growth profiles and both achieved peak an $OD_{550}$ of 250. xIL13 hAb control (Ctrl) best condition=1 bar back pressure (BP), 20 standard liters per minute (SLPM), and an agitation rate shift of 650 to 475 rpm. The xIL13 hAb altered OTR condition=0.3 bar back pressure, 13 SLPM, and an agitation rate shift of 880 to 650 rpm.
Figure 49:
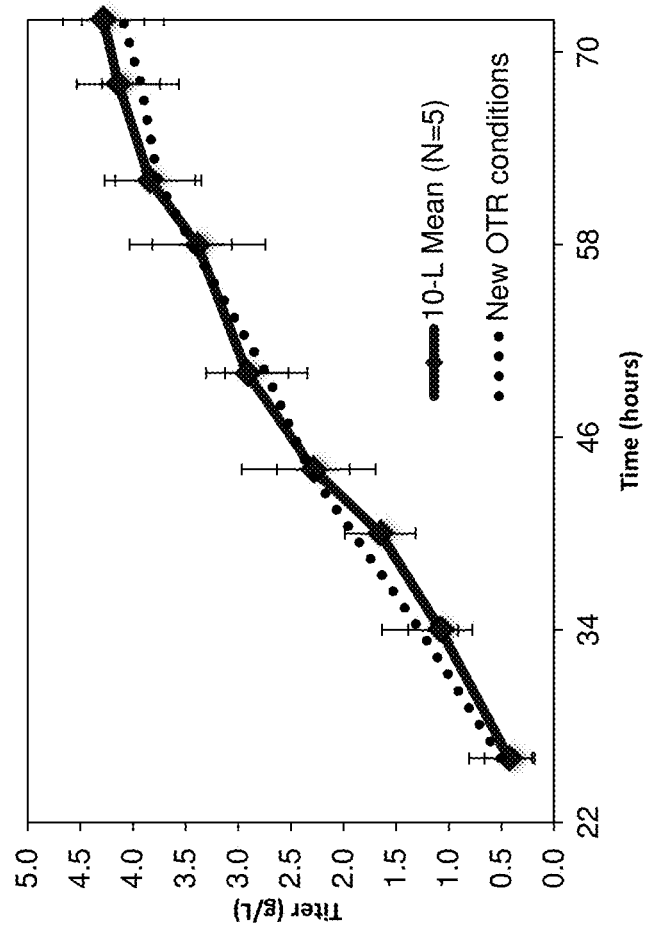
FIG. 49 shows the xIL13 hAb accumulation profiles for the altered OTR and control conditions. The altered and control conditions had similar accumulation profiles during fermentation and both achieved maximum average titers at 72 hours of 4.1 and 4.2 g/L, respectively.

Fermentations were performed with a constant BP for the entirety of the fermentation process. In the altered OTR conditions, the backpressure was maintained at 0.3 bar (N=3) and in the control conditions, the backpressure was maintained at 1.0 bar (N=5). Fermentations were performed with a constant air flow for the entirety of the fermentation process. In the altered OTR conditions, the air flow was maintained at 13 SLPM (N=3) and in the control conditions, the air flow was maintained at 20 SLPM (N=5). Fermentations implemented an agitation shift at 150 $OD_{550}$ in both the altered OTR and control conditions. In the altered OTR conditions, the initial agitation rate was set to 880 RPM and shifted to 650 RPM, and in the control conditions, the initial agitation rate was set to 650 RPM and shifted to 475 RPM. The increase in agitation rate compensated for the drop in OTR due to the reductions in sparge and backpressure. The altered OTR conditions resulted in similar peak and production phase OURs (FIG. 48A) and growth profiles (FIG. 48B) to the control condition. The altered OTR condition resulted in a similar accumulation profile and peak titer (4.1±0.4 g/L) as the control condition (FIG. 49).

Example 8: Optimization of ImmTAC Production

Immune mobilizing monoclonal T-cell receptors against cancer (ImmTACs) are two chain polypeptides of the present disclosure that are potentially useful for a range of anti-cancer therapies (see, e.g., Oates and Jakobsen, OncoImmunology 2:e22891, 2013, and Liddy et al., Nat. Med. 18:908-7, 2012) Like multispecific antibodies, producing ImmTACs for therapeutic use requires the ability to produce the building blocks, such as alpha and beta TCR chains and any polypeptides fused thereto (e.g., anti-CD3 effectors such as scFvs), on an industrial scale. To meet this demand, expression vectors and process steps were optimized to yield significant increases in production over standard methods. Importantly, like the above Examples, it was found that expression of FkpA, process changes, TIR optimization, and DsbC expression provided these increases in production for multiple ImmTACs.

Materials and Methods

Figure 50A:
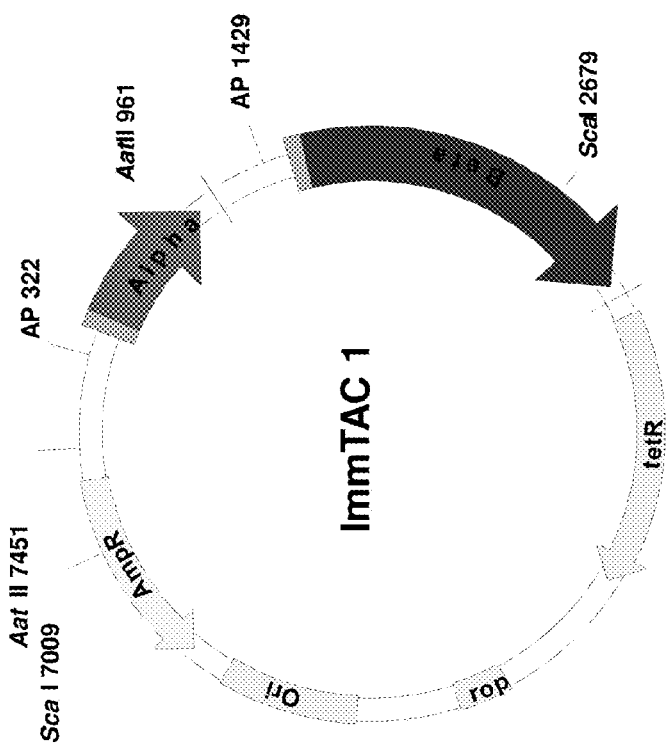
FIGS. 50A-50B illustrate the plasmid configuration of the TIR1,1 ImmTAC 1 production plasmid (FIG. 50A), along with a depiction of the TIR1,1 (FIG. 50B).
Figure 50B:

For the ImmTAC expression vectors (FIG. 50A), TIR combinations of 1,1; 1,2; and 2,3 were evaluated. As used herein in reference to ImmTACS production, the first number represents the TIR strength of the alpha chain and the second represents the TIR strength of the Beta chain (FIG. 50B).

Plasmids were transformed into a host strain, 67A6, with the genotype W3110 ΔfhuA ΔphoA ilvG2096 (Val$^r$) Δprc spr43H1 ΔdegP ΔmanA lacI$^Q$ ΔompT ΔmenE degpS210A.

The initial fermentations were performed at a constant 30° C. and pH 7.0 with an agitation ramp initiated at 24 hours over the course 4 hours and targeted an OUR of approximately 1.75 mmol/L/min.

A compatible plasmid (pACYC, Novagen, Madison, Wis.) was constructed containing the ORF for FkpA, as described supra and in European Patent No. EP1356052 B1. The FkpA gene construct was under the control of a tacII promoter.

The construction of the original oxidoreductase compatible plasmids was as described in European Patent No. EP1356052 B1 (see, e.g., Example 9). The screening of the oxidoreductases included expression from the compatible plasmid JJ141 (DsbC), JJ142 (DsbA) and JJ247 (DsbA/C)

with the ImmTAC TIR1,1 FkpA single plasmid. The tac promoter used to drive expression of the oxidoreductases was not induced and relied on leaky expression from the promoter.

For assaying ImmTAC titer, samples of the soluble fractions were submitted for analysis by a Protein L/RP assay. This assay is a two-dimensional HPLC assay where the first column is an affinity column that captures variable-light-chain containing IgG components and the second column is a reversed-phase column. An integral HPLC workstation was configured in the dual column mode. The solvent reservoirs were: Solvent 1A, affinity loading buffer, PBS; Solvent 1B, affinity elution buffer, 0.2% TFA in water; Solvent 2A, reversed-phase aqueous buffer, 0.1% TFA in water; Solvent 2B, reversed-phase organic elution buffer, 0.08% TFA in acetonitrile. The affinity column was an in-house packed column utilizing purified protein L purchased from Sigma Aldrich (CA, USA) coupled to POROS® AL activated resin purchased from Life Technologies (CA, USA). All procedures involving the affinity column were performed at ambient temperature.

The second column was HALO C4 protein reversed-phase column (2.1×20 mm) purchased from Mac-Mod (CA, USA). The reversed-phase column temperature was maintained at 80° C.

The affinity column was equilibrated in loading buffer and a sample was loaded at a flow rate of 2 ml/min. The flow-through was directed to waste. After the sample was loaded the affinity column was washed with loading buffer to reduce non-specifically bound components. Then by valve switching, the affinity column was connected to the reversed-phase column and eluted with elution buffer at a flow rate of 2 ml/min to transfer the affinity captured components to the reversed-phase column. During this transfer step the UV detector was located after the affinity column and before the reversed-phase column and hence monitored the elution of the affinity column (which became the load to the reversed-phase column).

After elution, the affinity column was subsequently re-equilibrated with loading buffer.

The loaded reversed-phase column was washed with aqueous 0.1% TFA. The flow rate was set to 2 ml/min and a rapid gradient was run from 5% to 30% solvent 2B (0.08% TFA in ACN) followed by a shallow gradient to 34% solvent 2B. Elution was completed by a gradient to 100% solvent 2B for regeneration. The reversed phase column was then returned to initial conditions to re-equilibrate. The column eluate was monitored at 280 and 214 nm. Quantitation was performed by comparison of the integrated peak areas with those of standards of known concentrations based on separation from the reversed-phase column. The limit of quantitation (LOQ) for this assay is 0.0125 g/L.

Results

Figure 51:
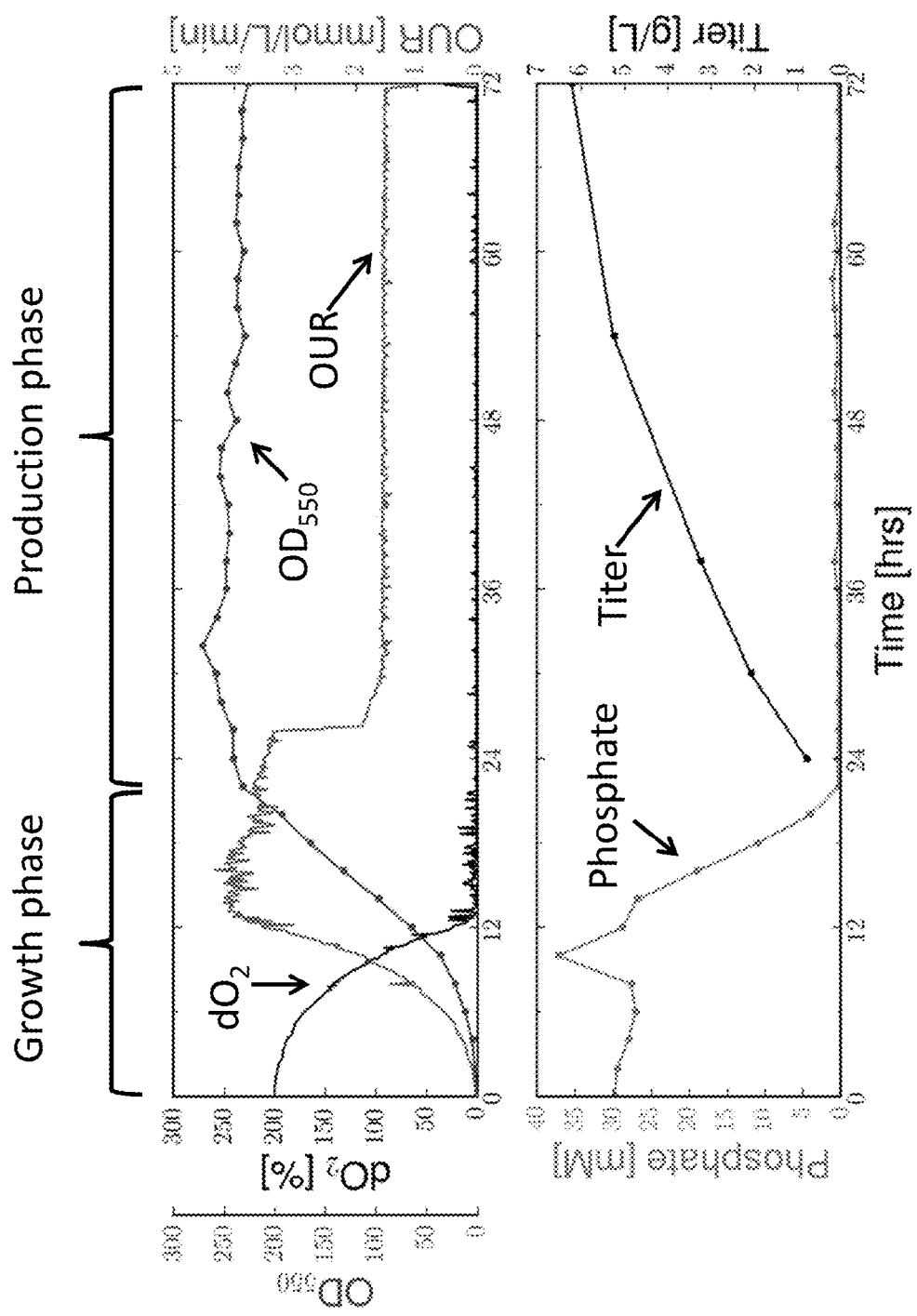
FIG. 51 illustrates the original (i.e., unoptimized) fermentation process used to produce ImmTACs.
Figure 52:
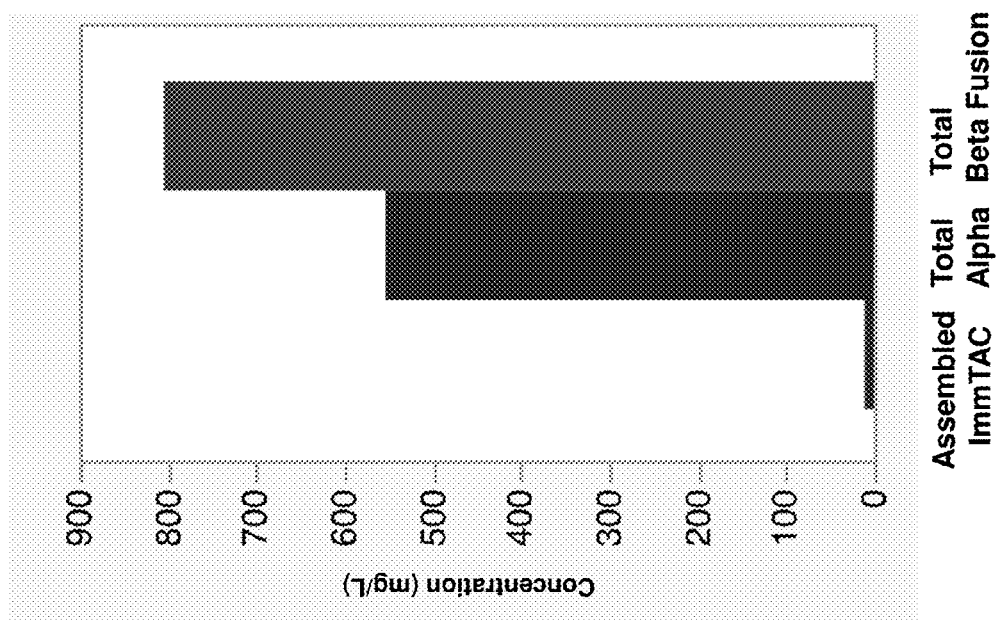
FIG. 52 shows the amount of assembled ImmTAC and total amounts of alpha and Beta subunits accumulated at the end of the fermentation process.

The initial fermentation evaluated the TIR1,1 construct (FIG. 51). Conditions were as follows: 30° C., pH 7.0, and an OUR of approximately 1.75 mmol $O_2$/L/min. The fermentation resulted in a titer accumulation of 10 mg/L. The total alpha and beta subunit accumulation was 550 and 800 mg/L, respectively (FIG. 52).

To determine the effect of chaperone expression on ImmTAC titers, plasmids were provided for co-expression of chaperones using the vectors described above. A number of known chaperones were tested in combination with ImmTAC expression, including FkpA protein, a peptidyl-proyl cis-trans isomerase with chaperone activity.

Figure 53:
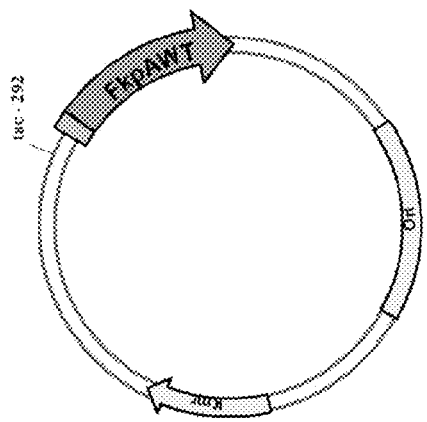
FIG. 53 provides plasmid maps of the ImmTAC production plasmid and the compatible plasmid containing the FkpA ORF under control of a tac promoter.
Figure 53:
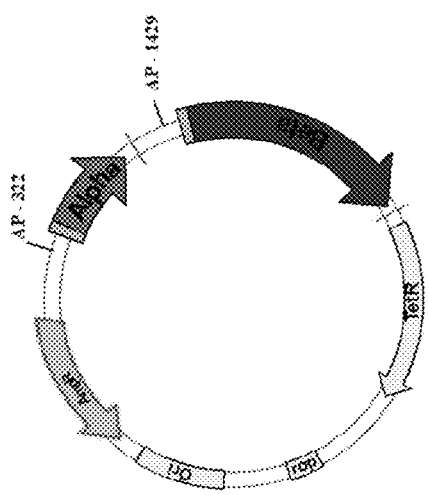

The FkpA compatible plasmid was then co-transformed with the TIR1,1 ImmTAC 1 expression plasmid described above (FIG. 53) into strain 67A6. The fermentation conditions were identical to those used in the initial fermentation described above and shown in FIG. 51. The FkpA tac promoter was induced with 1 mM IPTG when the culture reached 200 $OD_{550}$ Anti-alpha and anti-beta soluble Western blots indicated an increase in the accumulation of both alpha and beta soluble subunits (soluble reduced blot; FIG. 54A), in addition to assembled ImmTAC. Titer analysis also indicated a 2 fold increase in assembled ImmTAC compared to the no-chaperone condition, with a final titer of 20 mg/L (FIG. 54B).

Figure 55:
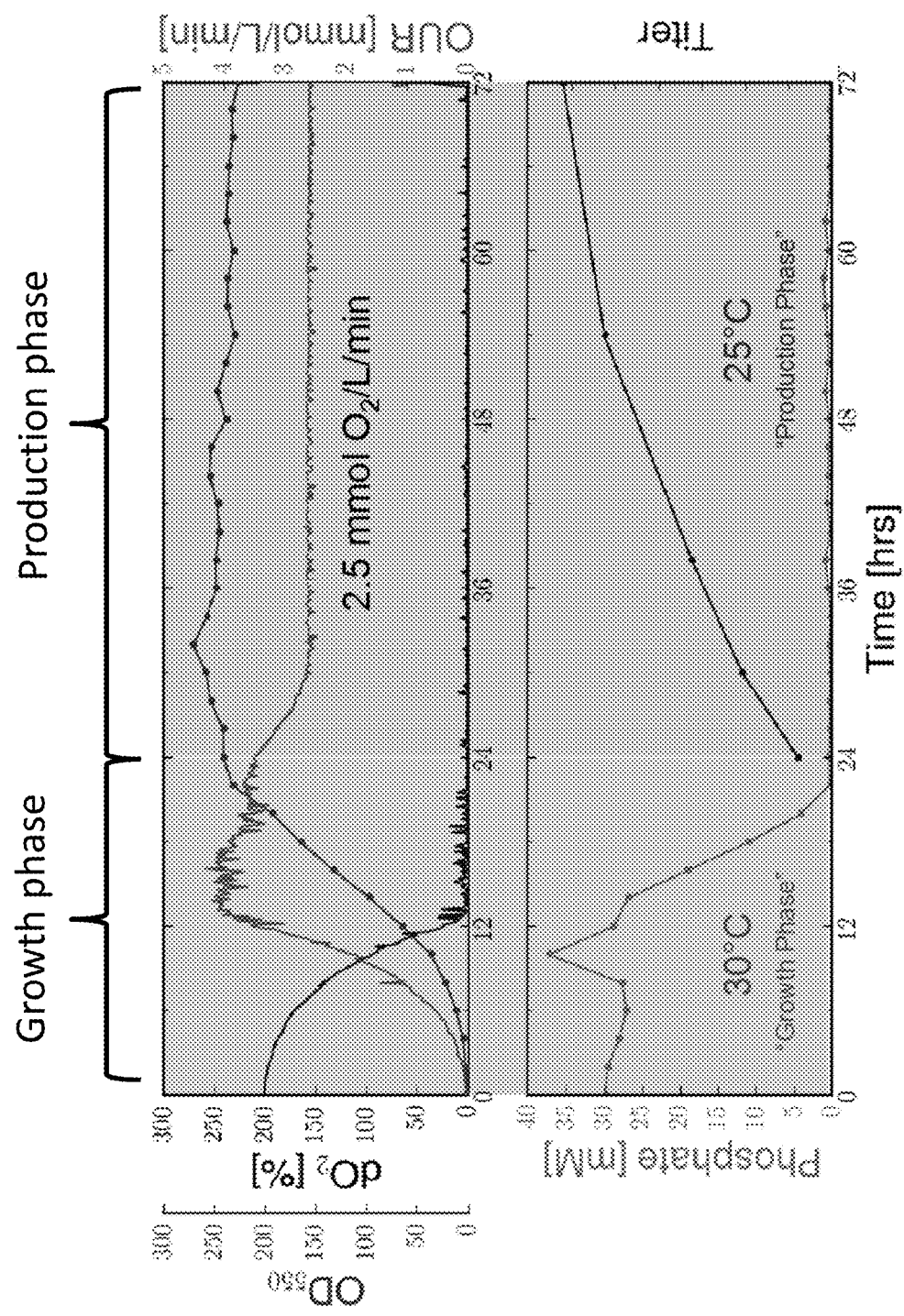
FIG. 55 illustrates the improved fermentation process conditions used to produce ImmTACs.
Figures 56A, 56B:
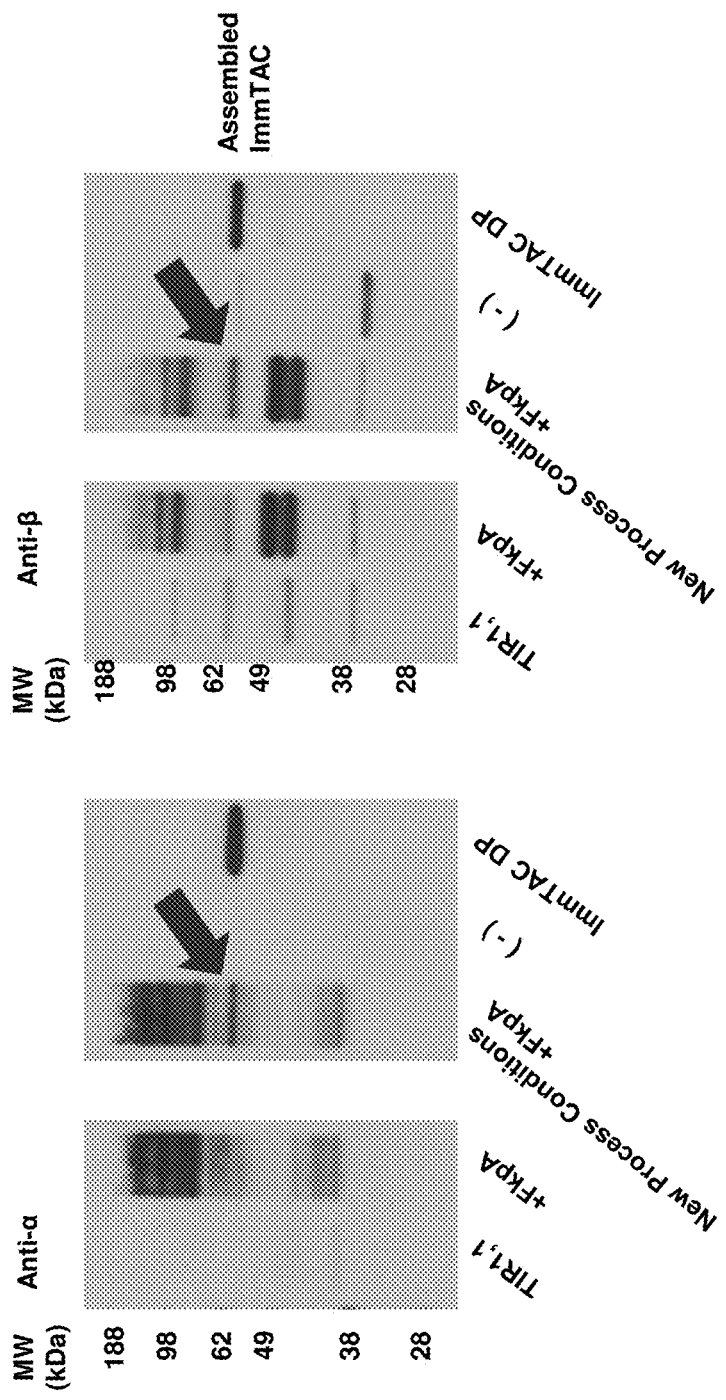
FIGS. 56A-56B show the soluble and soluble reduced anti-alpha (FIG. 56A) and anti-beta (FIG. 56B) Western blots for the following conditions: without chaperones (TIR1,1), with FkpA (+FkpA), with FkpA and the new process conditions (New Process Conditions+FkpA), negative control (−), and the ImmTAC 1 positive control (ImmTAC DP).

The fermentation process conditions were changed in subsequent ImmTAC experiments (FIG. 55). In all subsequent fermentations the agitation ramp targeted a specific OUR set point of approximately 2.5 mmol $O_2$/L/min. In addition a temperature shift was performed at 24 hours that reduced the growth temperature from 30° C. to a production temperature of 25° C.

Figure 57:
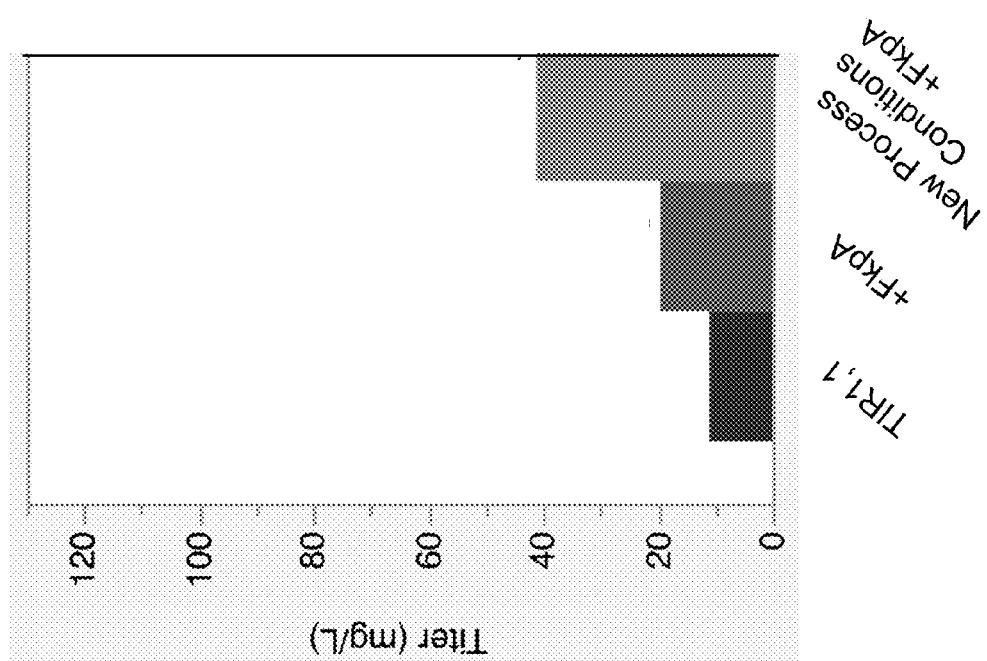
FIG. 57 shows the final titer for the following conditions: TIR1,1; TIR1,1 with FkpA; and TIR1,1 with FkpA and the new process conditions.

The altered process conditions were tested using the FkpA compatible system described above and included the addition of 1 mM IPTG at 200 $OD_{550}$. The use of the altered process conditions resulted in an approximate 2 fold increase in titer when compared to the previous process conditions with a final titer of 40 mg/L (FIG. 57).

Figure 58:
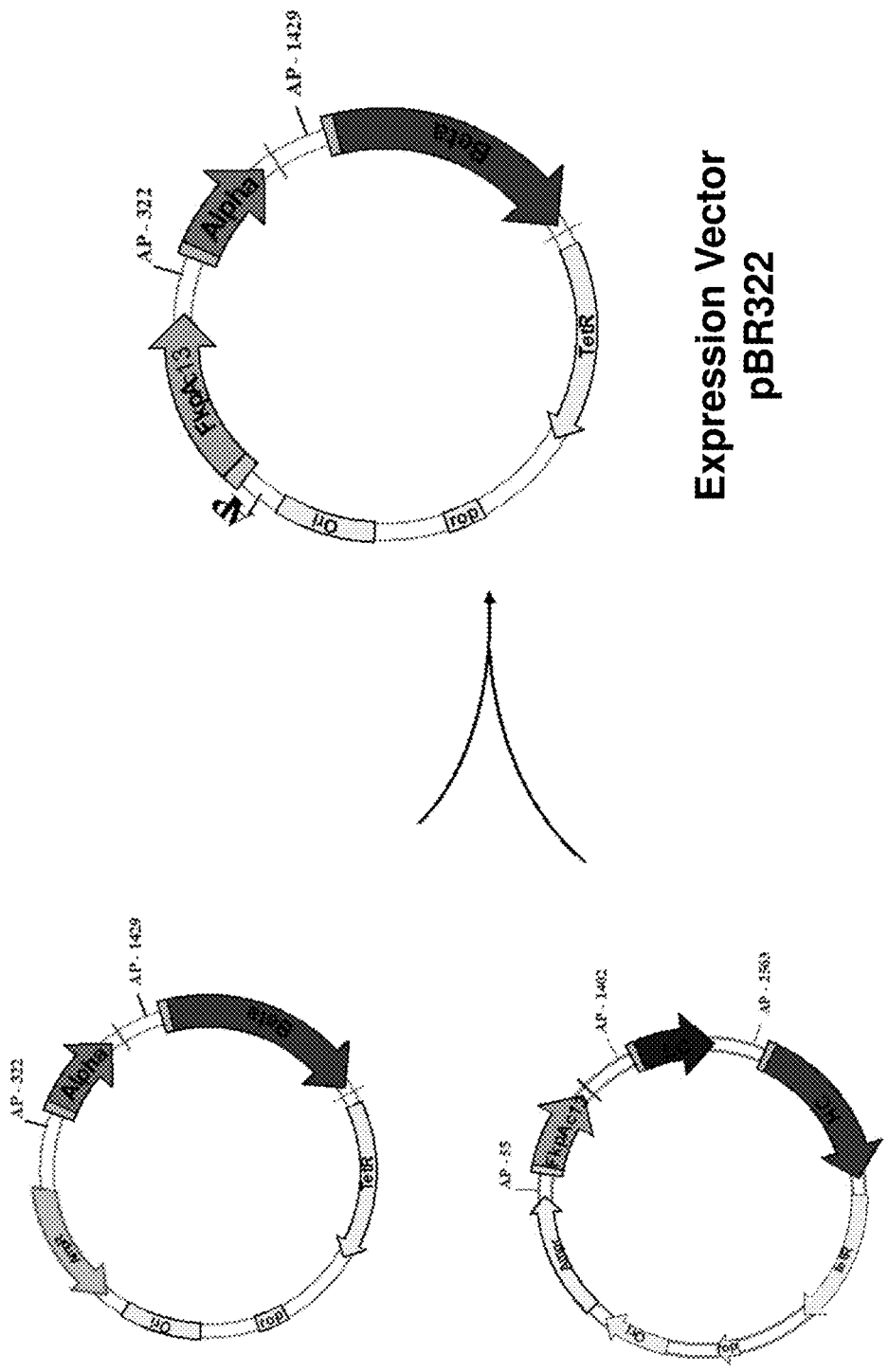
FIG. 58 illustrates the construction of a single plasmid that incorporates the ImmTAC alpha chain and beta chain ORFs and the FkpA ORF under control of a phoA promoter.

For the ImmTAC TIR1,1; TIR1,2; and TIR2,3, a plasmid encoding the alpha and beta chains of the ImmTAC and FkpA was constructed and used to transform 67A6 (FIG. 58). In these plasmid constructs, the FkpA ORF was upstream of the alpha ORF and a phoA promoter controlled transcription. The pBR322 plasmid is typically maintained at approximately 30 copies/cell (Bolivar et al., Gene, 2:95-113, 1977), and the pACYC plasmid is typically maintained at approximately 15 copies/cell (Chang and Cohen, J. Bacteriol., 134:1141-1156, 1978). Without wishing to be bound to theory, it is thought that an increase in copy number when FkpA is moved onto the ImmTAC expression plasmid may result in an increase in the amount of FkpA made.

Figure 59B:
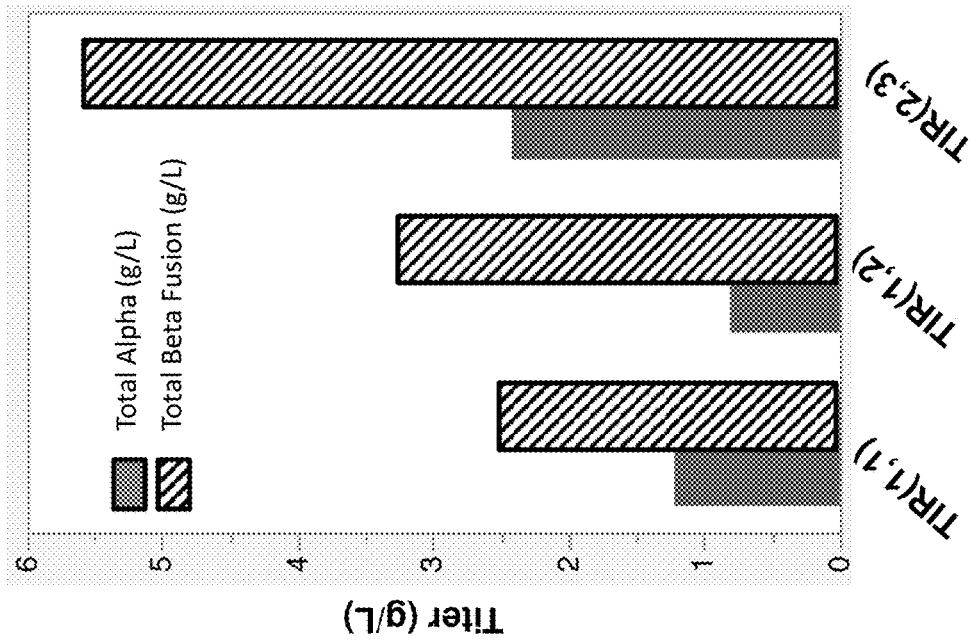
FIG. 59B shows the final subunit accumulation of both alpha and beta ImmTAC chains for the TIR1,1; the TIR1,2; and the TIR2,3 single plasmids that incorporate the FkpA ORF.
Figure 59A:
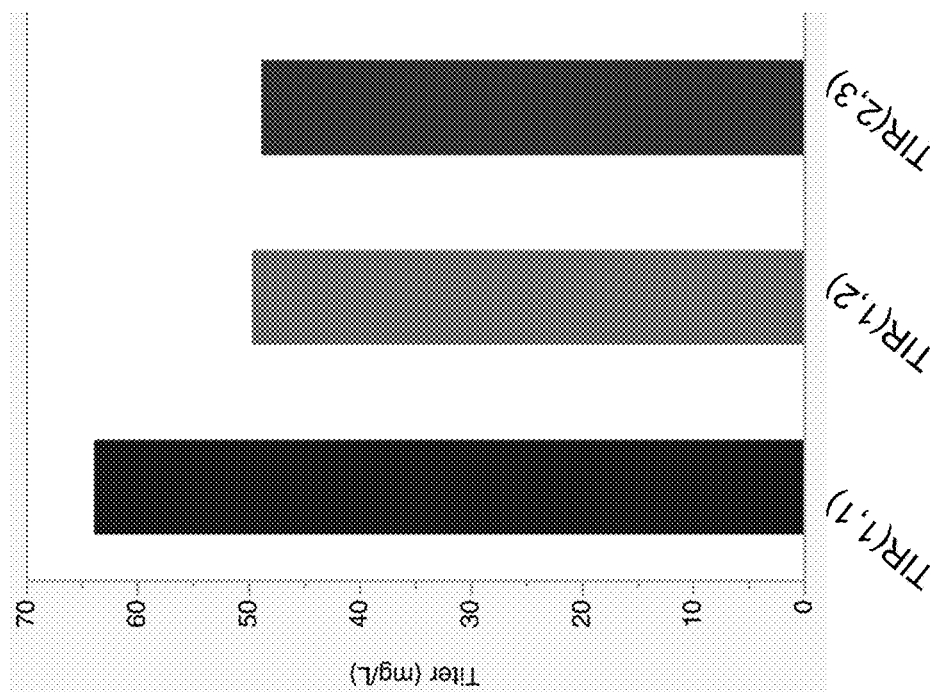
FIG. 59A shows the final ImmTAC 1 titer for the TIR1,1; the TIR1,2; and the TIR2,3 single plasmids that incorporate the FkpA ORF.

The three ImmTAC TIR variant single plasmids incorporating the FkpA ORF resulted in higher titers than the TIR1,1 compatible FkpA system described previously. The TIR1,2 and TIR 2,3 conditions resulted in titers of approximately 50 mg/L each (FIG. 59A), while the TIR1,1 condition resulted in a titer of 65 mg/L (FIG. 59A). The total alpha and beta subunit accumulation for the TIR2,3 condition was 2.5 and 5.5 g/L, respectively (FIG. 59B). In the TIR1,1 condition the total alpha and beta subunit accumulation was 1 g/L and 2.5 g/L, respectively. In the TIR1,2 condition alpha and beta subunit accumulation was approximately 0.8 g/L and 3.2 g/L, respectively (FIG. 59B).

Figure 60B:
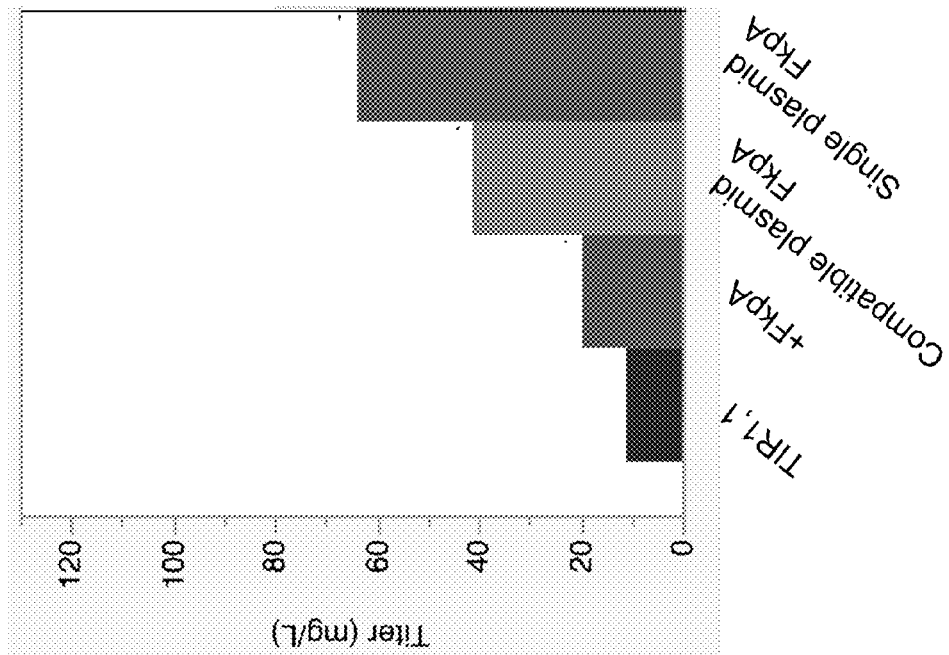
FIG. 60B shows the final titer for the following conditions: TIR1,1 only; TIR1,1 with FkpA; TIR1,1 FkpA compatible plasmid system; and TIR1,1 FkpA single plasmid system.
Figure 60A:
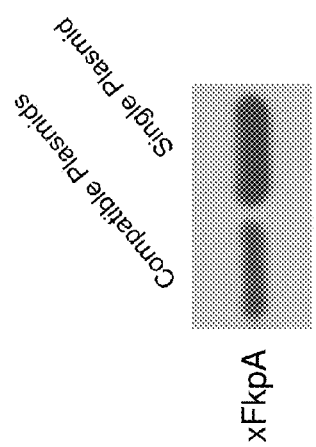
FIG. 60A shows a Western blot probed for FkpA from fermentations performed with the ImmTAC TIR1,1 production plasmid and the compatible FkpA plasmid and the single TIR1,1 plasmid containing the FkpA ORF.

Comparison of the TIR1,1 single plasmid and TIR1,1 compatible plasmid systems with regard to soluble FkpA expression (assayed by Western blot) indicated that the single plasmid system resulted in an increase in the amount of FkpA produced (FIG. 60A). The increase in soluble FkpA resulted in a further increase in titer when compared to the previous compatible plasmid system and achieved a final titer of 65 mg/L (FIG. 60B).

Figure 61:
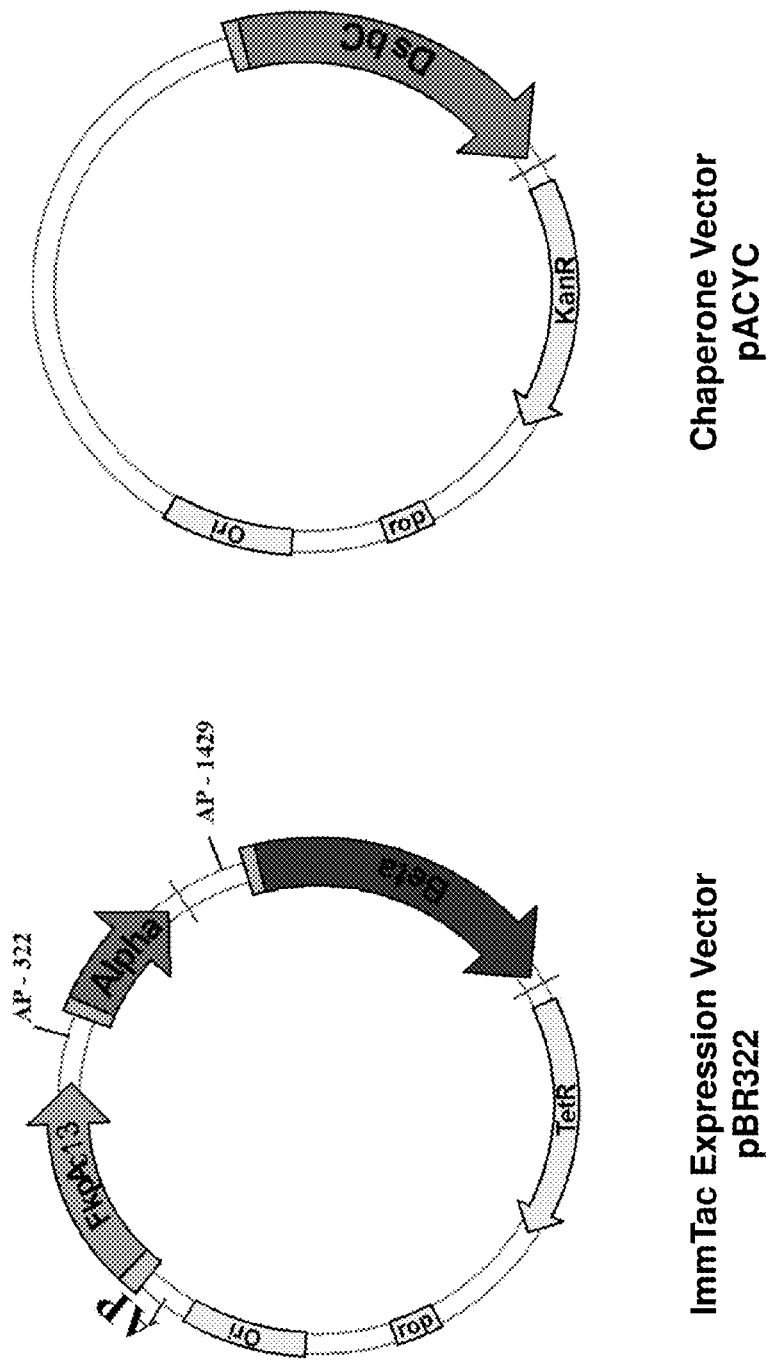
FIG. 61 provides plasmids maps of the ImmTAC production plasmid containing the FkpA, alpha chain and beta chain ORFs and a compatible plasmid containing an oxidoreductase (e.g., DsbC) under control of a tac promoter.
Figure 62:
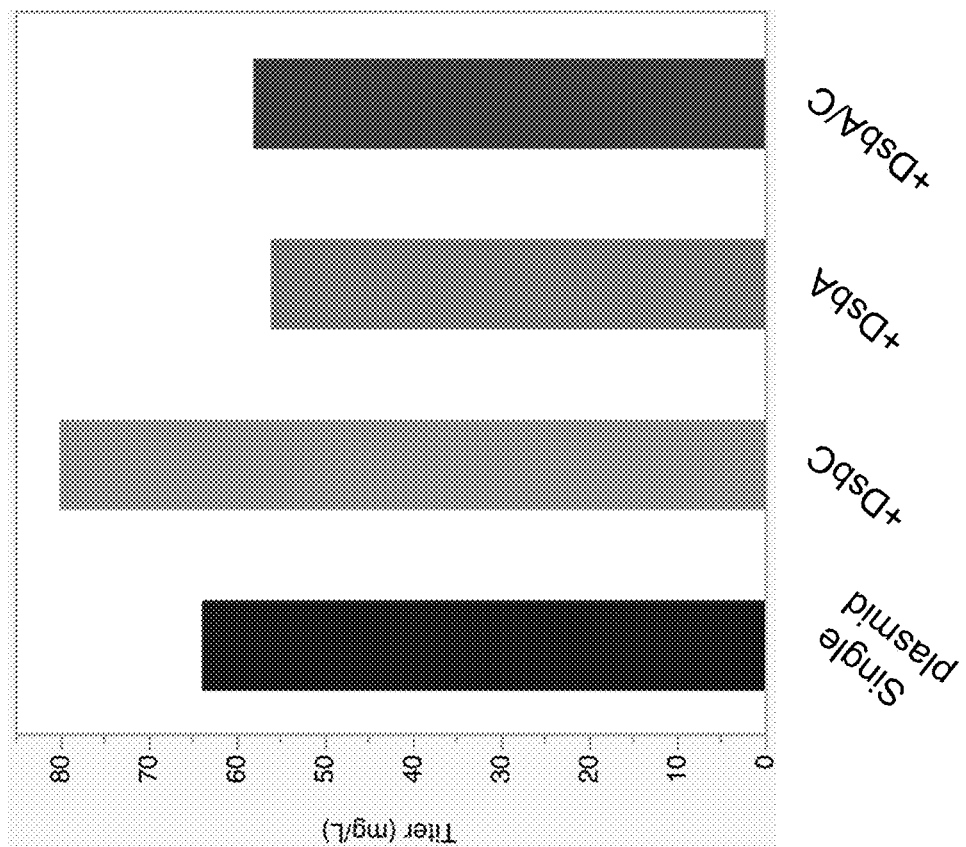
FIG. 62 shows the final titer from fermentations performed with the TIR1,1 single plasmid that incorporated the FkpA ORF with the compatible plasmids that contained the ORF(s) of DsbA alone, DsbC alone, or DsbA and DsbC combined.
Figure 63:
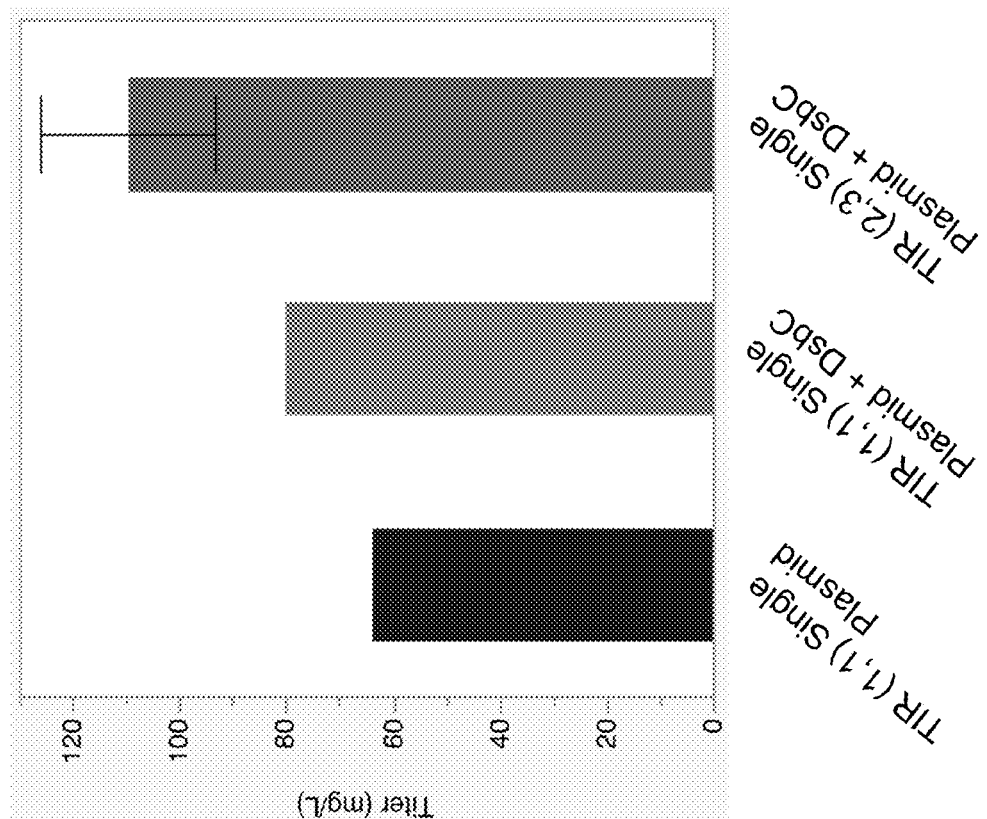
FIG. 63 shows the final titer from fermentations performed with the TIR1,1 single plasmid alone; the TIR1,1 single plasmid with the DsbC compatible plasmid; and the TIR2,3 single plasmid with the DsbC compatible plasmid.

Similar to the compatible plasmid system described for the co-expression of FkpA, compatible plasmids were utilized to screen various known oxidoreductases in combination with the TIR1,1 ImmTAC 1 that incorporated the FkpA ORF previously described (FIG. 61). The coexpression of DsbA alone and DsbA in combination with DsbC resulted in a similar decrease in titer of 20 mg/ml when compared to the previous FkpA only condition. However, the co-expression of DsbC alone resulted in a titer of 80 mg/L, which corresponded to a 15-20 mg/L increase in assembled ImmTAC production (FIG. 62). The increase in assembled titer in the TIR1,1 single plasmid with the coexpression of DsbC led to the hypothesis that the increased subunit accumulation seen in the previous FkpA single TIR2,3 condition may provide further benefit to folding and assembly of the individual subunits and may further increase titers. The TIR2,3 FkpA single plasmid was tested with the DsbC compatible system (N=4) and resulted in an average titer of 110 mg/L (FIG. 63).

Figure 64:
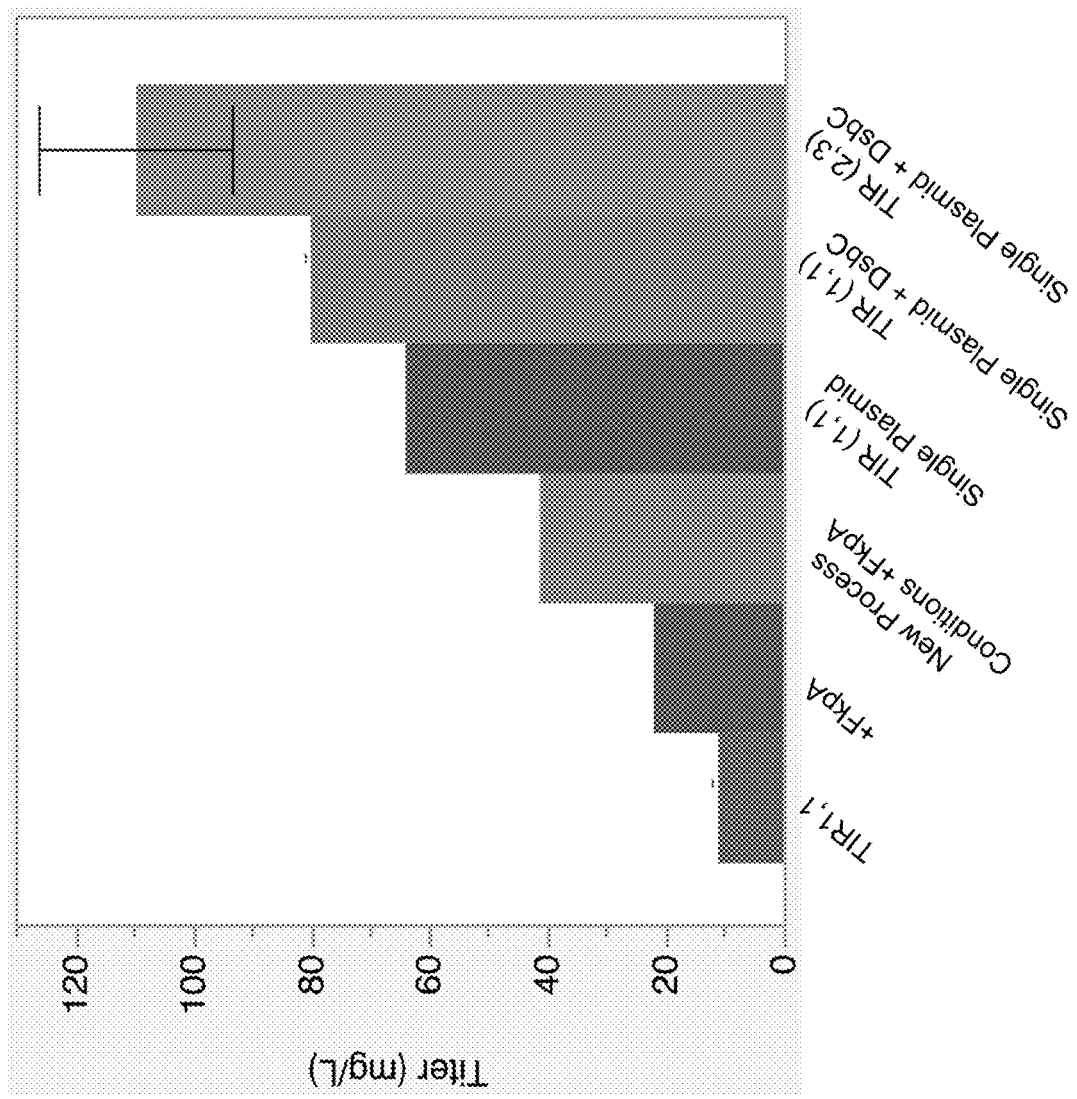
FIG. 64 shows the cumulative increase in final titer using the above optimizations, from the initial TIR1,1 production plasmid to the TIR2,3 single plasmid with the DsbC compatible plasmid.

Importantly, the optimization of alpha and beta subunit TIRs, in conjunction with the co-expression of the chaperones FkpA and DsbC and the improved process conditions described above (FIG. 55), resulted in a 10-fold increase in ImmTAC 1 titer (FIG. 64). Optimization steps to ImmTAC 1 production included the co-expression of FkpA, process changes (increased OUR, more basic pH, temperature shift), a single plasmid system with FkpA and ImmTAC 1, leaky DsbC expression, and increased TIR strength.

Figure 65A:
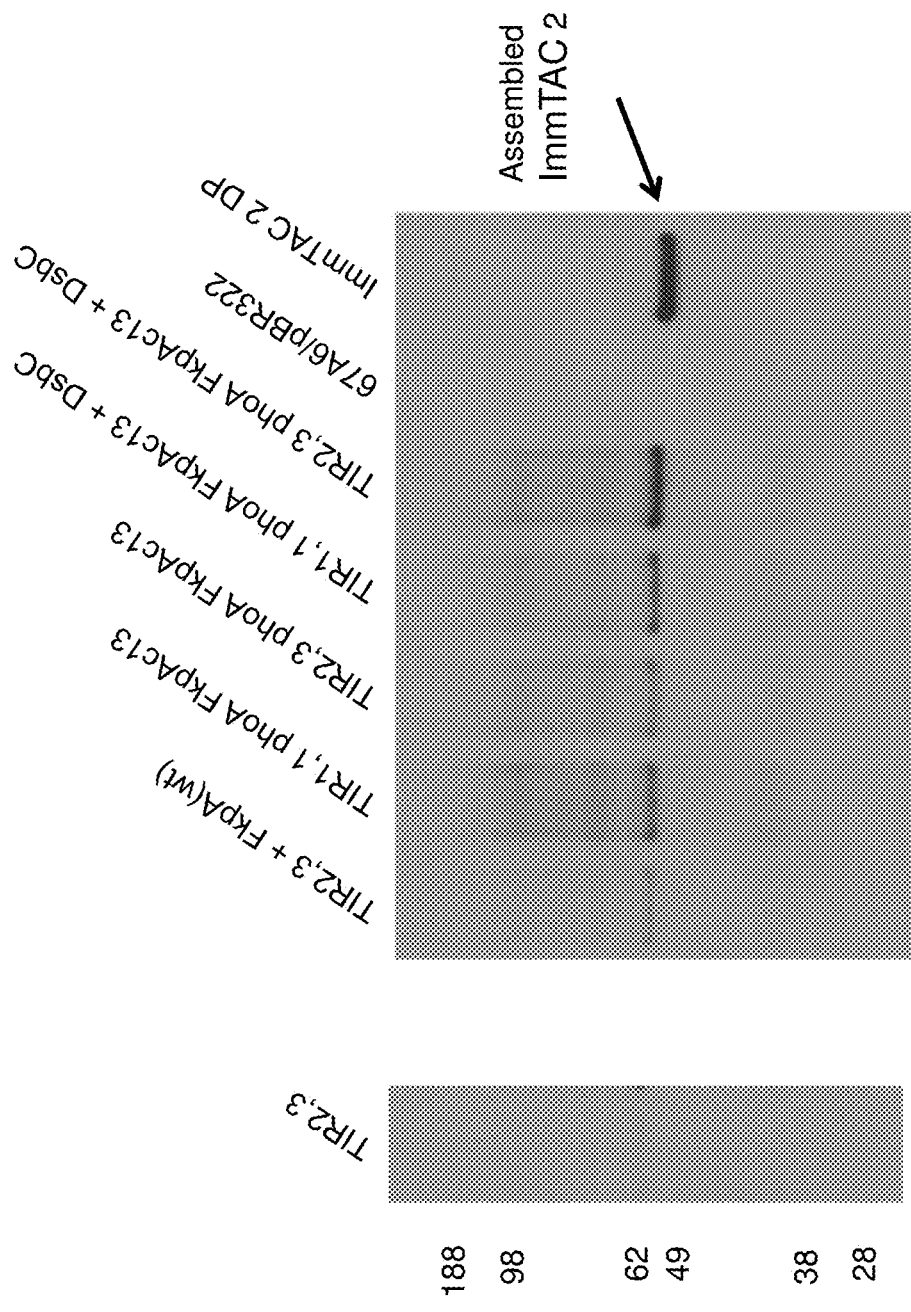
FIGS. 65A-65B show the ImmTAC 2 molecule tested with a TIR2,3 production plasmid with and without the compatible FkpA plasmid; as a single TIR1,1 and TIR2,3 plasmid incorporating the FkpA ORF; and as a single TIR1,1 and TIR2,3 plasmid incorporating the FkpA ORF with the compatible DsbC plasmid. Western blots showing the production of alpha (FIG. 65A) and beta (FIG. 65B) chains are provided.
Figure 65B:
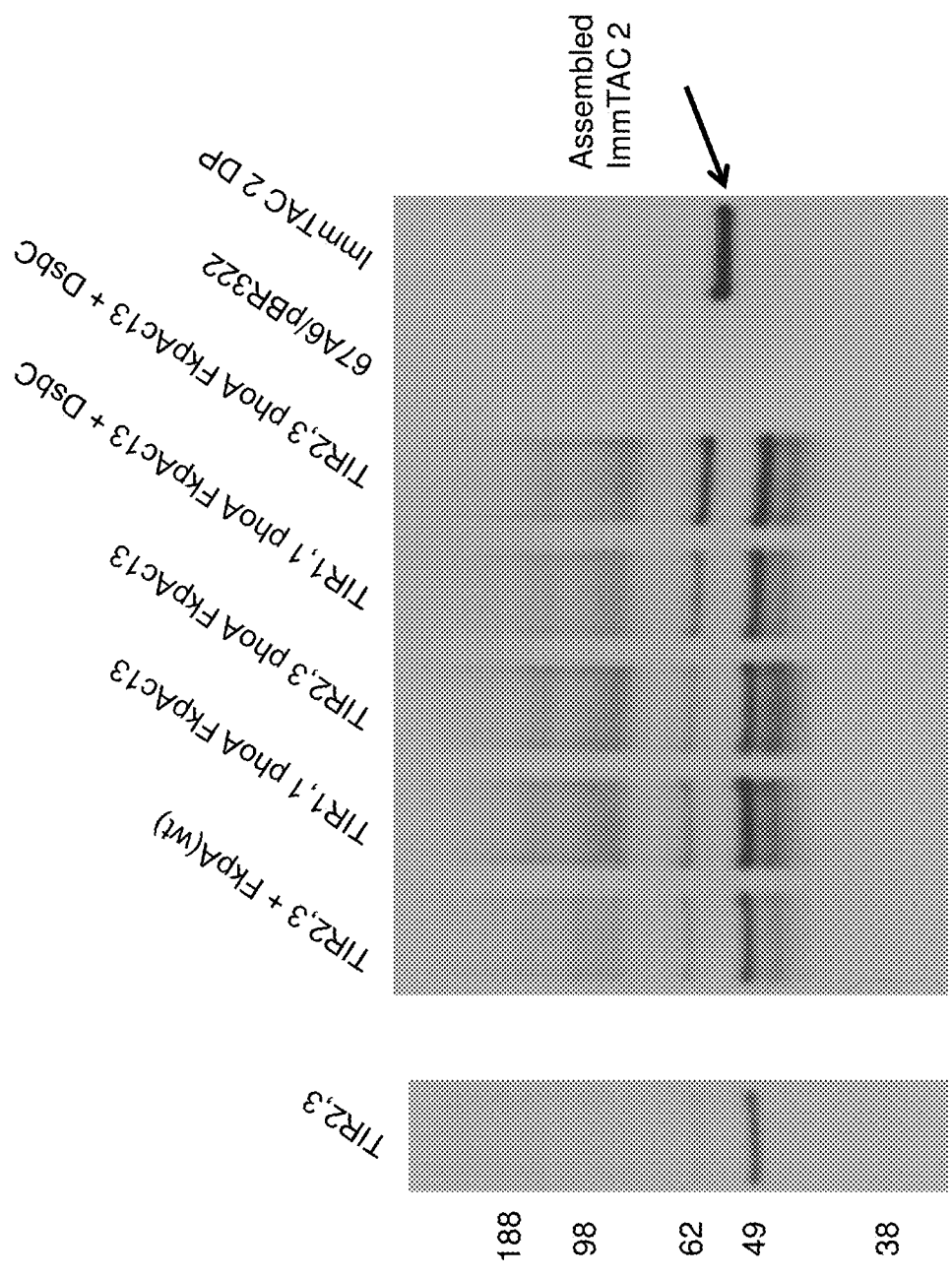

The above optimizations were assessed using ImmTAC 1. A second, distinct ImmTAC, ImmTAC 2, was tested using the same optimizations. As shown in FIG. 65A (alpha chain blot) and FIG. 65B (beta chain blot), the same ImmTAC TIR and chaperone conditions provide the greatest benefit to assembled ImmTAC 2.

Taken together, these results demonstrate that co-expression of FkpA along with DsbC and key process improvements increases the production of assembled ImmTAC, using multiple ImmTAC constructs to confirm these effects.

SEQUENCES

All polypeptide sequences are presented N-terminal to C-terminal unless otherwise noted. All polynucleotide sequences are presented 5' to 3' unless otherwise noted.

```
FkpA TIR1
                                             (SEQ ID NO: 1)
GAATTATGAA GTCCCTGTTT AAAGTGACGC TGCTGGCGAC

CACAATGGCC GTTGCCCTGC ATGCACCAAT CACTTTTGCT

FkpA TIR2
                                             (SEQ ID NO: 2)
GAATTATGAA GTCGCTATTC AAAGTGACGC TGCTGGCGAC

CACAATGGCC GTTGCCCTGC ATGCACCAAT CACTTTTGCT

FkpA TIR3 (c13)
                                             (SEQ ID NO: 3)
GAATTATGAA GTCGCTGTTT AAAGTTACGC TGCTGGCGAC

CACAATGGCC GTTGCCCTGC ATGCACCAAT CACTTTTGCT

FkpA signal peptide
                                             (SEQ ID NO: 4)
MKSLFKVTLLATTMAVALHAPITFA
```

What is claimed is:

1. A method of producing an immune mobilizing monoclonal T-cell receptor against cancer (ImmTAC) comprising a T-cell receptor (TCR) alpha chain and a TCR beta chain in a prokaryotic host cell, the method comprising:
   (a) culturing the host cell to express the TCR alpha chain and the TCR beta chain of the ImmTAC in a culture medium under conditions comprising:
   a growth phase comprising a growth temperature and a growth agitation rate,
   a temperature shift from the growth temperature to a lower production temperature, an agitation rate shift from the growth agitation rate to a lower production agitation rate, and
   a production phase comprising the production temperature and the production agitation rate, whereby upon expression the TCR alpha chain and the TCR beta chain fold and assemble to form a biologically active ImmTAC in the host cell;
   wherein the host cell comprises a polynucleotide comprising
   (1) a first translational unit encoding the TCR alpha chain of the ImmTAC;
   (2) a second translational unit encoding the TCR beta chain of the ImmTAC; and
   (3) a third translational unit encoding at least one chaperone protein selected from the group consisting of peptidyl-prolyl isomerases, protein disulfide oxidoreductases, and combinations thereof;
   wherein the growth temperature is in the range of about 30° C. to about 34° C. during the growth phase, the production temperature is in the range of about 25° C. to about 29° C. during the production phase, and the growth agitation rate is from 50 to 250 rpm above the production agitation rate; and
   (b) recovering the biologically active ImmTAC from the host cell.

2. The method of claim 1, wherein the polynucleotide further comprises three copies of a promoter, wherein a first copy is in operable combination with the first translational unit, a second copy is in operable combination with the second translational unit, and a third copy is in operable combination with the third translational unit to drive transcription of the first chain, the second chain and the chaperone protein.

3. The method of claim 2, wherein the promoter is an inducible promoter.

4. The method of claim 3, wherein the inducible promoter is an IPTG-inducible promoter that drives transcription of the TCR alpha chain, the TCR beta chain and the chaperone protein in the absence of IPTG induction.

5. The method of claim 3, wherein the inducible promoter is a Pho promoter that drives transcription of the TCR alpha chain, the TCR beta chain and the chaperone protein when phosphate in the culture medium has been depleted.

6. The method of claim 1, wherein the polynucleotide further comprises a selectable marker and the culture medium comprises a selection agent consisting of a single antibiotic to cause the host cell to retain the polynucleotide.

7. The method of claim 1, wherein the first translational unit comprises a first translation initiation region (TIR) in operable combination with a coding region of the TCR alpha chain, and the second translational unit comprises a second translation initiation region (TIR) in operable combination with a coding region of the TCR beta chain, wherein the relative translation strength of the first and second TIR is from about 1.0 to about 3.0.

8. The method of claim 1, wherein the at least one chaperone protein comprises a first chaperone protein, wherein the first chaperone protein is a peptidyl-prolyl isomerase.

9. The method of claim 8, wherein the peptidyl-prolyl isomerase is an FkpA protein.

10. The method of claim 9, wherein the FkpA is *E. coli* FkpA.

11. The method of claim 8, wherein the at least one chaperone protein further comprises a second chaperone protein and a third chaperone protein, wherein the second chaperone protein is a first protein disulfide oxidoreductase and the third chaperone protein is a second protein disulfide oxidoreductase.

12. The method of claim 11, wherein the first protein disulfide oxidoreductase is a DsbA protein and the second protein disulfide oxidoreductase is a DsbC protein.

13. The method of claim 12, wherein the DsbA protein is *E. coli* DsbA and the DsbC protein is *E. coli* DsbC.

14. The method of claim 1, wherein the prokaryotic host cell is a gram-negative bacterium.

15. The method of claim 14, wherein the gram-negative bacterium is *E. coli*.

16. The method of claim 15, wherein the *E. coli* is a strain with a degpS210A mutation.

17. The method of claim 15, wherein the *E. coli* is a strain with a genotype of W3110 ΔfhuA ΔphoA ilvG2096 (Val$^r$) Δprc spr43H1 ΔdegP ΔmanA lacI$^Q$ ΔompT ΔmenE degpS210A.

18. The method of claim 1, wherein the TCR alpha chain comprises a TCR alpha chain variable domain and a TCR alpha chain constant domain, and wherein the TCR beta chain comprises a TCR beta chain variable domain and a TCR beta chain constant domain.

19. The method of claim 1, wherein the two chains of the ImmTAC are linked to each other by at least one disulfide bond.

20. The method of claim 1, wherein the ImmTAC further comprises an antibody fragment that binds a T cell and activates a T cell response.

21. The method of claim 20, wherein the antibody fragment comprises an anti-CD3 single chain antibody fragment.

22. The method of claim 1, wherein the ImmTAC comprises a TCR engineered to possess increased affinity for an antigen, as compared to affinity for the antigen of TCR that has not been engineered.

23. The method of claim 1, wherein the ImmTAC is recovered from the periplasm of the host cell.

24. The method of claim 1, wherein the growth agitation rate is sufficient to achieve an oxygen uptake rate in the host cell during the growth phase of from 0.5 to 2.5 mmol/L/min above a peak oxygen uptake rate in the host cell during the production phase.

25. The method of claim 1, wherein the peak oxygen uptake rate of the host cell during the growth phase is in the range of 3.5 to 4.5 mmol/L/min, and the oxygen uptake rate of the host cell during the production phase is in the range of 1.0 to 3.0 mmol/L/min.

26. The method of claim 1, wherein the growth agitation rate is from 10% to 40% higher than the production agitation rate.

27. A method of producing an immune mobilizing monoclonal T-cell receptor against cancer (ImmTAC) comprising a T-cell receptor (TCR) alpha chain and a TCR beta chain in a prokaryotic host cell, the method comprising:
 (a) culturing the host cell to express the TCR alpha chain and the TCR beta chain of the ImmTAC in a culture medium under conditions comprising:
 a growth phase comprising a growth temperature and a growth agitation rate,
 a temperature shift from the growth temperature to a lower production temperature, an agitation rate shift from the growth agitation rate to a lower production agitation rate, and
 a production phase comprising the production temperature and the production agitation rate, whereby upon expression the TCR alpha chain and the TCR beta chain fold and assemble to form a biologically active ImmTAC in the host cell;
  wherein the host cell comprises a polynucleotide comprising:
  (1) a first translational unit encoding the TCR alpha chain of the ImmTAC;
  (2) a second translational unit encoding the TCR beta chain of the ImmTAC;
  (3) a third translational unit encoding a first chaperone protein;
  (4) a fourth translational unit encoding a second chaperone protein; and
  (5) a fifth translational unit encoding a third chaperone protein,
  wherein the first, second and third chaperone proteins are selected from the group consisting of peptidyl-prolyl isomerases, protein disulfide oxidoreductases, and combinations thereof;
  wherein the growth temperature is in the range of about 30° C. to about 34° C. during the growth phase, the production temperature is in the range of about 25° C. to about 29° C. during the production phase, and the growth agitation rate is from 50 to 250 rpm above the production agitation rate; and
 (b) recovering the biologically active ImmTAC from the host cell.

\* \* \* \* \*